United States Patent
Linton et al.

(10) Patent No.: US 9,421,331 B2
(45) Date of Patent: *Aug. 23, 2016

(54) COMBINATION PRESSURE THERAPY

(75) Inventors: Carl E. Linton, Temecula, CA (US); Allen Ruszkowski, San Jose, CA (US)

(73) Assignee: CVAC Systems, Inc., Temecula, CA (US)

( * ) Notice: Subject to any disclaimer, the term of this patent is extended or adjusted under 35 U.S.C. 154(b) by 1182 days.

This patent is subject to a terminal disclaimer.

(21) Appl. No.: 13/202,543

(22) PCT Filed: Feb. 25, 2008

(86) PCT No.: PCT/US2008/054923
§ 371 (c)(1),
(2), (4) Date: Aug. 19, 2011

(87) PCT Pub. No.: WO2008/106410
PCT Pub. Date: Sep. 4, 2008

(65) Prior Publication Data
US 2012/0048284 A1 Mar. 1, 2012

Related U.S. Application Data

(60) Provisional application No. 60/891,696, filed on Feb. 26, 2007, provisional application No. 60/953,973, filed on Aug. 3, 2007, provisional application No. 60/953,972, filed on Aug. 3, 2007, provisional application No. 61/025,272, filed on Jan. 31, 2008.

(51) Int. Cl.
A61G 10/02 (2006.01)
A61H 99/00 (2006.01)
A61M 5/172 (2006.01)

(52) U.S. Cl.
CPC ........... *A61M 5/1723* (2013.01); *A61G 10/023* (2013.01); *A61H 99/00* (2013.01); *A61H 2230/20* (2013.01); *A61M 2230/20* (2013.01)

(58) Field of Classification Search
None
See application file for complete search history.

(56) References Cited

U.S. PATENT DOCUMENTS

| | | |
|---|---|---|
| 3,073,040 A | 1/1963 | Schueller |
| 4,227,524 A | 10/1980 | Galerne |
| 4,427,385 A | 1/1984 | Galerne |
| 4,678,438 A | 7/1987 | Vykukal |
| 4,835,983 A | 6/1989 | Chandler et al. |
| 5,318,018 A | 6/1994 | Puma et al. |
| 5,360,001 A | 11/1994 | Brill et al. |
| 5,370,870 A | 12/1994 | Wong |
| 5,467,764 A | 11/1995 | Gamow |
| 5,490,784 A | 2/1996 | Carmein et al. |
| 5,531,644 A | 7/1996 | Marumo |
| 5,718,587 A | 2/1998 | Sussingham |
| 6,565,624 B2 | 5/2003 | Kutt et al. |
| 6,719,564 B2 | 4/2004 | Than et al. |
| 6,899,103 B1 | 5/2005 | Hood et al. |
| 8,899,228 B2 | 12/2014 | Linton et al. |
| 2002/0035927 A1 | 3/2002 | Kutt et al. |
| 2002/0083025 A1 | 6/2002 | Robarts et al. |
| 2004/0006926 A1 | 1/2004 | Neeley et al. |
| 2004/0112375 A1 | 6/2004 | Boykin, Jr. |
| 2004/0180043 A1 | 9/2004 | Sabbah et al. |
| 2004/0261796 A1 | 12/2004 | Butler |
| 2005/0000520 A1 | 1/2005 | Silman et al. |
| 2005/0008991 A1 | 1/2005 | Hebert et al. |
| 2005/0026136 A1 | 2/2005 | Weiss et al. |
| 2005/0056279 A1* | 3/2005 | Linton ............... 128/202.12 |
| 2005/0056285 A1 | 3/2005 | Harris |
| 2005/0261615 A1 | 11/2005 | Weston |
| 2006/0147430 A1 | 7/2006 | Sayre et al. |
| 2007/0184034 A1 | 8/2007 | Linton |
| 2007/0193578 A1 | 8/2007 | Linton et al. |
| 2007/0209668 A1 | 9/2007 | Linton |
| 2012/0073577 A1 | 3/2012 | Linton |
| 2012/0080036 A1 | 4/2012 | Linton |
| 2015/0150742 A1 | 6/2015 | Linton et al. |

FOREIGN PATENT DOCUMENTS

| | | |
|---|---|---|
| JP | 60-232178 | 11/1985 |
| JP | 08-154982 A | 6/1996 |
| JP | 2003-310800 | 11/2003 |
| JP | 2004-202156 | 7/2004 |
| WO | WO 2004/047710 | 6/2004 |
| WO | WO 2005/035068 | 4/2005 |
| WO | WO 2008/030265 A2 | 3/2008 |

OTHER PUBLICATIONS

Schobersberger et al, 2003 Eur J Appl Physiol. 88:506-514.*
Blake et al, 2004. Diabetes. 53: 2095-2100.*
Office Action for U.S. Appl. No. 11/672,934, mailed on Aug. 17, 2009.
Final Office Action for U.S. Appl. No. 11/672,934, mailed on Jul. 21, 2010.
Arver et al., "Serum dihydrotestosterone and testosterone concentrations in human immunodeficiency virus-infected men with and without weight loss," J. Andrology, 20(5):611-618 (1999).
Bhasin et al, "Testosterone therapy in adult men with androgen deficiency syndromes: an endocrine society clinical practice guideline," J. Clin. Endocrin. & Metab., 91(6):1995-2010 (2006).

(Continued)

*Primary Examiner* — Zachary Howard

(57) ABSTRACT

Methods for administering pressure changes to a user for the treatment and prevention of diseases and conditions are disclosed herein. Methods of administering Cyclic Variations in Altitude Conditioning Sessions (CVAC Session(s)) for the treatment of steroidogenesis, steroid levels, and treatment of serum lipid levels are disclosed herein. Also disclosed herein are methods of administering CVAC Session(s) for the treatment of steroid levels and steroidogenesis associated with HIV infection.

19 Claims, 32 Drawing Sheets

(56) References Cited

OTHER PUBLICATIONS

Bärtsch, P. et al., "Contemporary Reviews in Cardiovascular Medicine: Effect of Altitude on the Heart and the Lungs," Circulation: Journal of the American Heart Association, Nov. 6, 2007, vol. 116, pp. 2191-2202.
Blackmore, DG, et al., "Exercise Increases Neural Stem Cell No. In a Growth Hormone-Dependent Manner, Augmenting the Regenerative Response in Aged Mice," Stem Cells 27:2044-2052 (2009).
CVAC, "Company Fact Sheet," Feb. 3, 2006.
CVAC Systems Product Profile, "Enhancing Performance Beyond High-Altitude Acclimatization," 2006, 1 page.
Dai, Guohao, et al., "Endothelial nitric oxide production during in vitro simulation of external limb compression," Am. J. Physiol. Heart Circ. Physiol. 282: H2066-H2075 (Feb. 14, 2002).
Eldred, S., "Mayo Clinic's Newest Lab: Mount Everest," [online] Apr. 17, 2012. [retrieved from the internet on Nov. 5, 2014]. Retrieved from the internet: http://news.discovery.com/adventure/mayo-clinic-mt-everest-120417.htm.
Facchini, F. S. et al., "Insulin resistance as a predictor of age-related diseases," J. Clin. Endocrinol. & Metab., 86(8):3574-3578 (2001).
Halliwill, J. R. et al., "Postexercise hypotension and sustained postexercise vasodilation: what happens after we exercise?" Experimental Physiology 98:1 (2013) pp. 7-18.
Hooper, J., "Building the New Super Athlete," Men's Journal, Aug. 2013, 7 pages.
Huijberts, M. et al., "Advanced glycation end products and diabetic foot disease," Diabetes/Metabolism Research and Reviews 2008, vol. 24 (Suppl 1) pp. S19-S24.
Jákli, A. et al, "Piezoelectricity of phospholipids: A possible mechanism for mechano-, and magneto-receptions in biology," electronic-Liquid Crystal Communications, Apr. 10, 2007, 8 pages.
Katayama, K. et al., "Intermittent Hypoxia Improves Endurance Performance and Submaximal Exercise Efficiency," High Altitude Medicine & Biology, 2003, vol. 4, No. 3, pp. 291-304.
Kiger, P., "Why is Dr. Phil Inside a Pod?," [online] Sep. 10, 2013, [retrieved from the internet on Nov. 5, 2014]. Retrieved from the internet: http://blog.aarp.org/2013/09/10/why-is-dr-phil-inside-a-pod/.
Kirsh, K.A. et al., "Erythropoietin as a volume-regulating hormone: an integrated view." Semin. Nephrol., 25(6):388-391 (Nov. 2005), Abstract.
Kronenberg, G., "Physical exercise prevents age-related decline in precursor cell activity in the mouse dentate gyrus," Neurobiology Aging, Oct. 2006, vol. 27, No. 10, p. 1505-1513, Abstract.
Kupelian, V. et al., "Low sex hormone-binding globulin, total testosterone, and symptomatic androgen deficiency are associated with development of the metabolic syndrome in nonobese men," J. Clin. Endocdr. & Metabol., 91(3):843-850 (Mar. 2006).
Little, J. et al., "A practical model of low-volume high-intensity interval training induces mitochondrial biogenesis in human skeletal muscle: potential mechanisms," The Journal of Physiology, 2010, vol. 588, pp. 1011-1022.
Mayo News Releases "Mayo Clinic Studies Climbers on Everest to Help Heart Patients at Home," [online] Mar. 22, 2012. [retrieved from the internet on Nov. 5, 2014]. Retrieved from the internet: http://newsnetwork.mayoclinic.org/discussion/mayo-clinic-studies-climbers-on-everest-to-help-heart-.
Nisoli, Enzo, "Mitochondrial Biogenesis in Mammals: The Role of Endogenous Nitric Oxide," Science 299(5608): 896-899 (2003).
SENS Research Foundation's AGE-Breaker Research Programs [online], Mar. 8, 2013, [retrieved on Nov. 5, 2014]. Retrieved from Internet: https://www.fightaging.org/archives/2013/03/sens-research-foundations-age-breaker-research-programs.php.
Serebrovskaya, T., "Intermittent Hypoxia Research in the Former Soviet Union and the Commonwealth of Independent States: History and Review of the Concept and Selected Applications," High Altitude Medicine & Biology, 3(2):205-221 (2002).

Siebenmann, C. et al., "'Live high-train low' using normobaric hypoxia: a double-blinded, placebo-controlled study," J Appl Physiol 112: 106-117, 2012.
Song, Hong-jun, et al. "Neural stem cells from adult hippocampus develop essential properties of functional CNS neurons," Nature Neuroscience, vol. 5, No. 5 (May 2002).
Takagi, H. et al., "Hypoxia Upregulates Glucose Transport Activity Through an Adenosine-Mediated Increase of GLUT1 Expression in Retinal Capillary Endothelial Cells", Diabetes, 47(9):1480-1488 (1998). Abstract.
University of Illinois at Urbana-Champaign, "Exercise triggers stem cells in muscle." ScienceDaily, Feb. 6, 2012. <www.sciencedaily.com/releases/2012/02/120206143944.htm>.
Valdez, L. et al., "Mitochondrial metabolic states and membrane potential modulate mtNOS activity," Biochimica et Biophysica Acta 1757 (2006) pp. 166-172.
Valero, M. Carmen, et al. "Eccentric exercise facilitates mesenchymal stem cell appearance in skeletal muscle," PLoS One 7(1) (Jan. 11, 2012).
Wang, S., "What Everest Teaches About Disease," [online] May 29, 2012, [retrieved from the internet on Nov. 5, 2014]. Retrieved from the internet: http://online.wsj.com/article/SB10001424052702304707604577424493732692180.html.
Winkelmayer, W. C. et al., "Altitude and all-cause mortality in incident dialysis patients," JAMA, 301(5):508-512 (2009).
Wu, Chih-Wei, et al., "Exercise enhances the proliferation of neural stem cells and neurite growth and survival of neuronal progenitor cells in dentate gyrus of middle-aged mice" J. Appl Physiol. 105(5): 1585-94 (Nov. 2008).
Yoshikawa, T. et al., "Decrease in serum levels of advanced glycation end-products by short-term lifestyle modification in non-diabetic middle-aged females," Med Sci Monit, 2009, 15(6) PH65-73.
PTO-892, Notice of References Cited, from U.S. Appl. No. 10/659,997, Part of Paper No. 20070628.
International Search Report and Written Opinion for International Application No. PCT/US2004/21987 mailed Mar. 29, 2007.
Examiner's Report for Australian Patent Application No. 2007293561, mailed on Feb. 13, 2012.
Office Action for Chinese Patent Application No. 200780010115.7, dated Mar. 26, 2010; 7 pages.
Office Action for Chinese Patent Application No. 200780010115.7, dated Apr. 1, 2011.
Office Action for Chinese Patent Application No. 200780010115.7, dated Feb. 1, 2012.
Office Action for European Patent Application No. 07852349.5, dated Jan. 5, 2011; 4 pages.
Office Action for Korean Patent Application No. 10-2008-7021948, mailed on Aug. 29, 2013.
Office Action for U.S. Appl. No. 11/672,933, mailed on Jan. 16, 2009.
Final Office Action for U.S. Appl. No. 11/672,933, mailed on Jul. 24, 2009.
Office Action for U.S. Appl. No. 11/672,933, mailed on Dec. 29, 2011.
International Search Report for International Application No. PCT/US2007/003524, mailed on Sep. 8, 2008.
Written Opinion for International Application No. PCT/US2007/003524, mailed on Sep. 8, 2008.
Office Action for U.S. Appl. No. 11/672,937, mailed on Aug. 27, 2009.
Office Action for U.S. Appl. No. 11/672,937, mailed on Jul. 30, 2010.
Office Action for U.S. Appl. No. 11/672,937, mailed on Apr. 7, 2011.
Final Office Action for U.S. Appl. No. 13/011,058, mailed on Jun. 19, 2014.
Office Action for Australian Patent Application No. 2008219374, mailed on Jul. 16, 2012.
Office Action for Canadian Patent Application No. 2,679,134, mailed on Jul. 28, 2014.
Supplementary European Search Report for European Patent Application No. EP 08730679, dated Nov. 23, 2011.
Office Action for European Patent Application No. 08730679.1, mailed on Sep. 4, 2012.
Office Action for Korean Patent Application No. 10-2009-7020178, dated Jun. 20, 2011.

(56) References Cited

OTHER PUBLICATIONS

Office Action for Korean Patent Application No. 10-2009-7020178, dated Mar. 29, 2012.
International Search Report for International Application No. PCT/US2008/054923, mailed Aug. 1, 2008.
Office Action for U.S. Appl. No. 13/213,982, mailed on Jul. 2, 2013.
International Search Report for International Application No. PCT/US2008/056999, mailed Aug. 18, 2008.
Abidia et al., "The Role of Hyperbaric Oxygen Therapy in Ischaemic Diabetic Lower Extremity Ulcers: a Double-blind Randomised-controlled Trial," Eur. J. Vasc. Endovasc. Surg., vol. 25, pp. 513-518 (2003).
Balestra et al., "Serum erythropoietin levels in healthy humans after a short period of normobaric and hyperbaric oxygen breathing: the "normobaric oxygen paradox"," Journal of Applied Physiology, vol. 100, pp. 512-518 (2006).
Beidleman et al., "Substrate oxidation is altered in women during exercise upon acute altitude exposure," Medicine & Science in Sports & Exercise 34(3):430-437 (2002).
Benelli, L., et al., "Endermologie: humoral repercussions and estrogen interaction," Aesthetic Plast. Surg., 23(5):312-315 (1999).
Bosco, C. et al., "Hormonal responses to whole-body vibration in men," Eur. J. Appl. Physiol., 81:449-454 (2000).
Boyanov et al., "Testosterone supplementation in men with type 2 diabetes, visceral obesity and partial androgen deficiency," The Aging Male, 6( 1): 1-7 (2003).
Brubaker et al., "Adventure Travel and Type I Diabetes: The Complicating Effects of High Altitude," Diabetes Care 28(10):2563-2572 (2005).
Chiu, L. L. et al., "Effect of prolonged intermittent hypoxia and exercise training on glucose tolerance and muscle GLUT4 protein expression in rats," J. Biomedical Sci., 11:838-846 (2004).
"CVAC Coupon," CVAC Advertisement, approximately Aug. 2002, San Diego CA.
CVAC Systems What's New [online] Dec. 1, 2002 [retrieved on Jun. 28, 2007]. Retrieved from Internet: http://web.archive.orgLweb/20021201231932/cvacsystems.comlWhat's+New.htm.
CVAC Systems What is CVAC? [online]. Dec. 1, 2002 [retrieved on Jun. 28, 2007]. Retrieved from Internet: http://web.archive.org/web/20021201230242/cvacsystems.comlWhat+is+CVAC.htm.
CVAC Systems Background/Development [online]. Dec. 1, 2002 [retrieved on Jun. 28, 2007]. Retrieved from Internet: http://web.archive.org/web/20021201191441lcvacsystems.comiBackground.htm.
CVAC Systems Frequently Asked Questions [online]. Dec. 1, 2002 [retrieved on Jun. 28, 2007]. Retrieved from the Internet: http://web.archive. org. web/20021201230602/cvacsystems.comlCV AC+ F AQ.htm.
CVAC Systems Testimonials [online]. Feb. 14, 2003 [retrieved on Jun. 28, 2007]. Retrieved from the Internet: http:web.archive.org/web200302142314111 cvacsystems.com/testimonials.htm.
CVAC Systems Art [online]. Feb. 3, 2003 [retrieved on Jun. 28, 2007]. Retrieved from the Internet: http://web. archive. org/web/2003 0203 5 5 847/ cvacsysterns.comltestimonialsart.htm.
Ding, X. M. et al., "Neuroprotective effect of exogenous vascular endothelial growth factor on rat spinal cord neurons in vitro hypoxia," Chin. Med. J. (Engl), 118(19):1644-1650 (2005).
Eckardt, K. U. et al. "Regulation of erythropoietin production," Eur. J. Clin. Invest., 35 (Supp. 3):13-19, (2005).
Eid, T. et al., "Recombinant human erythropoietin for neuroprotection: what is the evidence?," Clin. Breast Cancer, 3 Suppl. 3:S109-S115, Dec. 2002.
Elton, S., "CVAC: The Next Wave in Altitude Training," http://www.trinewbies.com, cited on http://web.archive.org between Jun. 5, 2002 and Aug. 6, 2002.
Fuller, D. et al., "Synaptic Pathways to Phrenic Motoneurons Are Enhanced by Chronic Intermittent Hypoxia after Cervical Spinal Cord Injury," J. Neurosci., 23(7):2993-3000, Apr. 1, 2003.

Golder, F. J. et al., "Spinal synaptic enhancement with acute intermittent hypoxia improves respiratory function after chronic cervical spinal cord injury," J. Neurosci. 25(11):2925-32, Mar. 16, 2005.
Grinspoon, S., "Androgen deficiency and HIV infection," Clin. Infect. Diseases, 41:1804-1805 (2005).
Gutsaeva, D. R. et al., "Transient hypoxia stimulates mitochondrial biogenesis in brain subcortex by a neuronal nitric oxide synthase-dependent mechanism," The Journal of Neuroscience, 28(9):2015-2024 (2008).
Heinicke, K. et al., "Long-term exposure to intermittent hypoxia results in increased hemoglobin mass, reduced plasma volume, and elevated erythropoietin plasma levels in man," Eur. J. Appl. Physiol., 88(6):535-43 (2003).
Herbst, K. L., et al., "Pilot study: rapidly cycling hypobaric pressure improves pain after 5 days in adiposis dolorosa", Journal of Pain Research 2010:3 147-153.
Hetzler, R. K., et al., "The Effect of Dynamic Intermittent Hypoxic Conditioning on Arterial Oxygen Saturation", Wilderness and Environmental medicine, vol. 20, 2009, p. 26-32.
Hu et al., "Comparisons of serum testosterone and corticosterone between exercise training during normoxia and hypobaric hypoxia in rats," Eur. J. Applied Physiol. 78(5):417-421 (1998) (Abstract).
"Introducing CVAC," CVAC press release; approximately Jan. 2002, San Diego, CA.
"Introducing the CVAC Process,", CVAC press release, approximately Nov. 2001, San Diego CA.
Kanagy et al., "Role of Endothelin in Intermittent Hypoxia-Induced Hyertension," Hypertension. vol. 37, pp. 511-515 (2001).
Kiernan, T. J. et al., "Effect of enhanced external counterpulsation on circulating CD34+ progenitor cell subsets," International Journal of Cardiology (2010), doi:10.1016/j.ijcard.2010.08.020.
Kiraly, M. A. et al., "The effect of exercise on hippocampal integrity: review of recent research," Int. J. Psychiatry Med., 35(1):75-89 (2005).
Kirby, M., "Negative pressure wound therapy", The British Journal of Diabetes and Vascular Disease, vol. 7, Issue 5, Sep./Oct. 2007; p. 230-234.
Linton, C., "Kiosk Rental Letter," Letter, approximately May 2002, San Diego CA.
Makley, J. T. et al., "The Effect of Reduced Barometric Pressure on Fracture Healing in Rats", The Journal of Bone and Joint Surgery, vol. 49-A, No. 5, Jul. 1967; p. 903-914.
Marquez, J. L. et al., "Cyclic Hypobaric Hypoxia Improves Markers of Glucose Metabolism in Middle-Aged Men", High Altitude Medicine & Biology, vol. 14, No. 3, 2013; p. 263-272.
Morino, K. et al., "Reduced mitochondrial density and increased IRS-1 serine phosphorylation in muscle of insulin-resistant offspring of type 2 diabetic parents," The Journal of Clinical Investigation, 115(12):3587-3593 (2005).
"New & Exciting Adventure in Exercise," CVAC Press Release, Approximately Oct. 2001, San Diego CA.
Pavan et al., "Metabolic and Cardiovascular Parameters in Type I Diabetes at Extreme Altitude," Med. Sci. Sports Exerc. 36(8):1283-1289 (2004).
Reid, W., "Device Enhances Performances for Local Athletes," http://www.SignOnSanDiego.com, Aug. 25, 2002.
Rodriguez et al., "Erythropoietin acute reaction and haematological adaptations to short, intermittent hypobaric hypoxia", 2000. Eur J Appl Physiol. 82: 170-177.
Schmidt et al, "Effects of Intermittent Exposure to High Altitude on Blood Volume and Erythropoietin Activity," 2002. High Altitude Medicine & Biology. 3(3): 167-176).
Sen, C. K., "Wound healing essentials: Let there be oxygen", Wound Repair and Regeneration, vol. 17, 2009; pp. 1-18.
Sharp, F. et al., "Hypoxic Preconditioning Protects against Ischemic Brain Injury," NeuroRx: J. Am. Soc. Exp. Neuro., vol. 1:26-25 (2004).
Singh et al., "High Variability of Glycated Hemoglobin Concentrations in Patients with IDDM Followed Over 9 Years," Diabetes Care 20(3):306-308 (1997).
Tin'kov et al., "Effects of intermittant hypobaric hypoxia on blood lipid concentrations in male coronary heart disease patients," High Altitude Medicine & Biology, 3(3):277-282 (2002).

(56) References Cited

OTHER PUBLICATIONS

Viscor, G. et al., "Combined intermittent hypoxia and surface muscle electrostimulation as a method to increase peripheral blood progenitor cell concentration," Journal of Translational Medicine, 7:91-96 (2009).

Xiaowei, H. et al., "The experimental study of hypoxia-inducible factor-1 alpha and its target genes in spinal cord injury," Spinal Cord, 44(1):35-43, Jan. 2006.

International Search Report and Written Opinion for International Application No. PCT/US2015/056031, mailed Feb. 2, 2016.

Miller et al., "Cerebral protection by hypoxic preconditioning in murine modal of focal ischemia-perfusion," Neuroreport, vol. 12, No. 8, Jun. 13, 2001.

Romanovskii et al., "Preconditioning Hypobaric Hypoxia Prevents Anoxia-Induced Inhibition of Generation of Focal Potentials in Slices of Olfactory Cortex from Rat Brain," Bull. Exp. Biol. and Med., vol. 6, pp. 1154-1156, Dec. 2001.

Kaplan, D., "Company plugs the power of the pod," Sports Business Journal, Jan. 5, 2015, 2 pages.

Alexander, B., "The Secret Science of Novak Djokovic's Training Pod," Outside, [online] Feb. 20, 2015. [retrieved from the internet on Feb. 24, 2015]. Retrieved from the internet: http://www.outsideonline.com/outdoor-adventure/science/Will-the-CVAC-Pod-Change-the-Way-Athletes-Train.html.

Peng, Y., et al, "Effect of two paradigms of chronic intermittent hypoxia on carotid body sensory activity," J Appl Physiol vol. 96, Mar. 2004, pp. 1236-1242.

Van Liere, E.J., et al., "Differences in Cardiac Hypertrophy in Exercise and in Hypoxia," Circulation Research, vol. 16, Mar. 1965, pp. 244-248.

\* cited by examiner

| Subject | Age | Sex | CVAC Exposure Summer 2007 | CVAC Exposure Fall 2007 | Total chol. | Tri. | HDL | VLDL | LDL | Total chol. | Tri. | HDL | VLDL | LDL | Total chol. | Tri. | HDL | VLDL | LDL |
|---|---|---|---|---|---|---|---|---|---|---|---|---|---|---|---|---|---|---|---|
| S-1 | 45 | M | None | Sham | 209 | 224 | 43 | 45 | 121 | 193 | 289 | 41 | 58 | 94 | -16 | 65 | -2 | 13 | -27 |
| S-3 | 70 | M | None | CVAC | 165 | 107 | 50 | 21 | 94 | 166 | 84 | 47 | 17 | 102 | 1 | -23 | -3 | -4 | 8 |
| S-6 | 25 | F | None | CVAC | 140 | 64 | 57 | 13 | 70 | 190 | 70 | 66 | 14 | 110 | 50 | 6 | 9 | 1 | 40 |
| M-9 | 37 | M | CVAC | CVAC | 158 | 36 | 49 | 7 | 102 | 164 | 66 | 40 | 13 | 111 | 6 | 30 | -9 | 6 | 9 |
| M-18 | 28 | M | CVAC | CVAC | 177 | 90 | 59 | 18 | 100 | 165 | 96 | 51 | 19 | 95 | -12 | 6 | -8 | 1 | -5 |
| M-23 | 60 | M | Sham | CVAC | 201 | 132 | 42 | 26 | 133 | 214 | 164 | 50 | 33 | 131 | 13 | 32 | 8 | 7 | -2 |
| M-14 | 49 | M | None | None | 187 | 63 | 65 | 13 | 109 | 173 | 76 | 52 | 15 | 106 | -14 | 13 | -13 | 2 | -3 |

FIG. 2

| Subject | Age | Sex | CVAC Exposure Summer 2007 | CVAC Exposure Fall 2007 | TOTAL SERUM TESTOSTERONE SEPT. TO DEC. 2007 | | | | SERUM FREE TESTOSTERONE SEPT. TO DEC. 2007 | | | | RATIO OF SERUM FREE TESTOSTERONE TO TOTAL TESTOSTERONE SEPT. TO DEC. 2007 | | | |
|---|---|---|---|---|---|---|---|---|---|---|---|---|---|---|---|---|
| | | | | | Sept. | Dec. | Diff. | % Diff. | Sept. | Dec. | Diff. | % Diff. | Sept. | Dec. | Diff. | % Diff. |
| S-1 | 45 | M | None | Sham | 355 | 316 | -39 | -11% | 15.97 | 15.52 | -0.45 | -3% | 4.5 | 4.91 | 0.41 | 9% |
| S-3 | 70 | M | None | CVAC | 573 | 746 | 173 | 30% | 15.64 | 14.55 | -1.09 | -7% | 2.73 | 1.95 | -0.78 | -29% |
| S-6 | 25 | F | None | CVAC | 43 | 70 | 27 | 63% | 0.7 | 1.29 | 0.59 | 84% | 1.63 | 1.84 | 0.21 | 13% |
| M-9 | 37 | M | CVAC | CVAC | 365 | 566 | 201 | 55% | 10.57 | 23.26 | 12.69 | 120% | 2.97 | 4.11 | 1.14 | 38% |
| M-18 | 28 | M | CVAC | CVAC | 656 | 799 | 143 | 22% | 30.57 | 31.8 | 1.23 | 4% | 4.66 | 3.98 | -0.68 | -15% |
| M-23 | 60 | M | Sham | CVAC | 475 | 505 | 30 | 6% | 10.5 | 15.4 | 4.9 | 47% | 2.21 | 3.05 | 0.84 | 38% |
| M-14 | 49 | M | None | None | 866 | 841 | -25 | -3% | 17.06 | 17.07 | 0.01 | 0% | 1.97 | 2.03 | 0.06 | 3% |

FIG. 3

COMBINATION PRESSURE THERAPY

CROSS-REFERENCE

This application claims priority to and the benefit under 35 U.S.C. §371 of International patent application No. PCT/US2008/054923, entitled "Combination Pressure Therapy for Treatment of Serum Lipid Levels, Steroid Levels, and Steroidogenesis," filed Feb. 25, 2008, which claims priority to and the benefit of U.S. Provisional Application No. 60/891,696, filed Feb. 26, 2007, U.S. Provisional Application No. 60/953,973, filed Aug. 3, 2007, U.S. Provisional Application No. 60/953,972, filed Aug. 3, 2007, and U.S. Provisional Application No. 61/025,272, filed Jan. 31, 2008, which applications are incorporated herein by reference.

FIELD OF THE INVENTION

The invention relates to the use of air pressure therapy for the treatment and prevention of diseases and conditions that benefit from hypoxic conditioning and/or total body vasopneumatic compression.

BACKGROUND OF THE INVENTION

Hyperlipidemia, hyperlipoproteinemia or dyslipidemia is the presence of elevated or abnormal levels of lipids and/or lipoproteins in the blood. Lipids (fatty molecules) are transported through and around the body in the blood. Easily recognizable categories of these lipids include low-density lipoproteins, high-density lipoproteins, and cholesterol. Lipid and lipoprotein abnormalities are extremely common in the general population, and are regarded as a highly modifiable risk factor for cardiovascular disease due to the influence of cholesterol, one of the most clinically relevant lipid substances, on atherosclerosis. Hyperlipidemia becomes most seriously symptomatic when interfering with the coronary circulation supplying the heart or cerebral circulation supplying the brain, and is considered the most important underlying cause of strokes, heart attacks, various heart diseases including congestive heart failure and most cardiovascular diseases in general. Atheroma in the arm, or more often leg, arteries often produces decreased blood flow and is called Peripheral artery occlusive disease (PAOD).

Cholesterol is also the main building block of in the process of steroidogenesis. Steroidogenesis involves the synthesis of steroid compounds, including the hormones testosterone and estrogen, as well as mineralocorticoids and glucocorticoids. Dysregulation of steroid and hormone synthesis results in detrimental effects on men and women. For example, dysregulation of testosterone can result in changes in body composition, increases in fat mass, and decreases in lean body mass. [Kupelian, V. et al., *Low Sex Hormone-Binding Globulin, Total Testosterone, and Symptomatic Androgen Deficiency are Associated with Development of the Metabolic Syndrome in Non-Obese Men*, J. Clin. Endocdr. & Metabol., 91(3): 843-50 (2007).] Similar problems occur in women, and hormone dysregulation related to estrogens and menopause is well documented. Thus, steroidogenesis and hormone dysregulation are a continuing health problem.

Additionally, infection with the human immunodeficiency virus ("HIV") can have complications such as dysregulation of steroidogenesis. Androgen deficiency is known to be prevalent among HIV-infected men with low weight and wasting. Initial estimates demonstrated that androgen deficiency occurs in 50% of men with AIDS-related wasting, and more recently has been shown to be present in, on average, 20% of men who receive highly active antiretroviral therapy ("HAART"). Similarly, testosterone levels are reduced among women with HIV disease as compared with levels in age- and sex-matched control subjects. [Steven Grinspoon, *Androgen Deficiency and HIV infection*, Clin. Infect. Diseases, 41:1804-05 (2005).]

Abnormalities in the process of steroidogenesis (including the modulation of steroid levels) are commonly treated with pharmaceuticals. Examples of such pharmaceuticals include, but are not limited to, supplemental testosterone, estrogens, and other hormones. There is a need for alternative therapies for the modulation of steroidogenesis and serum lipid levels. There is also a need for modulation of steroid levels in HIV infected individuals.

SUMMARY OF THE INVENTION

The present invention provides for a method of administering pressure changes to a user for the treatment of cholesterol and lipid levels. The present invention further provides for a method of administering pressure changes to a user for the treatment of steroid levels. Treatment as used herein includes application of the disclosed methodologies for prevention, prophylactic treatment, current treatment, amelioration, and recovery of the aforementioned conditions. Treatment further includes modulation of the levels, positively or negatively, serum lipids including but not limited to cholesterol, low density lipoproteins (LDL), high density lipoproteins (HDL), as well as steroid levels including but not limited to androgens, estrogens, progestogens, mineralocorticoids, and glucocorticoids. Application of the disclosed methodologies aids in the modulation of cholesterol levels, serum lipid levels, and the process of steroidogenesis.

One aspect of the invention is the administration of one or more Cyclic Variations in Altitude Conditioning Sessions (CVAC Session(s)) for the treatment of serum lipid levels. CVAC sessions may be administered in defined intervals or at random occurrences. In an embodiment of the invention, at least one CVAC session is administered to modulate cholesterol levels. In an additional embodiment, CVAC sessions are administered to modulate LDL levels. In a further embodiment, at least one CVAC session is administered to modulate HDL levels. In some embodiments, the effect of such administrations is a lowering of cholesterol levels, LDL levels, or an increase in HDL levels.

Another aspect of the invention is the administration of one or more Cyclic Variations in Altitude Conditioning Sessions (CVAC Session(s)) for the modulation of steroidogenesis. In one embodiment, at least one CVAC session is administered for the modulation of steroidogenesis in HIV infected individuals. Non-limiting examples of steroids modulated by the administration of at least one CVAC session include testosterone, estrogen, androgens, glucocorticoids, and mineralocorticoids. In a further embodiment, CVAC sessions are administered to increase steroidogenesis while decreasing cholesterol levels. In yet a further embodiment, CVAC sessions are administered to increase steroidogenesis while cholesterol levels remain stable.

In another embodiment of the invention, physiological parameters are monitored to assess the efficacy of CVAC sessions on modulating serum lipid levels. In one embodiment, cholesterol levels in a user are measured to assess the efficacy of CVAC sessions. In another embodiment, VLDL, LDL, or HDL levels are measured. In a further embodiment, physiological parameters are monitored to assess the efficacy of CVAC sessions on modulating steroid levels in a user. In one embodiment, testosterone levels in a user are measured to assess the efficacy of CVAC sessions. In another embodiment, estrogen levels in a user are measured to assess the efficacy of CVAC sessions. In yet another embodiment, mineralcorticoids or glucocorticoids are measured. In additional embodiments, efficacy of CVAC sessions for the treatment of metabolic syndrome, diabetes, and/or insulin resistance is determined via changes in physiological markers including insulin levels, glucose tolerance, glucose transport, testosterone, or any combination thereof.

A CVAC session consists of a set of targets which are pressures found in the natural atmosphere. A CVAC session includes start and end points and more than one target which are executed between the start and end points. These targets are delivered in a precise order, and are executed in a variety of patterns including, but not limited to, cyclic, repeating, and/or linear variations. The starting points and ending points in any CVAC session are preferably the ambient pressure at the delivery site. The targets inherent in any CVAC session are connected or joined together by defined transitions. These transitions are either rises in pressure or falls in pressure, or a combination of the two. Additional targets which modulate time, temperature, or humidity are also run concurrently, sequentially, or at other intervals with the pressure targets when such additional targets and conditions are desired.

In an additional embodiment, including the aforementioned embodiments and aspects, the targets of the CVAC sessions include pressure, temperature, time, and/or humidity parameters. Parameters of targets and sessions can be customized to individual needs. In yet another embodiment of the invention, including the aforementioned embodiments and aspects, CVAC sessions are administered in combination with pharmaceutical regimens for the treatment of serum lipid levels. In still another embodiment of the invention, including the aforementioned embodiments and aspects, CVAC sessions are administered in combination with pharmaceutical regimens for the modulation of steroidogenesis. In yet another embodiment of the invention CVAC sessions are administered in combination with pharmaceutical regimens for the modulation of steroidogenesis in HIV infected individuals. Provided herein is a method of increasing weight in an HIV-infected mammal comprising administering at least one CVAC session to a mammal infected with HIV, said CVAC session having a start point, an end point and more than one target which is executed between said start point and said end point. Also provided herein is a method of increasing muscle mass in an HIV-infected mammal by administering at least one CVAC session to an HIV-infected mammal. Provided herein is a method of increasing muscle strength in an HIV-infected mammal comprising administering at least one CVAC session. In additional embodiments, weight gain, increases in muscle mass, and increases in muscle strength are obtained by the administration of at least one CVAC session that modulates testosterone levels in HIV-infected mammals. Further embodiments, including the aforementioned embodiments and aspects, include administration of CVAC sessions in combination with alternative therapies and non-pharmaceutical therapies.

Provided herein is a method of treating serum lipid levels in a mammal comprising the step of administering at least one CVAC session to a mammal, said CVAC session having a start point, an end point and more than one target which is executed between said start point and said end point.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring the efficacy of the CVAC sessions by non-invasive imaging.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring the efficacy of the CVAC sessions by non-invasive imaging.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, and further comprising the step of measuring the efficacy of the CVAC sessions by non-invasive imaging.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, and further comprising the step of measuring the efficacy of the CVAC sessions by non-invasive imaging.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and further comprising the step of measuring the efficacy of the CVAC sessions by non-invasive imaging.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, and further comprising the step of measuring the efficacy of the CVAC sessions by non-invasive imaging.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring the efficacy of the CVAC sessions by invasive imaging.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring the efficacy of the CVAC sessions by invasive imaging.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, and further comprising the step of measuring the efficacy of the CVAC sessions by invasive imaging.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, and further comprising the step of measuring the efficacy of the CVAC sessions by invasive imaging.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and further comprising the step of measuring the efficacy of the CVAC sessions by invasive imaging.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, and further comprising the step of measuring the efficacy of the CVAC sessions by invasive imaging.

Further provided herein is a method of treating serum lipid levels in a mammal comprising the step of administering at least one CVAC session to a mammal, said CVAC session having a start point, an end point and more than one target which is executed between said start point and said end point, further comprising the step of administering at least one pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of administering at least one pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, and further comprising the step of administering at least one pharmaceutical therapy.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, BDL or cholesterol and further comprising the step of measuring efficacy of CVAC sessions via changes in physiological markers wherein the physiological marker measured is selected from among VLDL, LDL, HDL, cholesterol or erythropoietin (EPO) production, and further comprising the step of administering at least one pharmaceutical therapy.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and further comprising the step of administering at least one pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, and further comprising the step of administering at least one pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, further comprising the step of administering at least one non-pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of administering at least one non-pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, and further comprising the step of administering at least one non-pharmaceutical therapy.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, and further comprising the step of administering at least one non-pharmaceutical therapy.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and further comprising the step of administering at least one non-pharmaceutical therapy.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, and further comprising the step of administering at least one non-pharmaceutical therapy.

Provided herein is a method of treating serum lipid levels in a mammal comprising the step of administering at least one CVAC session to a mammal, said CVAC session having a start point, an end point and more than one target which is executed between said start point and said end point, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring the efficacy of the CVAC sessions by non-invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring the efficacy of the CVAC sessions by non-invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, further comprising the step of measuring the efficacy of the CVAC sessions by non-invasive imaging, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, further comprising the step of measuring the efficacy of the CVAC sessions by non-invasive imaging, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, further comprising the step of measuring the efficacy of the CVAC sessions by non-invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, further comprising the step of measuring the efficacy of the CVAC sessions by non-invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring the efficacy of the CVAC sessions by invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring the efficacy of the CVAC sessions by invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, further comprising the step of measuring the efficacy of the CVAC sessions by invasive imaging, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, further comprising the step of measuring the efficacy of the CVAC sessions by invasive imaging, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, further comprising the step of measuring the efficacy of the CVAC sessions by invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, further comprising the step of measuring the efficacy of the CVAC sessions by invasive imaging, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of administering at least one pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of administering at least one pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, further comprising the step of administering at least one pharmaceutical therapy, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, further comprising the step of administering at least one pharmaceutical therapy, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, further comprising the step of administering at least one pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, further comprising the step of administering at least one pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of administering at least one non-pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of administering at least one non-pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol, further comprising the step of measuring efficacy of CVAC sessions via changes in physiological markers, further comprising the step of administering at least one non-pharmaceutical therapy, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, where the serum lipid is selected from among VLDL, LDL, HDL or cholesterol and further comprising the step of measuring efficacy of CVAC sessions via changes in physiological markers wherein the physiological marker measured is selected from among VLDL, LDL, HDL, cholesterol or erythropoietin (EPO) production, further comprising the step of administering at least one non-pharmaceutical therapy, and wherein the mammal can modulate the parameters of a session.

Also provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, further comprising the step of administering at least one non-pharmaceutical therapy, and wherein the mammal can modulate the parameters of a session.

Further provided herein is a method of treating serum lipid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, wherein the physiological marker measured is selected from among VLDL, LDL, HDL, cholesterol or erythropoietin (EPO) production, and further comprising the step of administering at least one non-pharmaceutical therapy and wherein the mammal can modulate the parameters of a session.

Provided herein is a method of modulating steroidogenesis in a mammal comprising the step of administering at least one CVAC session to a mammal, said CVAC session having a start point, an end point and more than one target which is executed between said start point and said end point.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones.

Provided herein is a method of modulating steroid levels in a mammal comprising the step of administering at least one CVAC session to a mammal, said CVAC session having a start point, an end point and more than one target which is executed between said start point and said end point.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen.

Provided herein is a method of modulating steroidogenesis in a mammal comprising the step of administering at least one CVAC session to a mammal, said CVAC session having a start point, an end point and more than one target which is executed between said start point and said end point, and wherein the mammal is an HIV-infected mammal.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, and wherein the mammal is an HIV-infected mammal.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, and wherein the mammal is an HIV-infected mammal.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, and wherein the mammal is an HIV-infected mammal.

Provided herein is a method of modulating steroid levels in a mammal comprising the step of administering at least one CVAC session to a mammal, said CVAC session having a start point, an end point and more than one target which is executed between said start point and said end point, and wherein the mammal is an HIV-infected mammal.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, and wherein the mammal is an HIV-infected mammal.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, and wherein the mammal is an HIV-infected mammal.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, and wherein the mammal is an HIV-infected mammal.

Provided herein is a method of increasing weight in an HIV-infected mammal comprising administering at least one CVAC session to a mammal infected with HIV, said CVAC session having a start point, an end point and more than one target which is executed between said start point and said end point.

Also provided herein is method of increasing muscle mass in an HIV-infected mammal comprising administering at least one CVAC session to a mammal infected with HIV, said CVAC session having a start point, an end point and more than one target which is executed between said start point and said end point.

Further provided herein is a method of increasing muscle strength in an HIV-infected mammal comprising administering at least one CVAC session to a mammal infected with HIV, said CVAC session having a start point, an end point and more than one target which is executed between said start point and said end point.

Provided herein is a method of increasing weight in an HIV-infected mammal comprising administering at least one CVAC session to a mammal infected with HIV, said CVAC session having a start point, an end point and more than one target which is executed between said start point and said end point, and wherein the administration of at least one CVAC session modulates testosterone levels in said mammal.

Also provided herein is method of increasing muscle mass in an HIV-infected mammal comprising administering at least one CVAC session to a mammal infected with HIV, said CVAC session having a start point, an end point and more than one target which is executed between said start point and said end point, and wherein the administration of at least one CVAC session modulates testosterone levels in said mammal.

Further provided herein is a method of increasing muscle strength in an HIV-infected mammal comprising administering at least one CVAC session to a mammal infected with HIV, said CVAC session having a start point, an end point and more than one target which is executed between said start point and said end point, and wherein the administration of at least one CVAC session modulates testosterone levels in said mammal.

Provided herein is a method of increasing weight in an HIV-infected mammal comprising administering at least one CVAC session to a mammal infected with HIV, said CVAC session having a start point, an end point and more than one target which is executed between said start point and said end point, and wherein the administration of at least one CVAC session increases testosterone levels in said mammal.

Also provided herein is method of increasing muscle mass in an HIV-infected mammal comprising administering at least one CVAC session to a mammal infected with HIV, said CVAC session having a start point, an end point and more than one target which is executed between said start point and said end point, and wherein the administration of at least one CVAC session increases testosterone levels in said mammal.

Further provided herein is a method of increasing muscle strength in an HIV-infected mammal comprising administering at least one CVAC session to a mammal infected with HIV, said CVAC session having a start point, an end point and more than one target which is executed between said start point and said end point, and wherein the administration of at least one CVAC session increases testosterone levels in said mammal.

Provided herein is a method of increasing weight in an HIV-infected mammal comprising administering at least one CVAC session to a mammal infected with HIV, said CVAC session having a start point, an end point and more than one target which is executed between said start point and said end point, and further comprising the step of administering at least one pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, and further comprising the step of administering at least one pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, and further comprising the step of administering at least one pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, and further comprising the step of administering at least one non-pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, and further comprising the step of administering at least one non-pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, and further comprising the step of administering at least one non-pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, and further comprising the step of measuring efficacy of CVAC sessions via changes in physiological markers.

Also provided herein is method of increasing muscle mass in an HIV-infected mammal comprising administering at least one CVAC session to a mammal infected with HIV, said CVAC session having a start point, an end point and more than one target which is executed between said start point and said end point, and further comprising the step of measuring efficacy of CVAC sessions via changes in physiological markers.

Further provided herein is a method of increasing muscle strength in an HIV-infected mammal comprising administering at least one CVAC session to a mammal infected with HIV, said CVAC session having a start point, an end point and more than one target which is executed between said start point and said end point, and further comprising the step of measuring efficacy of CVAC sessions via changes in physiological markers.

Provided herein is a method of increasing weight in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Also provided herein is method of increasing muscle mass in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of increasing muscle strength in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of modulating steroidogenesis in a mammal comprising the step of administering at least one CVAC session to a mammal, said CVAC session having a start point, an end point and more than one target which is executed between said start point and said end point, further comprising the step of administering at least one pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, further comprising the step of administering at least one pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, further comprising the step of administering at least one pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, and further comprising the step of administering at least one pharmaceutical therapy.

Provided herein is a method of modulating steroid levels in a mammal comprising the step of administering at least one CVAC session to a mammal, said CVAC session having a start point, an end point and more than one target which is executed between said start point and said end point, further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, and further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, and further comprising the step of administering at least one pharmaceutical therapy.

Provided herein is a method of modulating steroidogenesis in a mammal comprising the step of administering at least one CVAC session to a mammal, said CVAC session having a start point, an end point and more than one target which is executed between said start point and said end point, wherein the mammal is an HIV-infected mammal, and further comprising the step of administering at least one pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, wherein the mammal is an HIV-infected mammal, and further comprising the step of administering at least one pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, wherein the mammal is an HIV-infected mammal, further comprising the step of administering at least one pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, wherein the mammal is an HIV-infected mammal, and further comprising the step of administering at least one pharmaceutical therapy.

Provided herein is a method of modulating steroid levels in a mammal comprising the step of administering at least one CVAC session to a mammal, said CVAC session having a start point, an end point and more than one target which is executed between said start point and said end point, wherein the mammal is an HIV-infected mammal, and further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, wherein the mammal is an HIV-infected mammal, and further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, wherein the mammal is an HIV-infected mammal, and further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, wherein the mammal is an HIV-infected mammal, and further comprising the step of administering at least one pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, and further comprising the step of administering at least one pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, and further comprising the step of administering at least one pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, and further comprising the step of administering at least one pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of administering at least one pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of administering at least one pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of administering at least one pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and further comprising the step of administering at least one pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and further comprising the step of administering at least one pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and further comprising the step of administering at least one pharmaceutical therapy.

Provided herein is a method of modulating steroidogenesis in a mammal comprising the step of administering at least one CVAC session to a mammal, said CVAC session having a start point, an end point and more than one target which is executed between said start point and said end point, further comprising the step of administering at least one non-pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucocorticoids, further comprising the step of administering at least one non-pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, further comprising the step of administering at least one non-pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, and further comprising the step of administering at least one non-pharmaceutical therapy.

Provided herein is a method of modulating steroid levels in a mammal comprising the step of administering at least one CVAC session to a mammal, said CVAC session having a start point, an end point and more than one target which is executed between said start point and said end point, further comprising the step of administering at least one non-pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucocorticoids, further comprising the step of administering at least one pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, and further comprising the step of administering at least one non-pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, and further comprising the step of administering at least one non-pharmaceutical therapy.

Provided herein is a method of modulating steroidogenesis in a mammal comprising the step of administering at least one CVAC session to a mammal, said CVAC session having a start point, an end point and more than one target which is executed between said start point and said end point, wherein the mammal is an HIV-infected mammal, and further comprising the step of administering at least one non-pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucocorticoids, wherein the mammal is an HIV-infected mammal, and further comprising the step of administering at least one non-pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, wherein the mammal is an HIV-infected mammal, further comprising the step of administering at least one non-pharmaceutical therapy.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, wherein the mammal is an HIV-infected mammal, and further comprising the step of administering at least one non-pharmaceutical therapy.

Provided herein is a method of modulating steroid levels in a mammal comprising the step of administering at least one CVAC session to a mammal, said CVAC session having a start point, an end point and more than one target which is executed between said start point and said end point, wherein the mammal is an HIV-infected mammal, and further comprising the step of administering at least one non-pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucocorticoids, wherein the mammal is an HIV-infected mammal, and further comprising the step of administering at least one non-pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, wherein the mammal is an HIV-infected mammal, and further comprising the step of administering at least one non-pharmaceutical therapy.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, wherein the mammal is an HIV-infected mammal, and further comprising the step of administering at least one non-pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, and further comprising the step of administering at least one non-pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, and further comprising the step of administering at least one non-pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, and further comprising the step of administering at least one non-pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of administering at least one non-pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of administering at least one non-pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of administering at least one non-pharmaceutical therapy.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and further comprising the step of administering at least one non-pharmaceutical therapy.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and further comprising the step of administering at least one non-pharmaceutical therapy.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and further comprising the step of administering at least one non-pharmaceutical therapy.

Provided herein is a method of modulating steroidogenesis in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, further comprising the step of measuring efficacy of CVAC sessions via changes in physiological markers.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, further comprising the step of measuring efficacy of CVAC sessions via changes in physiological markers.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, and further comprising the step of measuring efficacy of CVAC sessions via changes in physiological markers.

Provided herein is a method of modulating steroid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, further comprising the step of measuring efficacy of CVAC sessions via changes in physiological markers.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, and further comprising the step of measuring efficacy of CVAC sessions via changes in physiological markers.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, and further comprising the step of measuring efficacy of CVAC sessions via changes in physiological markers.

Provided herein is a method of modulating steroidogenesis in a mammal comprising the step of administering at least one CVAC session to a mammal, said CVAC session having a start point, an end point and more than one target which is executed between said start point and said end point, wherein the mammal is an HIV-infected mammal, and further comprising the step of measuring efficacy of CVAC sessions via changes in physiological markers.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, wherein the mammal is an HIV-infected mammal, and further comprising the step of measuring efficacy of CVAC sessions via changes in physiological markers.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, wherein the mammal is an HIV-infected mammal, further comprising the step of measuring efficacy of CVAC sessions via changes in physiological markers.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, wherein the mammal is an HIV-infected mammal, and further comprising the step of measuring efficacy of CVAC sessions via changes in physiological markers.

Provided herein is a method of modulating steroid levels in a mammal comprising the step of administering at least one CVAC session to a mammal, said CVAC session having a start point, an end point and more than one target which is executed between said start point and said end point, wherein the mammal is an HIV-infected mammal, and further comprising the step of measuring efficacy of CVAC sessions via changes in physiological markers.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, wherein the mammal is an HIV-infected mammal, and further comprising the step of measuring efficacy of CVAC sessions via changes in physiological markers.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, wherein the mammal is an HIV-infected mammal, and further comprising the step of measuring efficacy of CVAC sessions via changes in physiological markers.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, wherein the mammal is an HIV-infected mammal, and further comprising the step of measuring efficacy of CVAC sessions via changes in physiological markers.

Provided herein is a method of increasing weight in an HIV-infected mammal comprising administering at least one CVAC session to a mammal infected with HIV, said CVAC session having a start point, an end point and more than one target which is executed between said start point and said end point, and further comprising the step of measuring efficacy of CVAC sessions via changes in physiological markers.

Also provided herein is method of increasing muscle mass in an HIV-infected mammal comprising administering at least one CVAC session to a mammal infected with HIV, said CVAC session having a start point, an end point and more than one target which is executed between said start point and said end point, and further comprising the step of measuring efficacy of CVAC sessions via changes in physiological markers.

Further provided herein is a method of increasing muscle strength in an HIV-infected mammal comprising administering at least one CVAC session to a mammal infected with HIV, said CVAC session having a start point, an end point and more than one target which is executed between said start point and said end point, and further comprising the step of measuring efficacy of CVAC sessions via changes in physiological markers.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of measuring efficacy of CVAC sessions via changes in physiological markers.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and further comprising the step of measuring efficacy of CVAC sessions via changes in physiological markers.

Provided herein is a method of modulating steroidogenesis in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucocorticoids, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, and further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of modulating steroid levels in a mammal comprising the step of administering at least one CVAC session to a mammal, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of modulating steroidogenesis in a mammal comprising the step of administering at least one CVAC session to a mammal, said CVAC session having a start point, an end point and more than one target which is executed between said start point and said end point, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of modulating steroid levels in a mammal comprising the step of administering at least one CVAC session to a mammal, said CVAC session having a start point, an end point and more than one target which is executed between said start point and said end point, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucocorticoids, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, wherein the mammal is an HIV-infected mammal, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of increasing weight in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Also provided herein is method of increasing muscle mass in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of increasing muscle strength in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, further comprising the step of measuring efficacy of CVAC sessions via changes in physiological markers, and wherein the physiological marker measured is selected from among androgens, progestogens, estrogens, mineralcorticoids, or glucocorticoids.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, further comprising the step of measuring efficacy of CVAC sessions via changes in physiological markers, and wherein the physiological marker measured is selected from among androgens, progestogens, estrogens, mineralcorticoids, or glucocorticoids.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, further comprising the step of measuring efficacy of CVAC sessions via changes in physiological markers, and wherein the physiological marker measured is selected from among androgens, progestogens, estrogens, mineralcorticoids, or glucocorticoids.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, further comprising the step of measuring efficacy of CVAC sessions via changes in physiological markers, and wherein the physiological marker measured is selected from among androgens, progestogens, estrogens, mineralcorticoids, or glucocorticoids.

Provided herein is a method of modulating steroidogenesis in a mammal comprising the step of administering at least one CVAC session to a mammal, said CVAC session having a start point, an end point and more than one target which is executed between said start point and said end point, and wherein the mammal can modulate the parameters of a session.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucococorticoids, and wherein the mammal can modulate the parameters of a session.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, and wherein the mammal can modulate the parameters of a session.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, and wherein the mammal can modulate the parameters of a session.

Provided herein is a method of modulating steroid levels in a mammal comprising the step of administering at least one CVAC session to a mammal, said CVAC session having a start point, an end point and more than one target which is executed between said start point and said end point, and wherein the mammal can modulate the parameters of a session.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucococorticoids, and wherein the mammal can modulate the parameters of a session.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, and wherein the mammal can modulate the parameters of a session.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, and wherein the mammal can modulate the parameters of a session.

Provided herein is a method of modulating steroidogenesis in a mammal comprising the step of administering at least one CVAC session to a mammal, said CVAC session having a start point, an end point and more than one target which is executed between said start point and said end point, wherein the mammal is an HIV-infected mammal, and wherein the mammal can modulate the parameters of a session.

Further provided herein is a method of modulating steroidogenesis in a mammal comprising the step of administering at least one CVAC session to a mammal, said CVAC session having a start point, an end point and more than one target which is executed between said start point and said end point, where the steroid produced by steroidogenesis is selected from among androgens, progestogens, estrogens, mineralocorticoids, and glucocorticoids, wherein the mammal is an HIV-infected mammal, and wherein the mammal can modulate the parameters of a session.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is testosterone, wherein the mammal is an HIV-infected mammal, and wherein the mammal can modulate the parameters of a session.

Further provided herein is a method of modulating steroidogenesis in a mammal comprising the step of administering at least one CVAC session to a mammal, said CVAC session having a start point, an end point and more than one target which is executed between said start point and said end point, wherein the steroid produced by steroidogenesis is selected from among estradiols, estriols, and estrones, wherein the mammal is an HIV-infected mammal, and wherein the mammal can modulate the parameters of a session.

Provided herein is a method of modulating steroid levels in a mammal comprising the step of administering at least one CVAC session to a mammal, said CVAC session having a start point, an end point and more than one target which is executed between said start point and said end point, wherein the mammal is an HIV-infected mammal, and wherein the mammal can modulate the parameters of a session.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is selected from among androgens, progestogens, estrogens, mineralocorticoids, and glucocorticoids, wherein the mammal is an HIV-infected mammal, and wherein the mammal can modulate the parameters of a session.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is testosterone, wherein the mammal is an HIV-infected mammal, and wherein the mammal can modulate the parameters of a session.

Further provided herein is a method of modulating steroid levels in a mammal comprising the step of administering at least one CVAC session to a mammal, said CVAC session having a start point, an end point and more than one target which is executed between said start point and said end point, wherein the steroid modulated is an estrogen, wherein the mammal is an HIV-infected mammal, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session modulates testosterone levels in said mammal, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, wherein the administration of at least one CVAC session increases testosterone levels in said mammal, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, further comprising the step of administering at least one pharmaceutical therapy, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, further comprising the step of administering at least one pharmaceutical therapy, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, further comprising the step of administering at least one pharmaceutical therapy, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, further comprising the step of administering at least one non-pharmaceutical therapy, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, further comprising the step of administering at least one non-pharmaceutical therapy, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, further comprising the step of administering at least one non-pharmaceutical therapy, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, and wherein the mammal can modulate the parameters of a session.

Provided herein is a method of increasing weight in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, wherein the physiological marker measured is selected from among androgens, progestogens, estrogens, mineralcorticoids, or glucocorticoids, and wherein the mammal can modulate the parameters of a session.

Also provided herein is method of increasing muscle mass in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, wherein the physiological marker measured is selected from among androgens, progestogens, estrogens, mineralcorticoids, or glucocorticoids, and wherein the mammal can modulate the parameters of a session.

Further provided herein is a method of increasing muscle strength in an HIV-infected mammal comprising administering at least one CVAC session to a mammal infected with HIV, said CVAC session having a start point, an end point and more than one target which is executed between said start point and said end point, further comprising the step of measuring efficacy of CVAC sessions via changes in physiological markers, wherein the physiological marker measured is selected from among androgens, progestogens, estrogens, mineralcorticoids, or glucocorticoids, and wherein the mammal can modulate the parameters of a session.

Also provided herein is a method of treating metabolic syndrome in a mammal comprising the step of modulating steroid levels in said mammal by administering at least one CVAC session, said CVAC session having a start point, an end point and more than one target which is executed between said start point and said end point.

Further provided herein is a method of treating type-2 diabetes in a mammal comprising the step of modulating steroid levels in said mammal by administering at least one CVAC session, said CVAC session having a start point, an end point and more than one target which is executed between said start point and said end point.

Further provided herein is a method of treating insulin resistance in a mammal comprising the step of modulating steroid levels in said mammal by administering at least one CVAC session, said CVAC session having a start point, an end point and more than one target which is executed between said start point and said end point.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid level is increased.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid level is increased.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid level is increased.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid is testosterone.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid is testosterone.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid is testosterone.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid is testosterone, further comprising the step of measuring efficacy of CVAC sessions via changes in physiological markers.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid is testosterone, further comprising the step of measuring efficacy of CVAC sessions via changes in physiological markers.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid is testosterone, and further comprising the step of measuring efficacy of CVAC sessions via changes in physiological markers.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers and wherein the physiological marker measured is an androgen, a progestogen, an estrogen, a mineralocorticoid, or a glucocorticoid.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers and wherein the physiological marker measured is an androgen, a progestogen, an estrogen, a mineralocorticoid, or a glucocorticoid.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid is testosterone, further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid is testosterone, further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid is testosterone, and further comprising the step of measuring efficacy of CVAC sessions via changes in physiological markers and wherein the physiological marker measured is an androgen, a progestogen, an estrogen, a mineralocorticoid, or a glucocorticoid.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers and wherein the physiological marker measured is an androgen, a progestogen, an estrogen, a mineralocorticoid, or a glucocorticoid.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers and wherein the physiological marker measured is an androgen, a progestogen, an estrogen, a mineralocorticoid, or a glucocorticoid.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers and wherein the physiological marker measured is an androgen, a progestogen, an estrogen, a mineralocorticoid, or a glucocorticoid.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers and wherein the physiological marker measured is insulin, glucose tolerance, glucose transport, testosterone, or any combination thereof.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers and wherein the physiological marker measured is insulin, glucose tolerance, glucose transport, testosterone, or any combination thereof.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of measuring efficacy of CVAC sessions via changes in physiological markers and wherein the physiological marker measured is insulin, glucose tolerance, glucose transport, testosterone, or any combination thereof.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers and wherein the physiological marker measured is insulin, glucose tolerance, glucose transport, testosterone, or any combination thereof.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers and wherein the physiological marker measured is insulin, glucose tolerance, glucose transport, testosterone, or any combination thereof.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid level is increased, further comprising the step of measuring efficacy of CVAC sessions via changes in physiological markers and wherein the physiological marker measured is insulin, glucose tolerance, glucose transport, testosterone, or any combination thereof.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the steroid is testosterone, further comprising the step of measuring efficacy of CVAC sessions via changes in physiological markers and wherein the physiological marker measured is insulin, glucose tolerance, glucose transport, testosterone, or any combination thereof.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the steroid is testosterone, further comprising the step of measuring efficacy of CVAC sessions via changes in physiological markers and wherein the physiological marker measured is insulin, glucose tolerance, glucose transport, testosterone, or any combination thereof.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the steroid is testosterone, and further comprising the step of measuring efficacy of CVAC sessions via changes in physiological markers and wherein the physiological marker measured is insulin, glucose tolerance, glucose transport, testosterone, or any combination thereof.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers and wherein the physiological marker measured is insulin, glucose tolerance, glucose transport, testosterone, or any combination thereof.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one pharmaceutical therapy, and further comprising the step of measuring efficacy of CVAC sessions via changes in physiological markers and wherein the physiological marker measured is insulin, glucose tolerance, glucose transport, testosterone, or any combination thereof.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers and wherein the physiological marker measured is insulin, glucose tolerance, glucose transport, testosterone, or any combination thereof.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers and wherein the physiological marker measured is insulin, glucose tolerance, glucose transport, testosterone, or any combination thereof.

Further provided herein is a method of treating insulin resistance in a mammal comprising the step of modulating steroid levels in said mammal by administering at least one CVAC session, said CVAC session having a start point, an end point and more than one target which is executed between said start point and said end point, further comprising the step of administering at least one non-pharmaceutical therapy, and further comprising the step of measuring efficacy of CVAC sessions via changes in physiological markers and wherein the physiological marker measured is insulin, glucose tolerance, glucose transport, testosterone, or any combination thereof.

Also provided herein is a method of treating metabolic syndrome in a mammal comprising the step of modulating steroid levels in said mammal by administering at least one CVAC session, said CVAC session having a start point, an end point and more than one target which is executed between said start point and said end point, wherein the mammal can modulate the parameters of a session.

Further provided herein is a method of treating type-2 diabetes in a mammal comprising the step of modulating steroid levels in said mammal by administering at least one CVAC session, said CVAC session having a start point, an end point and more than one target which is executed between said start point and said end point, wherein the mammal can modulate the parameters of a session.

Further provided herein is a method of treating insulin resistance in a mammal comprising the step of modulating steroid levels in said mammal by administering at least one CVAC session, said CVAC session having a start point, an end point and more than one target which is executed between said start point and said end point, wherein the mammal can modulate the parameters of a session.

BRIEF DESCRIPTION OF THE DRAWINGS

FIG. 2 depicts a chart summarizing the serum lipid levels from 7 subjects following treatment with CVAC sessions. Total cholesterol, triglycerides, HDL, VLDL, and LDL levels are represented prior to and following administration of CVAC sessions for 40 minutes, twice a week throughout the study period.

FIG. 3 depicts a chart summarizing Testosterone levels from 7 subjects following treatment with CVAC sessions. Total testosterone, free testosterone, and ratios of free testosterone to total testosterone are represented prior to and following administration of CVAC sessions for 40 minutes, twice a week throughout the study period.

DETAILED DESCRIPTION OF THE INVENTION

Figure 1A:
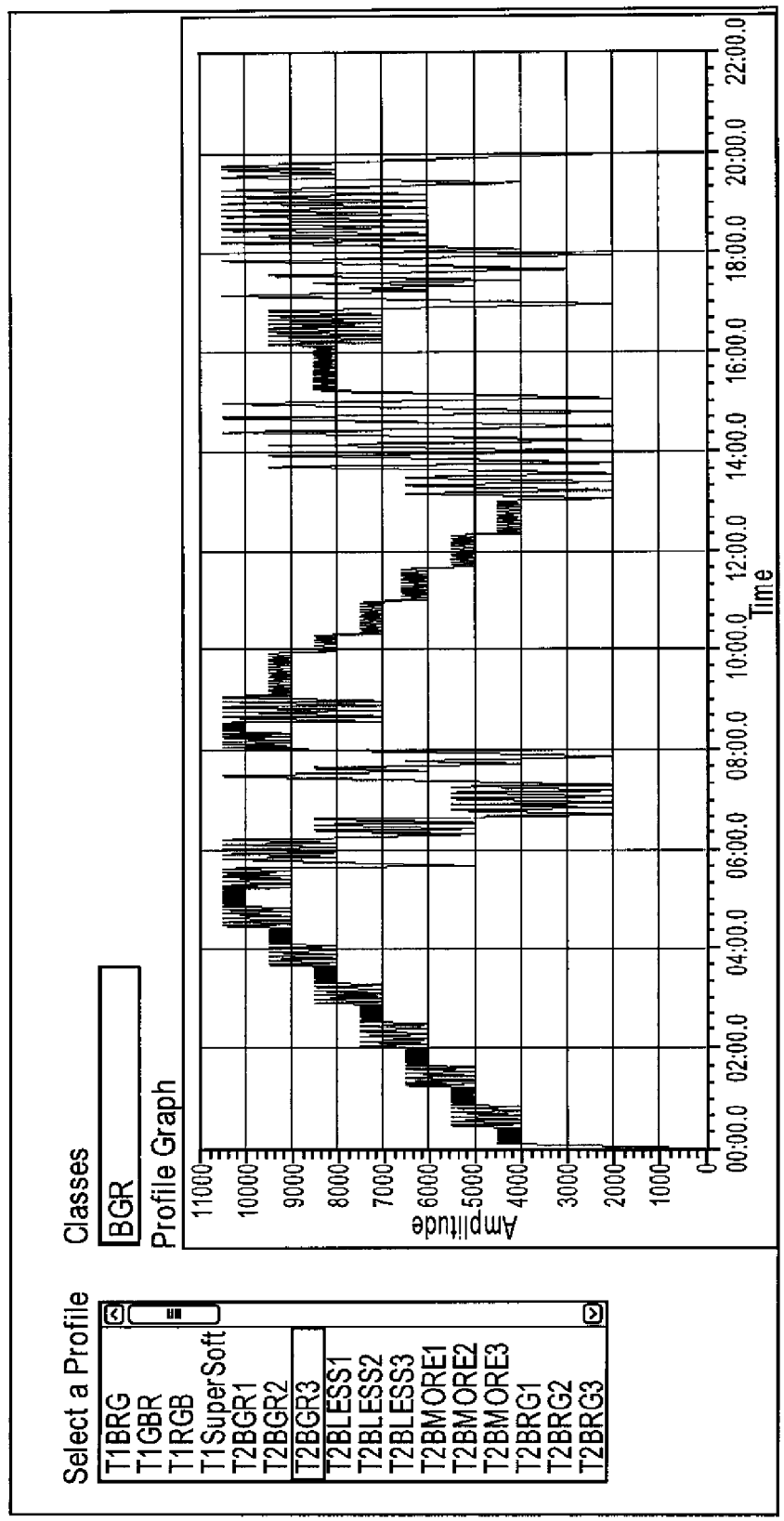
FIG. 1A depicts a graphed profile of the various pressures applied over time during an exemplary CVAC session. The Y-axis represents atmospheric pressure levels and the X-axis represents time. The varying pressures, as indicated by the changes in values on the Y-axis, were applied for various lengths of time, as indicated by changes values on the X-axis. The exemplary CVAC session depicted in FIG. 1A was 20 minutes in length.

While oxygen deprivation of the body or specific tissues can cause tissue damage, and even death, controlled deprivation of oxygen to the body and/or specific tissues has been shown to be beneficial when imposed for specific periods of time under particular conditions. In practice, most current hypoxic conditioning protocols utilize static pressures for blocks of time ranging from 30 minutes to an hour or more to achieve the desired and reported responses. Hypoxic conditioning may be provided by decreased oxygen levels in the atmosphere or by a reduction in atmospheric pressure (hypobaric conditions), thus reducing the availability of oxygen for efficient respiration. Both methods can provide beneficial results including protection of tissues from damage due to injury and ischemia.

Moderate static hypoxic preconditioning is known to provide protection from ischemic damage via tolerance. When the environmental oxygen levels are reduced (hypoxia), downstream effects include protection from damage due to subsequent hypoxia. [Sharp, F., et al., Hypoxic Preconditioning Protects against Ischemic Brain Injury, NeuroRx: J. Am. Soc. Exp. Neuro., Vol. 1: 26-25 (2004)]. This tolerance is not yet completely understood, but it has been linked to various cellular mechanisms and molecules, including, but not limited to, molecules such as erythropoietin (EPO), hypoxia-inducible factor (HIF), Tumor Necrosis Factor (TNF), glycogen, lactate, and others. [Sharp, R, et al., Hypoxic Preconditioning Protects against Ischemic Brain Injury, NeuroRx: J. Am. Soc. Exp. Neuro., Vol. 1: 26-25 (2004)]. Additionally, beneficial static hypoxic conditioning is not purely additive. Administration of sequential sessions can have detrimental effects. Oxygen concentrations that are too low result in detrimental effects to the tissues as well as the entire body. Similarly, hypoxic conditioning of longer durations can have detrimental effects in addition to providing some desired beneficial effects [Sharp, F., et al., Hypoxic Preconditioning Protects against Ischemic Brain Injury, NeuroRx: J. Am. Soc. Exp. Neuro., Vol. 1: 26-25 (2004)].

Initial understanding in the art about the effects of hypoxia focused on increased oxygenation of the blood via increased production of red blood cells mediated by increases in EPO production. While increases in EPO production are believed to increase red blood cell production, its effects are not limited to this activity. Additional studies also show protective activity for EPO in white and gray matter (brain and spinal cord tissue), inflammatory and demyelinating conditions, and other various ischemic events. [Eid, T. and Brines, M., Recombinant human erythropoietin for neuroprotection: what is the evidence?, Clin. Breast Cancer, 3 Suppl. 3:S109-15, December 2002]. Furthermore, molecules such as HIF, induced by hypoxia, regulate EPO production in addition to a variety of other activities including metabolism, angiogenesis, and vascular tone—the stimulation of which may all play a role in protecting tissue from subsequent hypoxic damage both prophylactically and post-ischemic or traumatic events. [Eckardt K. U., Kurtz, A., Regulation of erythropoietin production, Eur. J. Clin. Invest., 35(Supp. 3):13-19, (2005)]. Vascular endothelial growth factor (VEGF) is a known hypoxia induced protein under the control of HIF-1α. VEGF has been shown to have direct neuroprotective effects on mammalian spinal cord neurons following spinal cord injury. [Ding X M, et al., Neuroprotective effect of exogenous vascular endothelial growth factor on rat spinal cord neurons in vitro hypoxia, Chin. Med. J (Engl), 118(19):1644-50, Oct. 5, 2005].

Static hypoxic therapy for extended durations of time has been shown to significantly reduce total cholesterol, LDL, very low-density lipoprotein (VLDL), as well as increase HDL. Thus, the overall serum lipid profile was also significantly reduced. [Tin'Kov, A. N. and Aksenov, V. A., Effects of Intermittent Hypobaric Hypoxia on Blood Lipid Concentrations in Male Coronary Heart Disease Patients, High Alt. Med. & Biol., 3(3): 277-282 (2002)]. Type 2 Diabetes has been regarded as a relatively distinct disease entity, but recent understanding has revealed that Type 2 Diabetes (and its associated hyperglycaemia or dysglycaemia) is often a manifestation of a much broader underlying disorder, which includes metabolic syndrome. This syndrome may also be referred to as Syndrome X, and is a cluster of cardiovascular disease risk factors that, in addition to glucose intolerance, includes hyperinsulinaemia, dyslipidaemia, hypertension, visceral obesity, hypercoagulability, and microalbuminuria. Provided herein are methods of treating metabolic syndrome and/or insulin resistance. In one embodiment, metabolic syndrome is treated by modulation of testosterone levels via application of at least one CVAC session.

Alternative therapies such as oxygen deprivation are known to provide some beneficial effect as well. While oxygen deprivation of the body or specific tissues can cause tissue damage, and even death, controlled deprivation of oxygen to the body or specific tissues or a combination thereof has been shown to be beneficial when imposed for specific periods of time under particular conditions. Hypoxic conditioning may be provided by decreased oxygen levels in the atmosphere or by a reduction in atmospheric pressure (hypobaric conditions), thus reducing the availability of oxygen for efficient respiration. Both methods can provide beneficial results including prevention of damage due to inflammation and swelling. However, all current forms of hypoxic conditioning involve applications of static pressures and involve relatively long periods of application.

Additionally, application of physical energy or force to the body through relatively low levels vibrational therapy has been linked to increases in steroidogenesis, [Bosco, C. et al., Hormonal responses to whole-body vibration in men, Eur. J. Appl. Physiol., 81: 449-454 (2000)], and application of physical force to the epidermal layers of the skin through endermologie has also been shown to modulate estradiol (an estrogen) levels in women. [Benelli, L., et al., Endermologie: humoral repercussions and estrogen interaction, Aesthetic Plast. Surg. 23(5): 312-15 (1999)].

There is a high prevalence of low testosterone levels in HIV-infected individuals, and 20-25% of HIV-infected men who receive highly active antiretroviral therapy (HAART) also suffer from reduce testosterone levels. Furthermore, low testosterone levels are associated with weight loss, progression to AIDS, wasting, depression and loss of muscle mass. [Bahsin et al., Testosterone Therapy in Adult Men with Androgen Deficiency Syndromes: An Endocrine Society Clinical Practice Guideline, J. Clin. Endocrin. & Metab., 91(6):1995-2010 (2006); Arver et al., Serum Dihydrotestosterone and testosterone concentrations in Human Immunodeficiency Virus-infected men with and without weight loss, J. Andrology, 20(5):611-618 (1999)]. Testosterone therapy in HIV-infected individuals is known to improve weight gain, improve muscle strength, and provide gains in lean-body mass. Provided herein are methods for modulating steroidogenesis in HIV-infected individuals. In one non-limiting example, administration of at least one CVAC session to an HIV-infected individual increases testosterone levels in the HIV-infected individual.

Abnormalities in serum lipid levels and the process of steroidogenesis (including the modulation of steroid levels) are commonly treated with pharmaceuticals. Examples of such pharmaceuticals include, but are not limited to, Lipitor®, Zocor®, Vytorin®, and other statins as well as supplemental testosterone, estrogens, and other hormones. There is a need for alternative therapies for modulation of serum lipid levels, the modulation of steroidogenesis, and the modulation of steroid levels.

Further there is a need for such therapies without the potential negative side-effects of pharmaceutical regimens. Alternatively, there is a need for such therapies that could lessen the negative side-effects of pharmaceutical regimens by altering pharmaceutical regimens, could work beneficially with pharmaceutical regimens, or could work synergistically when used in combination with pharmaceutical regimens. There is a further need for hypobaric or hypoxic conditioning which maximizes the beneficial effects within short treatment periods that do not lead to the detrimental effects of such conditioning as found with current methods of static hypobaric conditioning. There is a further need for such hypobaric or hypoxic conditioning that utilizes multiple and/or varying pressures throughout the conditioning. There is yet a further need for hypobaric or hypoxic conditioning that incorporates vaso-pneumatic effects in addition to the hypoxic considerations.

The invention disclosed herein may provide for such needs and may do so in a manner unique and generally advantageous compared to all previous forms of hypobaric conditioning. Similarly, the invention disclosed herein can provide for vaso-pneumatic effects in a manner both unique and generally advantageous to previous vibrational therapies and endermologie. Additionally, CVAC sessions can provide for vaso-pneumatic beneficial effects. Although not limited, CVAC sessions are believed to act like a vaso-pneumatic pump on the user's body, thus stimulating flow of fluids in the body, including but not limited to blood and lymphatic fluids. The negative and positive pressures imposed by the CVAC session can affect the fluid flow or movement within a body, thus improving the delivery of beneficial nutrients, immune factors, blood, and oxygen while also improving the removal of harmful toxins, fluids, and damaged cells or tissues. Furthermore, the vaso-pneumatic effects generated during any given CVAC session can exert pressures on the body and tissues of a user. CVAC can also provide similar application of force and/or transfer of mechanical energy into the cells and tissue of a user via vaso-pneumatic pressure. However, CVAC sessions provide for a novel and unique application of varying pressure changes and times superior to the static application of force described previously, thus providing the beneficial effects of physical forces in a novel and generally advantageous way. By use of the present invention, CVAC sessions can modulate steroid levels and/or steroidogenesis in a subject. Examples of steroids modulated include, but are not limited to, testosterone and estrogen, The combination of the beneficial effects of CVAC sessions results in treatment and modulation of serum lipids and/or the modulation of steroidogenesis and steroid levels, including all the aforementioned aspects and embodiments.

A Pressure Vessel Unit (PVU) is a system for facilitating pressure changes accurately and quickly in the environment surrounding a user. A PVU can provide both reduced and increased atmospheric pressures. An example of a unique PVU and associated methods for controlling the pressure within such a PVU are described in U.S. Patent Publication number 2005/0056279 A1 which is incorporated herein by reference. A variety of PVUs may be used in conjunction with the methods disclosed herein, including but not limited to those described in the U.S. Patent Publication number 2005/0056279, such as variable or fixed pressure and temperature hypobaric units. Other pressure units or chambers will be known to those of skill in the art and can be adapted for use with the disclosed methodologies.

Methodology of the Cyclic Variations in Altitude Conditioning (CVAC) Program:

The methodology of the present invention encompasses a set of pressure targets with defined transitions. Additional targets can be included such as temperature or humidity, and these targets can be implemented concurrently, prior to, or subsequent to the pressure targets. The permutations of targets are customizable to the individual and condition to be treated. Some of the terms relating to this methodology are defined below for a better understanding of the methodology as used in the context of the present invention.

A CVAC Program:

Every user will respond in a unique manner to changes in air pressure, temperature and oxygen levels that occur during cyclic variations in altitude conditioning. This necessitates a customized approach to delivering a highly effective and efficacious CVAC program to each user The program consists of a set of sessions, which are administered to the user as a serial round or cycle. This means that a user may have a session that they start and repeat a given number of times and then proceed to the next scheduled session which will be repeated a given number of times. A program may contain a set of one or more sessions, each of which preferably has a repetition schedule. The sessions are preferably delivered in a scheduled order, which repeats itself like a loop such that the user is administered one session at a time for a specified number of times. The user may then be administered the next scheduled session a specified number of times. This process is preferably repeated until the user is administered the last element of the scheduled sessions set. When the requisite repetitions have been accomplished, preferably the process repeats itself beginning at the first element of the scheduled sessions set. A session or groups of sessions may be repeated multiple times before changing to a subsequent session or group of sessions, however, sessions may also be administered as few as one time before beginning the next session in the sequence. Subsequent sessions can contain targets that are identical to the previous session, or they can implement new permutations of desired targets. The combination of sessions and targets within sessions is customizable based on the desired physiological outcome and assessment of the user. Alternatively, a user may also modulate the parameters of a CVAC session, in certain embodiments from within the unit, thus providing for real-time user feedback and alterations. As used in reference to parameter of a CVAC session, modulation includes any changes, positive and negative, made to the parameters of the CVAC session. The parameters are described herein. This comprises a Cyclic Variations in Altitude Conditioning (CVAC) Program.

A CVAC Session:

A CVAC Session comprises of a set of targets which are multiple atmospheric pressures, and a CVAC session includes start and end points, and more than one target which is executed between the start and end points. These targets are delivered in an order that may vary and are executed in a variety of patterns including, but not limited to, cyclic, repeating, and/or linear variations. When a target is executed as contemplated herein, executed includes a change in pressure from one pressure value to another pressure value within a CVAC device as also described herein. The methodologies described herein provide superior benefits compared to previously described static hypobaric pressure therapies in multiple ways, which can include reduced time frames of application and unique variations and combinations of atmospheric pressures. Furthermore, CVAC sessions can also provide beneficial effects via the vaso-pneumatic properties associated with the application of such sessions. The starting points and ending points in any CVAC Session are preferably the ambient pressure at the delivery site. The targets inherent in any CVAC Session are connected or joined together by defined transitions. These transitions are either increases in pressure (descent) or decreases in pressure (ascent), or a combination of the two. The nature of any transition may be characterized by the function of "delta PIT" (change in pressure over time). Transitions may be linear or produce a waveform. Preferably, all transitions produce a waveform. The most desirable waveforms are Sine, Trapezoidal and Square. Additional targets which modulate time, temperature, and/or humidity are also run concurrently, sequentially, or at other intervals with the pressure targets when such additional targets and conditions are desired. The entire collection of targets and transitions are preferably delivered in a twenty minute CVAC Session, although the time of each session may vary in accordance with the desired outcome of the administration of the CVAC Sessions. For example, CVAC sessions may be administered over minute increments such as 5, 10, 15, 16, 17, 18, 19, 20, 25, 30 minutes and/or more. The length of each CVAC Session is customizable for each user.

A Set-Up Session: The Set-Up Session may also be considered a Program. It is a single Session designed to prepare a new user for the more aggressive maneuvers or transitions encountered in the subsequent Sessions that the user will undergo. The Set-Up session accounts for all ages and sizes and conditions, and assumes a minimal gradient per step exercise that allows the ear structures to be more pliant and to allow for more comfortable equalization of pressure in the ear structures. The purpose of the Set-Up session is to prepare a new user for their custom Program based upon the group into which they have been placed. The function of the Set-Up session is to qualify a user as being capable of adapting to multiple pressure changes in a given Session with acceptable or no discomfort. Set-Up session transitions may be linear or produce a waveform. Preferably, all transitions are linear. This is accomplished by instituting a gradient scale increase in pressure targets from very slight to larger increments with slow transitions increasing until a maximum transition from the widest difference in pressure targets is accomplished with no discomfort. The structure of a preferred Set-Up session is as follows: as with any Session, the starting point and ending point are both preferably at ambient pressure. A target equivalent to 1000 ft above ambient is accomplished via a smooth linear transit. A second target equivalent to 500 ft less than the first target is accomplished via a slow to moderate transit. These two steps are repeated until the user returns a "continue" or "pass" reply via an on-board interface. When the user has indicated that they are prepared to continue, the initial target (1000 ft) is increased by a factor of 500 ft, making it 1500 ft. The secondary target (500 ft less than the first target) remains the same throughout the session until the exit stage is reached. In this example, each time the user indicates that they are ready to increase their gradient, the target is increased by a factor of 500 ft. At this time, the transits remain the same but the option of increasing gradient (shorter time factor) in the transits is available. A user preferably has the option of resuming a lower gradient if desired. There can be an appropriate icon or pad that allows for this option on the on-board interface display screen. Preferably, the Set-Up Session lasts no longer than 20 minutes. A Set-Up session typically runs for twenty minutes maximum and executes a final descent to ambient atmospheric pressure upon beginning the last transit. The Set-Up session is a new user's Program until the user is able to fully complete the Set-Up session (that is to continue the targets and transits to the highest gradient) with no interrupts or aborts. When administering CVAC sessions for medical treatment, Set-Up sessions may be customized to suit the requirements of their medical condition. The determination of the appropriate Set-Up Session can be made with guidance from or consultation with a user's qualified health professional, such as a treating physician.

The Interrupt:

During any phase in a Session wherein a user desires to stop the Session at that point for a short time, they may do so by activating an icon or other appropriate device on the on-board interface touch screen or control pad or notifying the operator of the device. This will hold the Session at the stage of interruption for a predetermined time period, such as a minute, at which time the Session will continue automatically. Preferably, a Session may be interrupted three times after which a staged descent will occur and the user will be required to exit the pressure vessel. The user's file may be flagged and the user may be placed back on the Set-Up Sessions until they can satisfactorily complete it. A warning or reminder may be displayed on the screen each time an interrupt is used that informs the user of how many times interrupt has been used and the consequences of further use. During any session, be it a Set-Up session or other type of session, a staged descent is also available if the user develops ear or sinus discomfort or wishes to terminate the session for any reason. A staged descent is characterized by slow, 1000 ft sine wave descent transits with re-ascensions of 500 ft at each step. The descents can be of greater or lesser transits but the ratio is usually about 1.5:1. At any time during the staged descent, the user can interrupt the descent and hold a given level or resume a previous level until comfort is achieved. The user may also re-ascend at their option if the staged descent is too aggressive. Any re-ascension is done in stages as described above. The user can subsequently indicate a "continue" on the descent and the staging will resume. This stepping continues until ambient pressure is reached whereupon the canopy or entrance to the device opens such that the user can exit the pressure vessel.

The Abort:

When a user wishes to end a session immediately and quickly exit the pressure vessel, the abort function can be activated. Touching the "abort" icon on the on-board interface touch pad/screen or notifying the operator of the device enables this option. A secondary prompt is activated acknowledging the command and asking the user if they are sure they want to abort. The user indicates their commitment to the command by pressing "continue" or "yes". The program is aborted and a linear moderate descent is accomplished to ambient pressure whereupon the canopy or entrance to the device opens and the user exits. The user's file is flagged. The next time the user comes in for their session, the user is asked whether the abort was caused by discomfort. If yes, the user is placed back on the Set-Up session program. If no, the user is asked if they wish to resume their regularly scheduled session. The client is given the option of resuming their regularly scheduled Session or returning to the Set-Up session.

Program and Target Criteria, Including Medically Significant Criteria:

Preferably, a user is categorized into a group of users having similar body-types with similar characteristics based upon answers to a questionnaire or information otherwise obtained from the user. The information from the user guides the construction of custom CVAC programs for each individual. When administering CVAC programs for treatment of serum lipid levels or treatment of steroidogenesis, the medical status of the user can also be used to determine appropriate pressures and additional parameters (such as duration, temperature, or humidity) of the targets. Custom session targets may be administered based upon the medical condition and therapy desired. The acceptable and appropriate target parameters may be obtained as described herein and through consultation with the user's physician or other appropriate health-care provider prior to designing session targets and administering a CVAC session. However the known contraindications of CVAC are similar to those of commercial air travel, allowing for a broad range of application.

Methods of Treatment:

In one aspect of the invention, CVAC sessions for the treatment of serum lipid levels are administered preferably for at least 10 minutes, and more preferably at least 20 minutes, with variable frequency. Additional administration periods may include, but are not limited to, about 10 minutes, about 20 minutes, about 30 minutes, about 40 minutes, about 60 minutes, between 10 and 20 minutes, between 20 and 30 minutes, between 30 and 60 minutes, and between 60 and 120 minutes. Frequencies of sessions or series of sessions may include, but are not limited to, daily, monthly, or when medically indicated or prescribed. The frequency and duration of the sessions can be altered to suit the medical condition to be treated, and CVAC sessions may be administered as single sessions, or as a series of sessions, preferably with a Set-Up Session as described herein. For example, the frequency of sessions or series of sessions can be administered 3 times a week for 8 weeks, 4 times a week for 8 weeks, 5 times a week for 8 weeks, or 6 times a week for 8 weeks. Additional frequencies can be easily created for each individual user. Similarly, the targets in the sessions can also be altered or adjusted to suit the individual and medical condition to be treated. If at any time the user or attendant determines that the session is not being tolerated well, an abort may be initiated and the user brought down safely and exited. The permutations of targets can be customized to the individual, and may again be identified with the help of any person skilled in the art, such as a treating physician. Furthermore, the variations may be administered in regular intervals and sequence, as described, or in random intervals and sequence. The variations in number, frequency, and duration of targets and sessions can be applied to all methods of treatment with CVAC described herein. Treat or treatment, as used herein refers to the treatment of a disease or disorder related to abnormal levels of lipids. This includes, but is not limited to, inhibiting the disease or disorder, arresting the development of the disease or disorder, relieving the disease or disorder, or stopping the symptoms of the disease or disorder. Thus, as used herein, the term "treatment" is used synonymously with the terms "amelioration," "prophylaxis," or "prevention." Treatment can refer to a reduction in lipid levels compared to no treatment (e.g. about 1% less, about 2% less, about 3% less, about 4% less, about 5% less, about 10% less, about 20% less, about 50% less, about 100% less, and any range therein).

In an embodiment of the present invention, Cyclic Variations in Altitude Conditioning Program (CVAC) is used to treat users who wish to modulate their serum lipid levels. CVAC is administered to stimulate the reduction in serum lipid levels in a user as well as stimulate other associated physiological processes affected by CVAC treatment such as fluid movement, vas-pneumatic pressure on the user, and the cellular processes initiated by hypoxic exposure. Treatment is administered through the use of one or more CVAC sessions. Such sessions may be user defined or custom-defined with input from the user's physician. In an embodiment of the present invention, Cyclic Variations in Altitude Conditioning Program (CVAC) is used to treat users who wish to lower their serum lipid levels. In another embodiment of the present invention, CVAC is used to modulate LDL. In another embodiment of the present invention, CVAC is used to modulate cholesterol. In another embodiment of the present invention, CVAC is used to modulate VLDL (very low-density lipoprotein). In yet another embodiment of the present invention, CVAC is used to modulate HDL. In further embodiments, two or more of, in any combination of, cholesterol, VLDL, LDL, and HDL can be modulated by the same application of at least one CVAC session.

In another aspect of the present invention, CVAC sessions are administered for the modulation of steroidogenesis. As described herein, modulation of steroidogenesis includes, but is not limited to, increases and decreases in steroid levels in the user. Steroidogenesis includes, but is not limited to, the production of steroids. Steroid as used herein includes, but is not limited to, all hormones and steroid compounds produced from cholesterol. Examples of groups of such compounds include androgens, estrogens, progestogens, mineralocorticoids, and glucocorticoids. Further examples of hormones include testosterone and estrogens. Still further examples of estrogens include estradiols, estriols, and estrones. Similarly, the treatment of steroidogenesis includes administration for modulation of steroid levels and steroidogenesis. CVAC sessions for the treatment of steroidogenesis are administered preferably for at least 10 minutes, and more preferably at least 20 minutes, with variable frequency. Additional administration periods may include, but are not limited to, about 10 minutes, about 20 minutes, about 30 minutes, about 40 minutes, about 60 minutes, between 10 and 20 minutes, between 20 and 30 minutes, between 30 and 60 minutes, and between 60 and 120 minutes. Frequencies of sessions or series of sessions may include, but are not limited to, daily, monthly, or when medically indicated or prescribed. The frequency and duration of the sessions can be altered to suit the medical condition to be treated, and CVAC sessions may be administered as single sessions, or as a series of sessions, preferably with a Set-Up Session as described herein. For example, the frequency of sessions or series of sessions can be administered 3 times a week for 8 weeks, 4 times a week for 8 weeks, 5 times a week for 8 weeks, or 6 times a week for 8 weeks. Additional frequencies can be easily created for each individual user. Similarly, the targets in the sessions can also be altered or adjusted to suit the individual and medical condition to be treated. If at any time the user or attendant determines that the session is not being tolerated well, an abort may be initiated and the user brought down safely and exited. The permutations of targets can be customized to the individual, and may again be identified with the help of any person skilled in the art, such as a treating physician. Furthermore, the variations may be administered in regular intervals and sequence, as described, or in random intervals and sequence. The variations in number, frequency, and duration of targets and sessions can be applied to all methods of treatment with CVAC described herein. As used herein, "modulation" includes increases or decreases in steroidogenesis as well as increases or decreases in serum and/or tissue steroid levels. Modulation can refer to increases in serum or tissue steroid levels compared to no treatment (e.g. about 1% more, about 2% more, about 3% more, about 4% more, about 5% more, about 10% more, about 20% more, about 50% more, about 100% more, and any range therein).

In an embodiment of the present invention, CVAC is administered to increase the levels of testosterone in the user. In a further embodiment, CVAC is administered to modulate levels of steroids in an HIV-infected or HIV-positive individual. In one non-limiting example, at least one CVAC session is administered to and HIV-infected individual to increase the levels of testosterone in the HIV-infected individual. In an additional embodiment, CVAC is administered to a user to increase the levels of estrogen in an HIV-infected user. In an additional embodiment, CVAC is administered to a user to decrease the levels of testosterone or estrogen in the user. In yet another embodiment, CVAC is administered to a user to modulate the levels of glucocorticoids, mineralocorticoids, or androgens. In still further embodiments, CVAC is administered to modulate steroid levels and cholesterol levels in an HIV-infected user. In still further embodiments, CVAC is administered to modulate both steroid levels and serum lipid levels in an HIV-infected user. In further embodiments, at least one CVAC session is administered to increase steroid levels in an HIV-infected subject for the treatment of weight loss, wasting syndrome, or loss of muscle mass. Treatment is administered through the use of one or more CVAC sessions. Such sessions may be user defined or custom-defined with input from the user's physician.

In yet another embodiment, at least one CVAC session is administered to a user to modulate steroid levels in a subject for the treatment, prevention or amelioration of metabolic syndrome. In additional embodiment, at least one CVAC session is administered to modulate steroid levels in an individual for the treatment prevention or amelioration of type-2 diabetes. In yet another embodiment, at least one CVAC session is administered to modulate steroid levels in an individual for the treatment, prevention or amelioration of insulin resistance. In a further embodiment, at least one CVAC session is administered to increase steroid levels in a subject for the treatment of metabolic syndrome. In another embodiment, at least one CVAC session is administered to increase steroid levels in a subject for the treatment of type-2 diabetes. In yet another embodiment, at least one CVAC session is administered to increase steroid levels in a subject for the treatment of insulin resistance. In one non-limiting example, at least one CVAC session is administered to increase testosterone in a subject for the treatment of metabolic syndrome. In another non-limiting example, at least one CVAC session is administered to increase testosterone in a subject for the treatment of type-2 diabetes. In additional embodiments, CVAC sessions are administered to increase steroid levels for the prevention of metabolic syndrome or insulin resistance.

CVAC sessions for any of the aforementioned aspects and embodiments may also be used in combination with pharmaceutical regimens or non-pharmaceutical therapies such as physical therapy or homeopathic therapies. As described above, CVAC sessions of any combination or permutation can be administered prior to, concurrent with, or subsequent to administration of a pharmaceutical, pharmaceuticals, or non-pharmaceutical therapy. Myriad permutations of pharmaceutical therapies, non-pharmaceutical therapies, and CVAC session combinations are possible, and combinations appropriate for the type of medical condition and specific pharmaceutical may be identified with the help of any person skilled in the art, such as a treating physician.

Figure 1B:
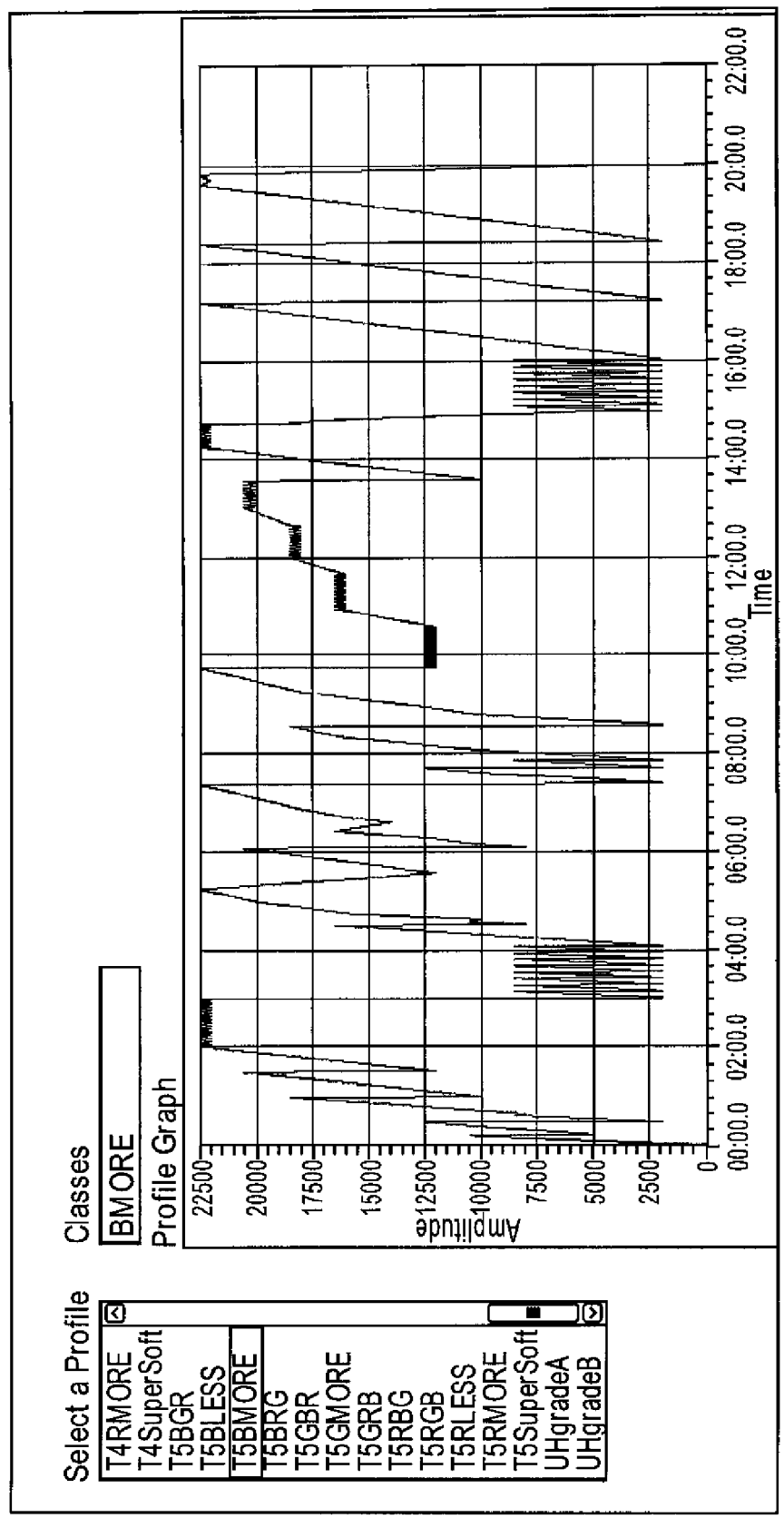
FIG. 1B depicts a different graphed profile of the pressures applied over time during another exemplary CVAC session. The Y-axis again represents atmospheric pressure levels and the X-axis represents time. Different pressures were again applied, as indicated by changes in value on the Y-axis, for various lengths of time, as indicated by the changes in values on the X-axis. This exemplary CVAC session was also 20 minutes in length.

Specific examples of a CVAC session are shown graphically in FIGS. 1A and 1B. In both figures, the parameters of the program are shown as a line graph with axes that correspond to time (x-axis) and pressure change (y-axis).

Efficacy of Treatment

Assessment of CVAC efficacy in the aforementioned aspects and embodiments can be investigated through various physiological parameters. Changes in serum lipid levels can be assessed by evaluation of cholesterol, VLDL, LDL, and HDL levels in a user. By example only, when levels of LDL are the physiological parameter examined, decreases in the levels of LDL in a user's blood or serum are indicative of efficacious CVAC treatments. Similarly, when the physiological parameter is cholesterol, reductions in cholesterol levels are indicative of efficacious CVAC treatment. Serum steroid and hormone levels can be assayed via RIA, ELISA, immunometric assays, equilibrium dialysis, or liquid chromatography tandem mass spectrometry. Additional steroid and hormone assays are known in the art and contemplated herein. In one example, serum total testosterone is determined by RIA, with free testosterone determined by equilibrium dialysis. Additionally, weight gain, increases in lean-body mass, and/or increases in muscle strength indicate efficacy of CVAC for increasing steroid levels in an HIV-infected subject.

Further methods of assessing CVAC efficacy for changes in serum lipid levels include non-invasive imaging techniques such as MRI as well as invasive imaging techniques such as catheterization and endoscopy. Additional imaging techniques will be well known in the art and easily applied to the present invention.

When treating or modulating steroidogenesis and/or steroid levels, a user's steroid or hormone levels may be assessed for determination of CVAC efficacy. For but one example only, when testosterone is the physiological parameter assessed, increases in testosterone levels can be indicative of efficacious CVAC treatment. Similarly, increases in estrogen levels can be indicative of efficacious CVAC treatment. In further embodiments, modulation of a user's androgen levels, progestogen levels, mineralocorticoid levels, or glucocorticoid levels are indicative of efficacious CVAC treatment. In still further embodiments, decreases in a user's androgen levels, progestogen levels, mineralocorticoid levels, or glucocorticoid levels are indicative of efficacious CVAC treatment.

Additionally, increases in a subjects weight, muscle mass, or lean-body mass are indicative of efficacious CVAC treatment for increasing steroid levels in an HIV-infected subject. Similarly, increases in muscle strength can also be are indicative of efficacious CVAC treatment for increasing steroid levels in an HIV-infected subject. Established methods of monitoring and assessing weight gain, muscle mass, lean-body mass, and muscle strength are known in the art and contemplated herein.

Efficacy of CVAC treatments for modulation of steroid levels for the treatment of metabolic syndrome, type-2 diabetes, or insulin resistance can be evaluated by assessment of insulin regulation, glucose tolerance, and glucose transport. Assays for such criteria are well know in the art and can be evaluated with a variety of imaging and assessment techniques. By example only, increase of insulin levels is indicative of efficacious CVAC treatments for modulation of steroid levels to treat metabolic syndrome type-2 diabetes, or insulin resistance. Similarly, a decrease of glucose levels is indicative of efficacious CVAC treatment for the modulation of steroid levels to treat metabolic syndrome, type-2 diabetes, or insulin resistance, and modulation of glucose transport is indicative of CVAC efficacy for the modulation of steroid levels to treat metabolic syndrome, type-2 diabetes, or insulin resistance. Conversely, a lack of change in the user's insulin (or with any of the physiological markers described herein) does not necessarily indicate that the CVAC treatments are not achieving positive results. Efficacy of CVAC sessions for the modulation of steroid levels to treat metabolic syndrome, type-2 diabetes, or insulin resistance can also be determined by assessment of testosterone levels in a user, as described above.

Additional criteria for assessing the efficacy of the aforementioned aspects and embodiments will be known by those of skill in the art and can be employed to assess the beneficial effects of CVAC programs.

Methods for treating serum lipid levels and treating steroidogenesis by administration of various environmental pressure levels for hypoxic conditioning are disclosed herein. Previously described PVU and CVAC methodology is used to implement the methods for treatment of the aforementioned conditions, and alternative PVUs can be used with the disclosed methodologies.

EXAMPLES

Example 1

To assess the efficacy of CVAC sessions, 13 individuals, all between the ages of 20 and 40 years old, were administered CVAC sessions and changes in their erythropoietin (EPO) levels were measured. Frequency of CVAC administration was 3 CVAC sessions per day, 5 days per week, for seven weeks. All subjects were administered three different profiles, entitled BRG, RSG, and GRB. Each CVAC session profile cycled through a rotation of the pressures and parameters associated with that given profile. After completing three 20-minute CVAC sessions consisting of a given profile, each subject then switched to a second CVAC session profile. The subjects then experienced three CVAC sessions of this second profile before switching to the third CVAC session profile. After completion of three CVAC sessions based on the third profile, the subject then returned to the first profile, with each profile be repeated in triad form. All CVAC sessions, regardless of the profile used, had a pressure ceiling corresponding to a specific tier. Subjects then progressed through five tiers, and each tiered level included a maximum pressure ceiling that corresponded to an altitude of 4000 feet higher than the previous tier. A subject was not allowed to switch to the next higher tier until the subject had experienced fifteen CVAC sessions at the lower tier. Sham sessions (or control sessions) correspond to the cycling of the five tier levels but do not contain any meaningful pressure changes (e.g. pressure changes equivalent to altitude of 2000 feet with very few changes in duration), thus the subjects experience the CVAC session for the equivalent 20 minute session, but without the pressure changes and durations. In this study, profiles BRG (FIGS. 4, 8, 12, and 16), RBG (FIGS. 5, 9, 13, and 17), GRB (FIGS. 6, 10, 14, and 18) (tiers 2-5 respectively) were administered in sequential order for tiers 2-5 as described above. Sham sessions corresponding to tiers 2, 3, 4, and five (FIGS. 7, 11, 15, and 19) were administered where indicated and the graphical representations corresponding to pressures are not indicative of the pressure changes in the CVAC unit. The simulated graphical output was for control purposes to keep the subjects blinded to the sham sessions.

Increases in EPO were measured prior to administration of CVAC and three hours post-administration of CVAC, and EPO concentration is expressed as mIU/ml. Thus changes in EPO can be represented by the formula: deltaEPO=Post-CVAC EPO mIU/ml−pre-CVAC EPO mIU/ml. The study found that EPO levels changed over the study period in the population. Specifically, mean changes in EPO concentration increased from 0.2 mIU/ml following the first 2 weeks of CVAC administration to 2.0 mIU/ml following 8 weeks of the CVAC administration. The changes in EPO levels found in the study population indicate that the administration of CVAC sessions can positively modulate EPO production, hence providing an alternative and efficacious method to exogenous EPO administration.

Example 2

Figure 4:
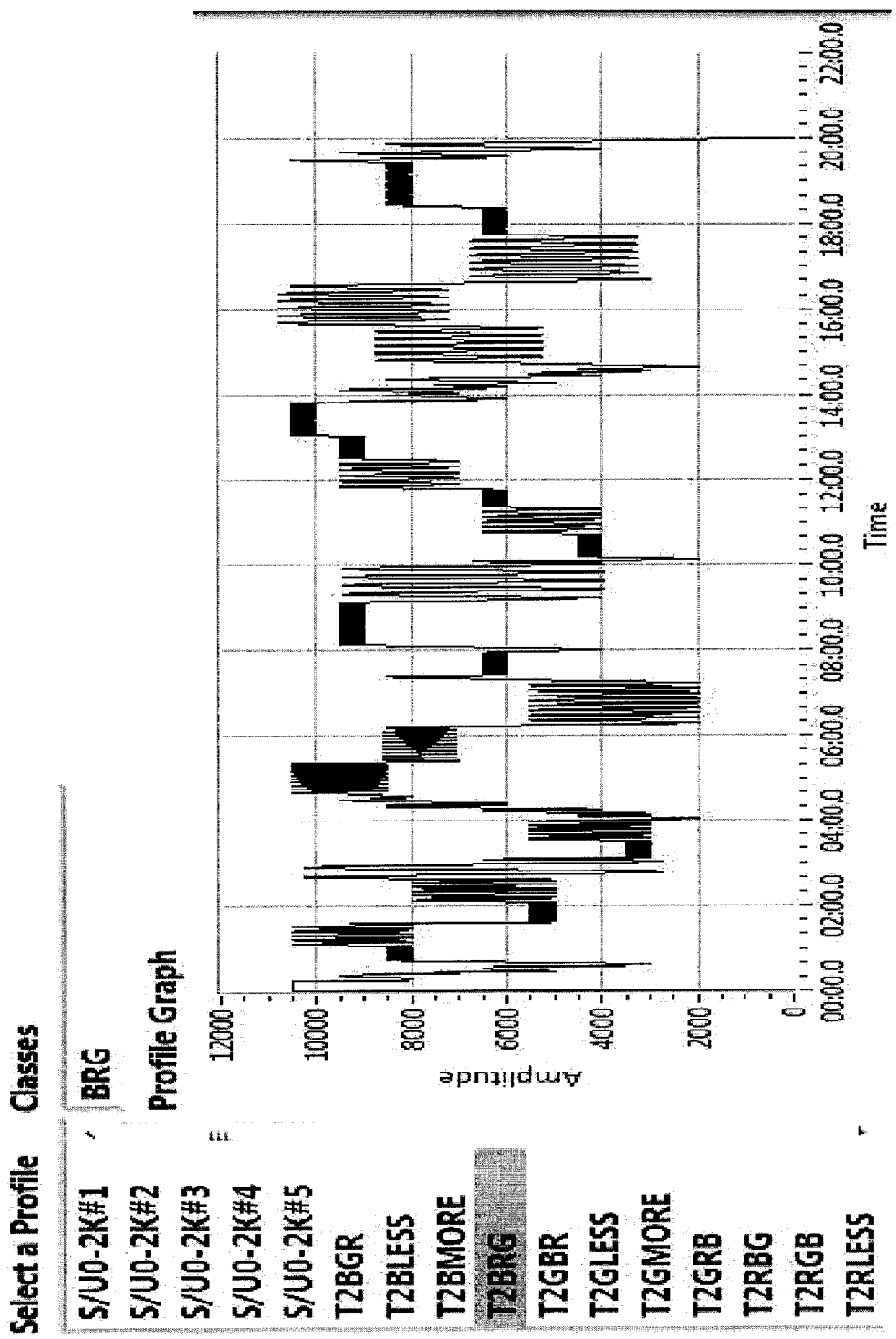
FIG. 4 depicts a graph of the various pressures applied over time during a CVAC session using profile BRG at tier 2.
Figure 5:
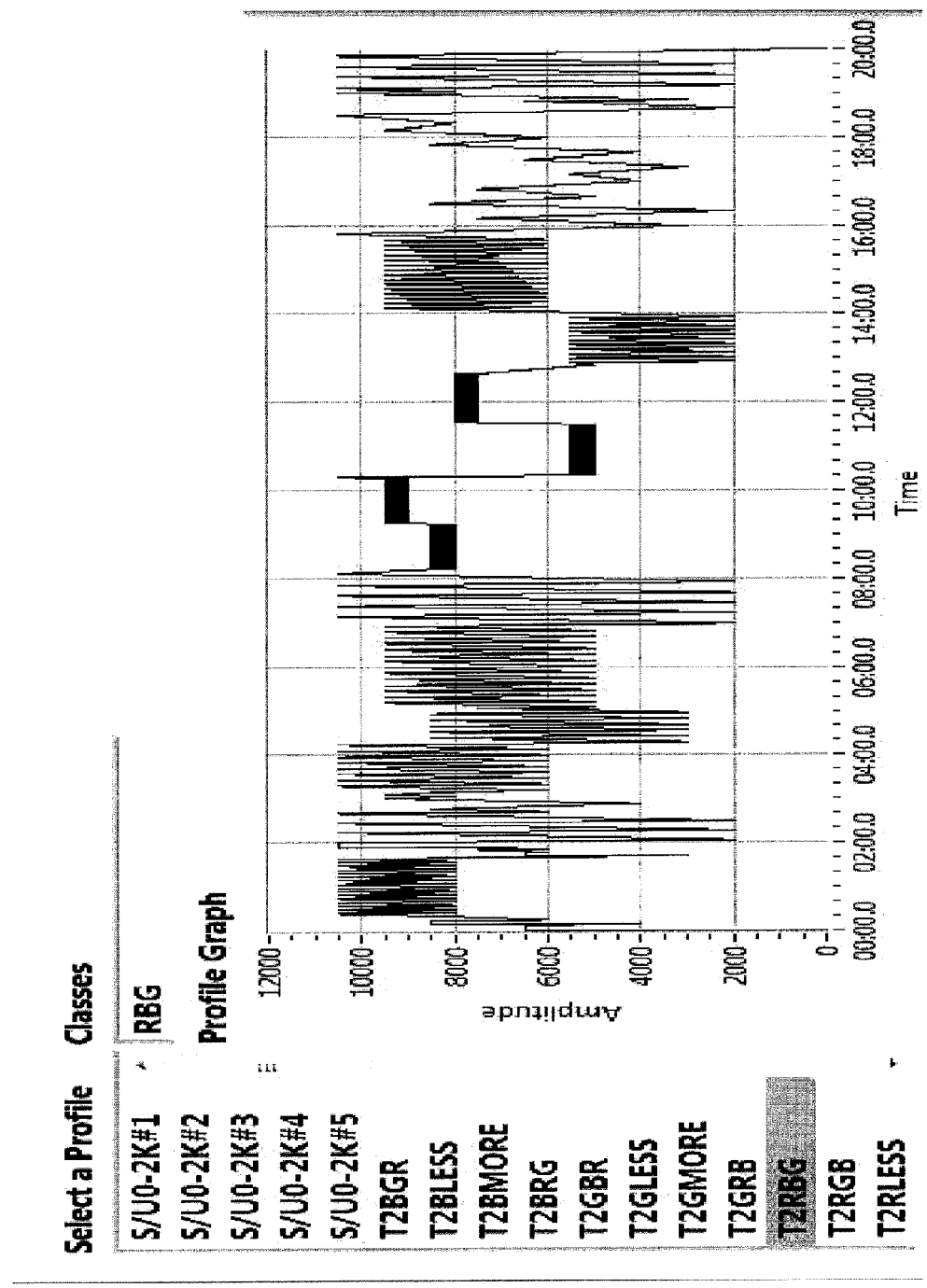
FIG. 5 depicts a graph of the various pressures applied over time during a CVAC session using profile RBG at tier 2.
Figure 6:
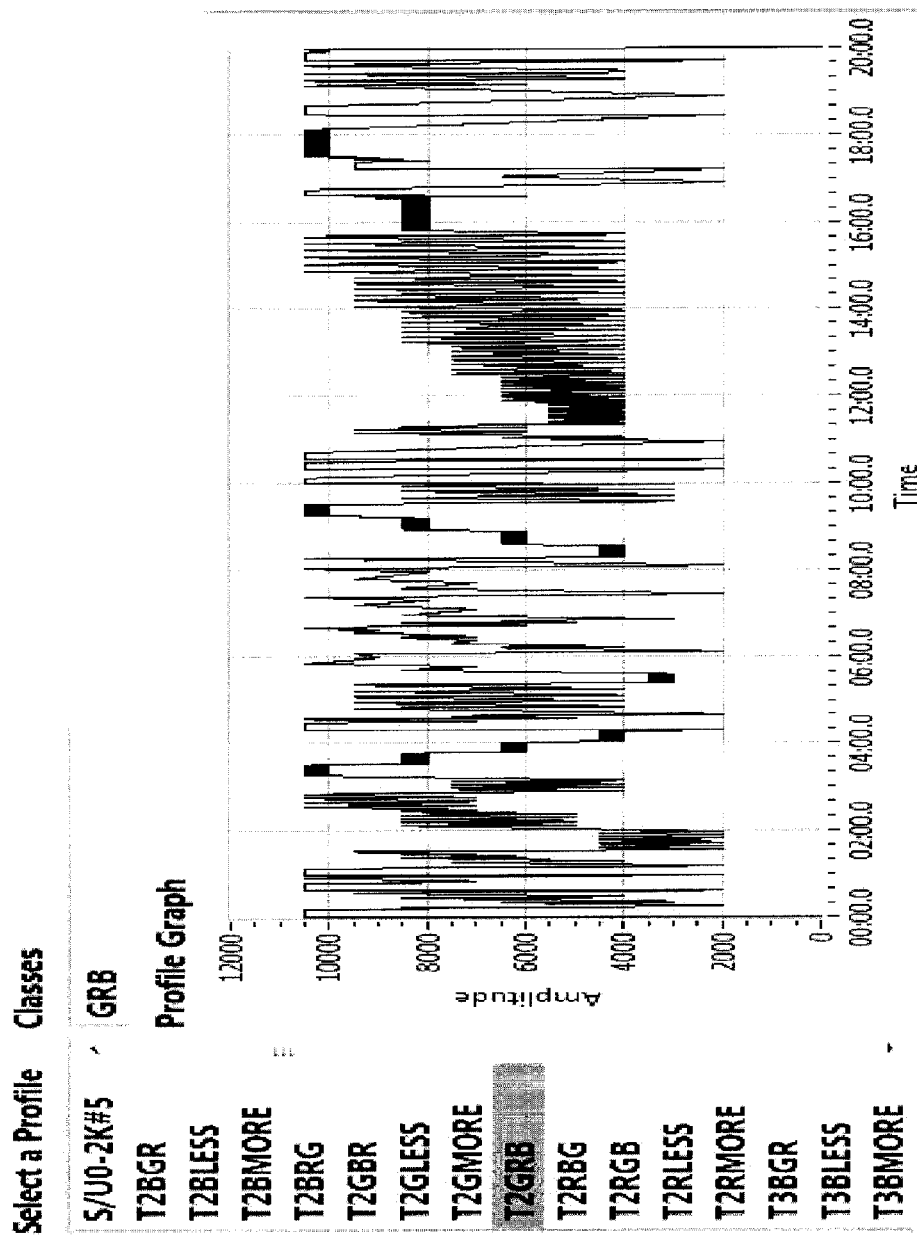
FIG. 6 depicts a graph of the various pressures applied over time during a CVAC session using profile GRB at tier 2.
Figure 7:
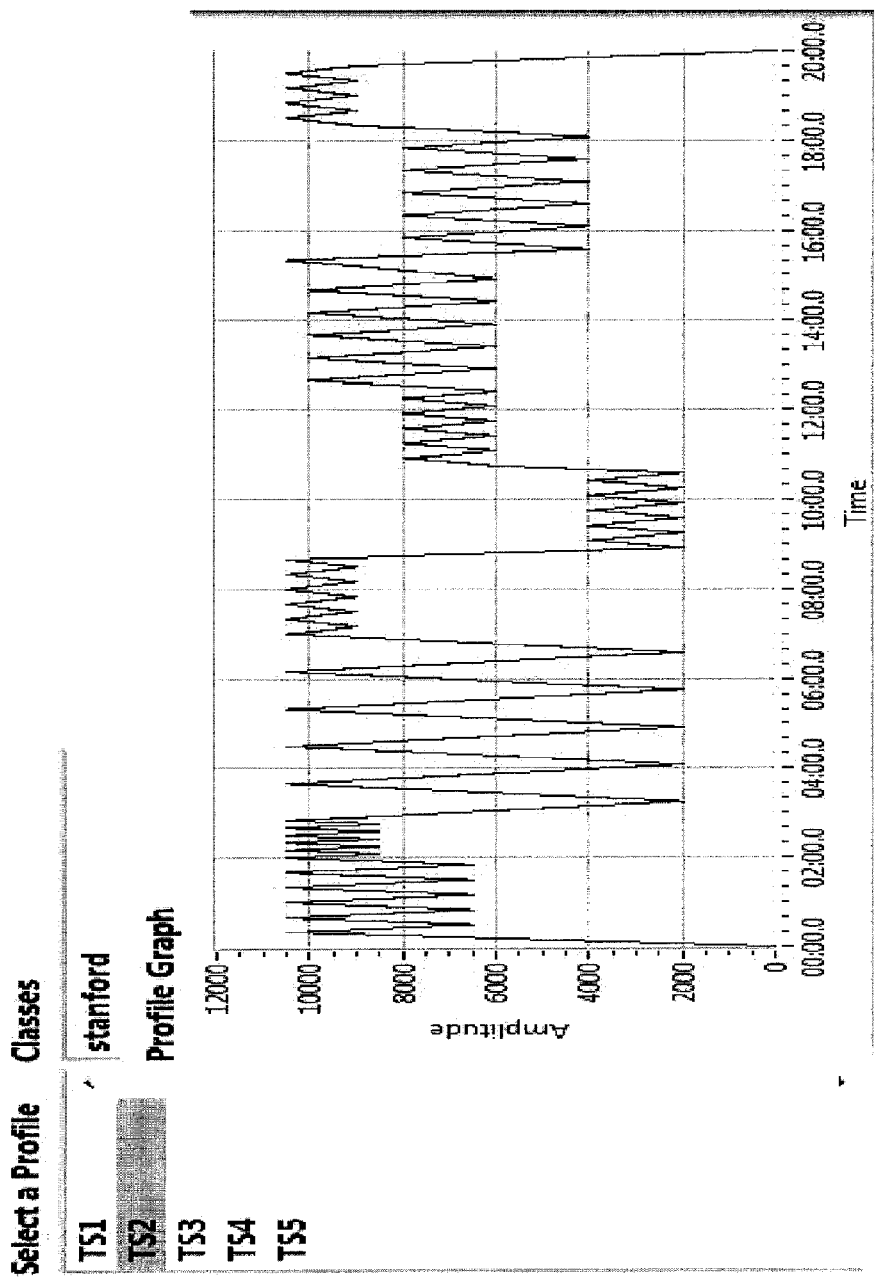
FIG. 7 depicts a graph of the various pressures applied over time during a CVAC session using profile sham at tier 2.
Figure 8:
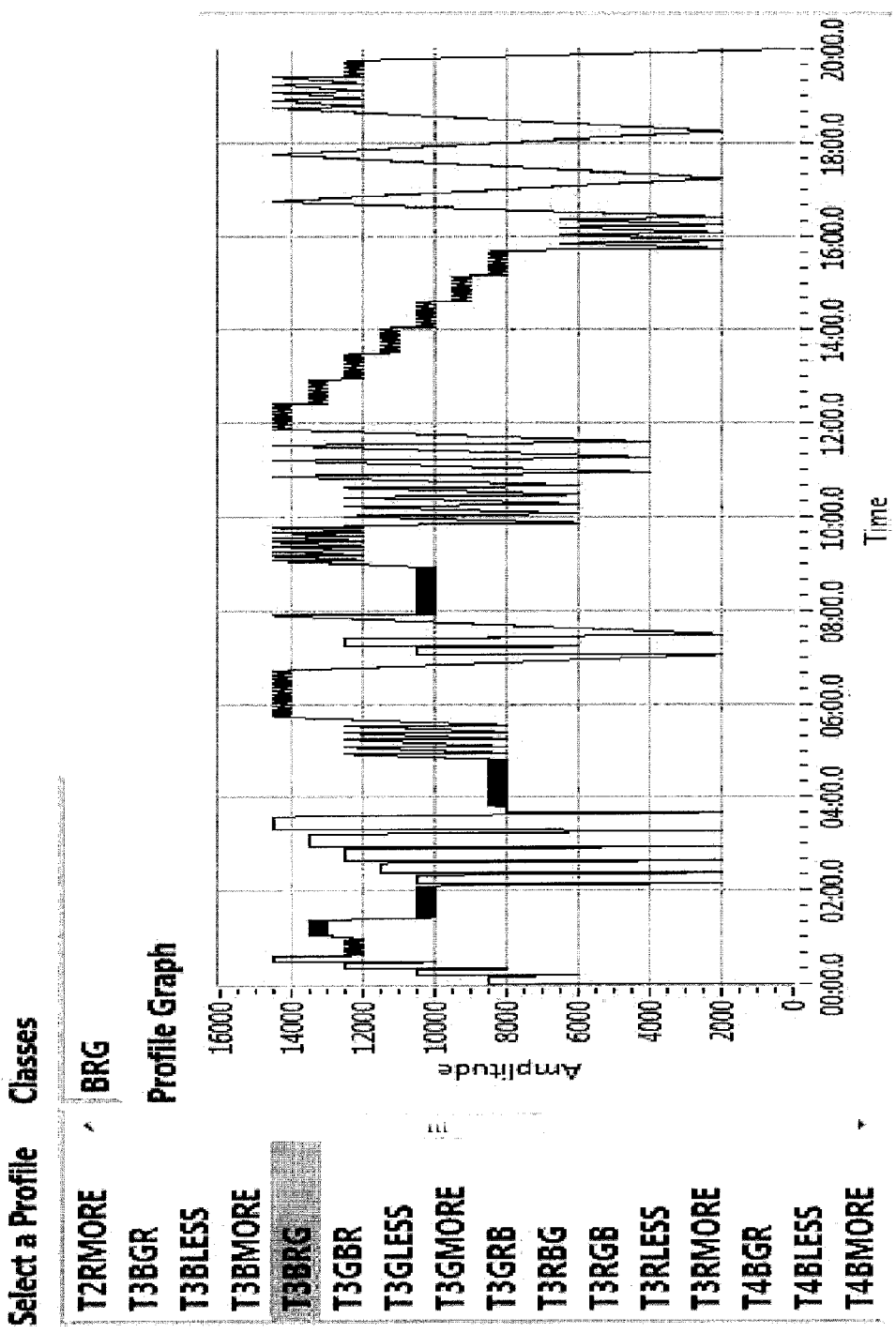
FIG. 8 depicts a graph of the various pressures applied over time during a CVAC session using profile BRG at tier 3.
Figure 9:
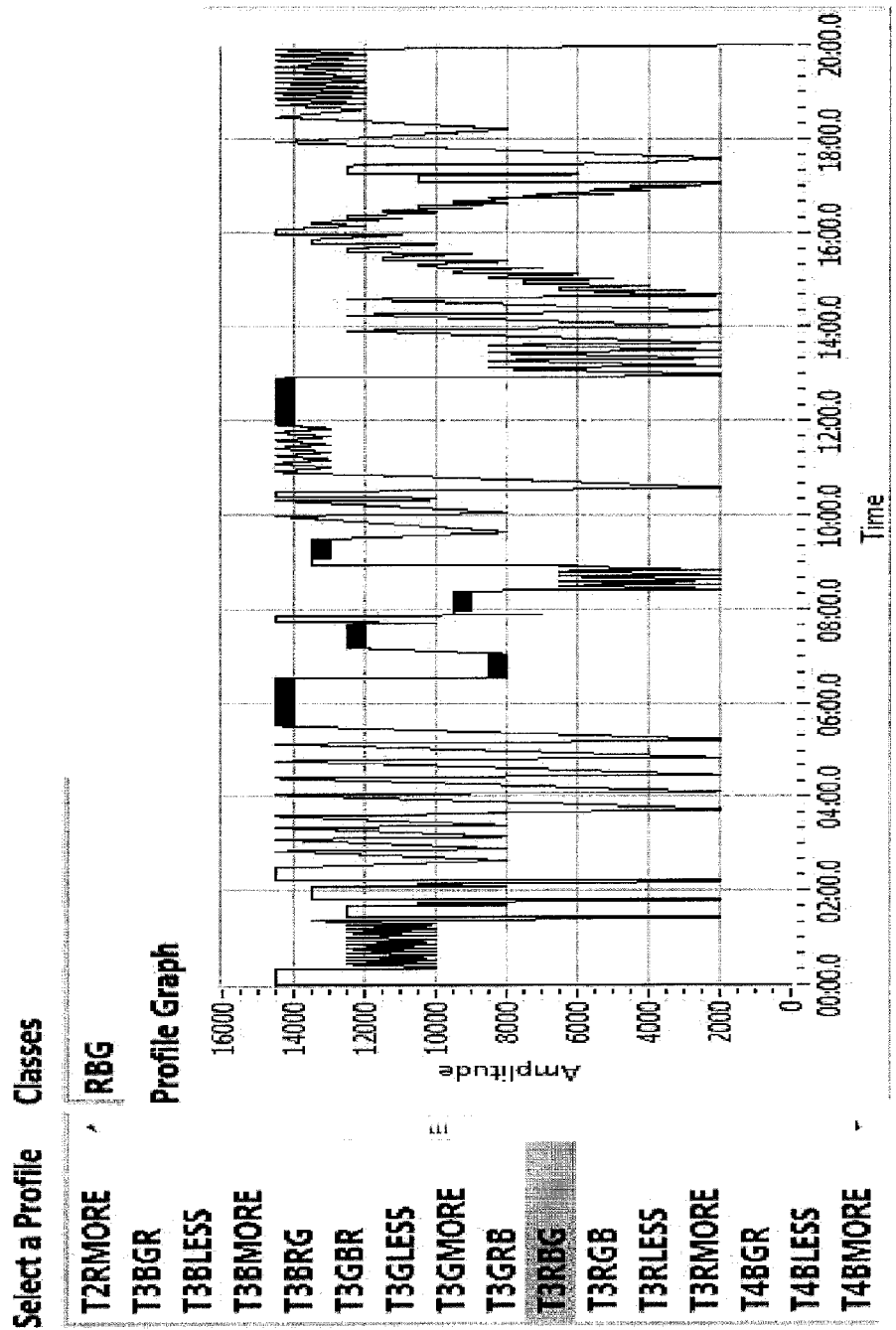
FIG. 9 depicts a graph of the various pressures applied over time during a CVAC session using profile RBG at tier 3.
Figure 10:
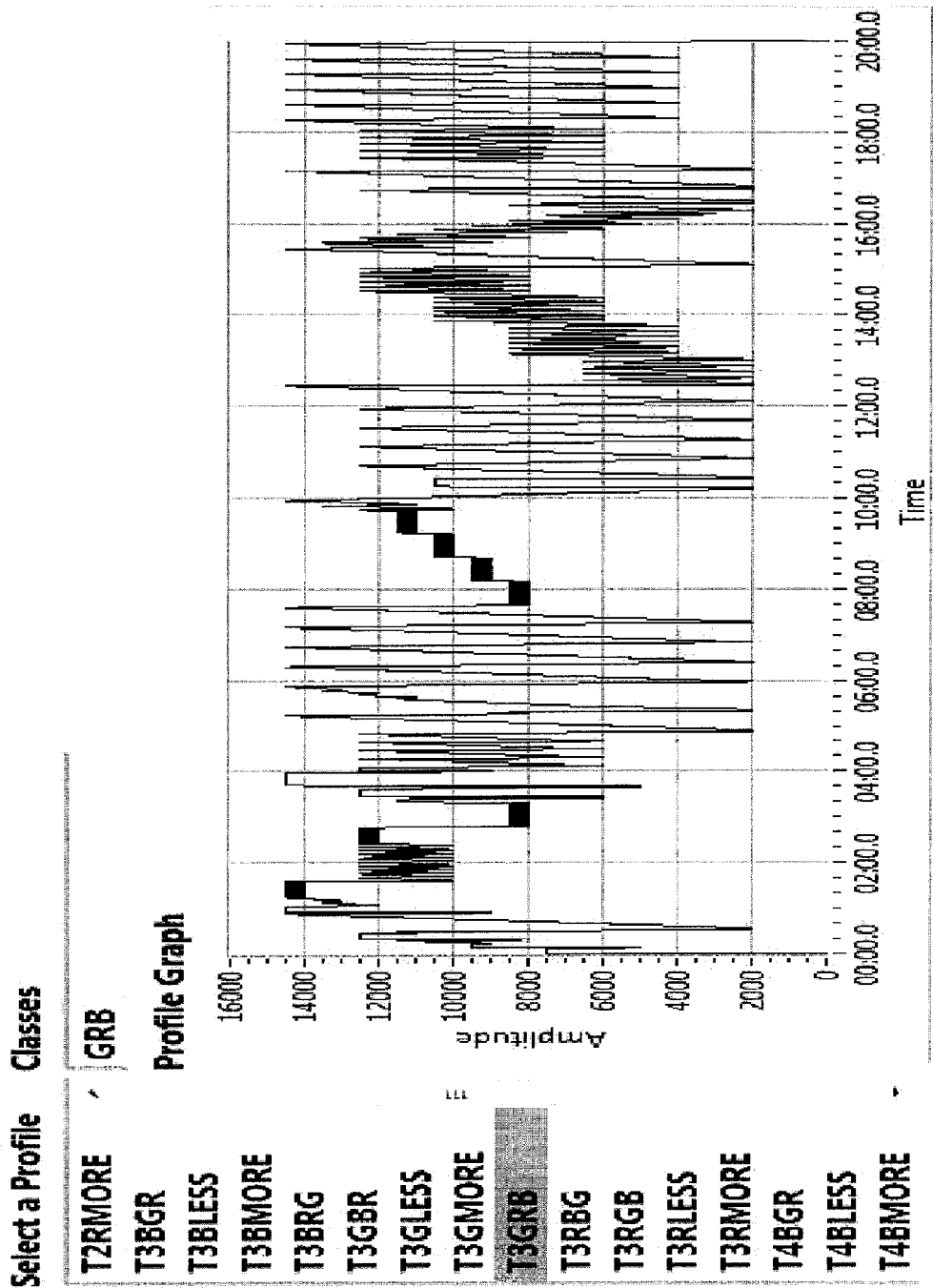
FIG. 10 depicts a graph of the various pressures applied over time during a CVAC session using profile GRB at tier 3.
Figure 11:
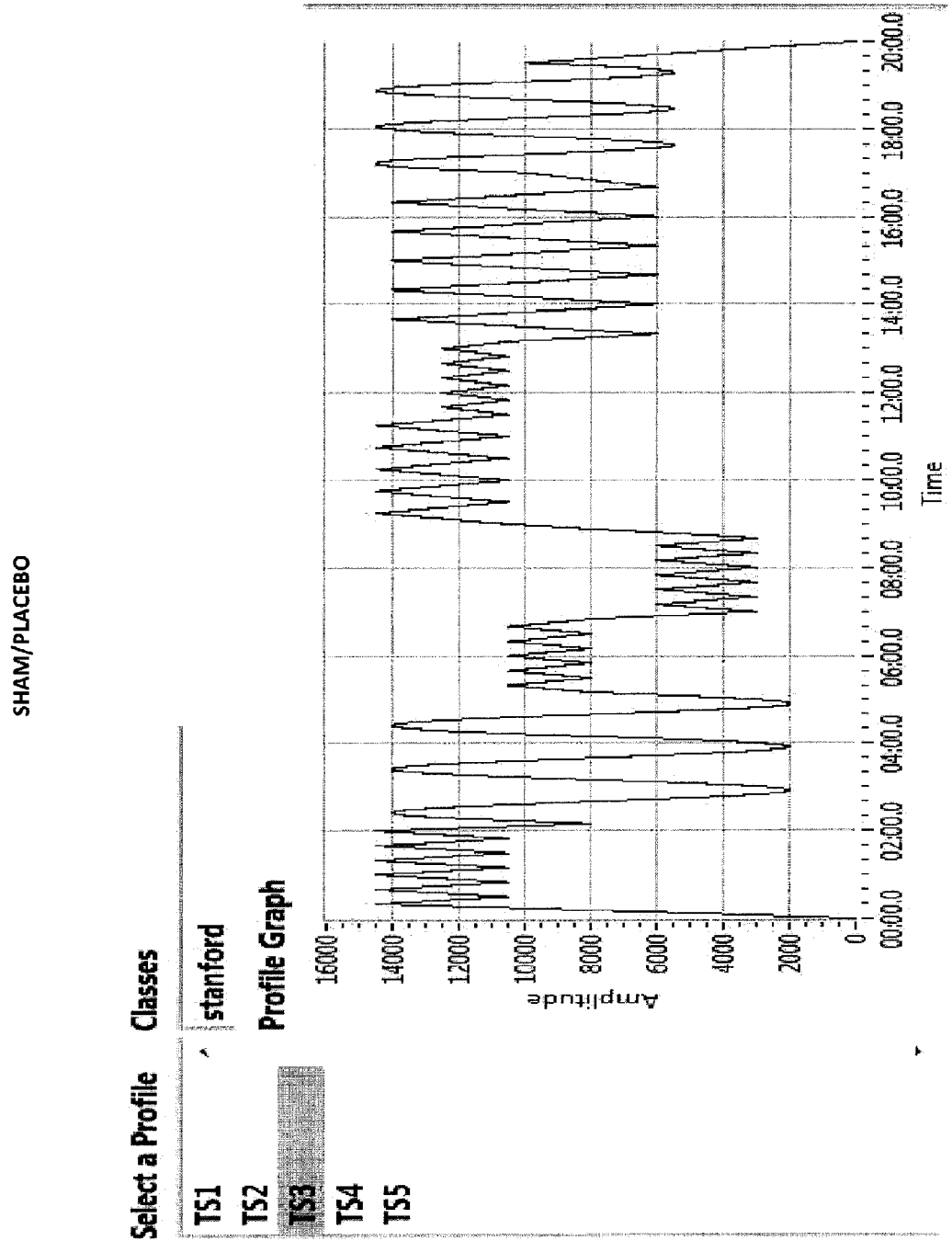
FIG. 11 depicts a graph of the various pressures applied over time during a CVAC session using profile sham at tier 3.
Figure 12:
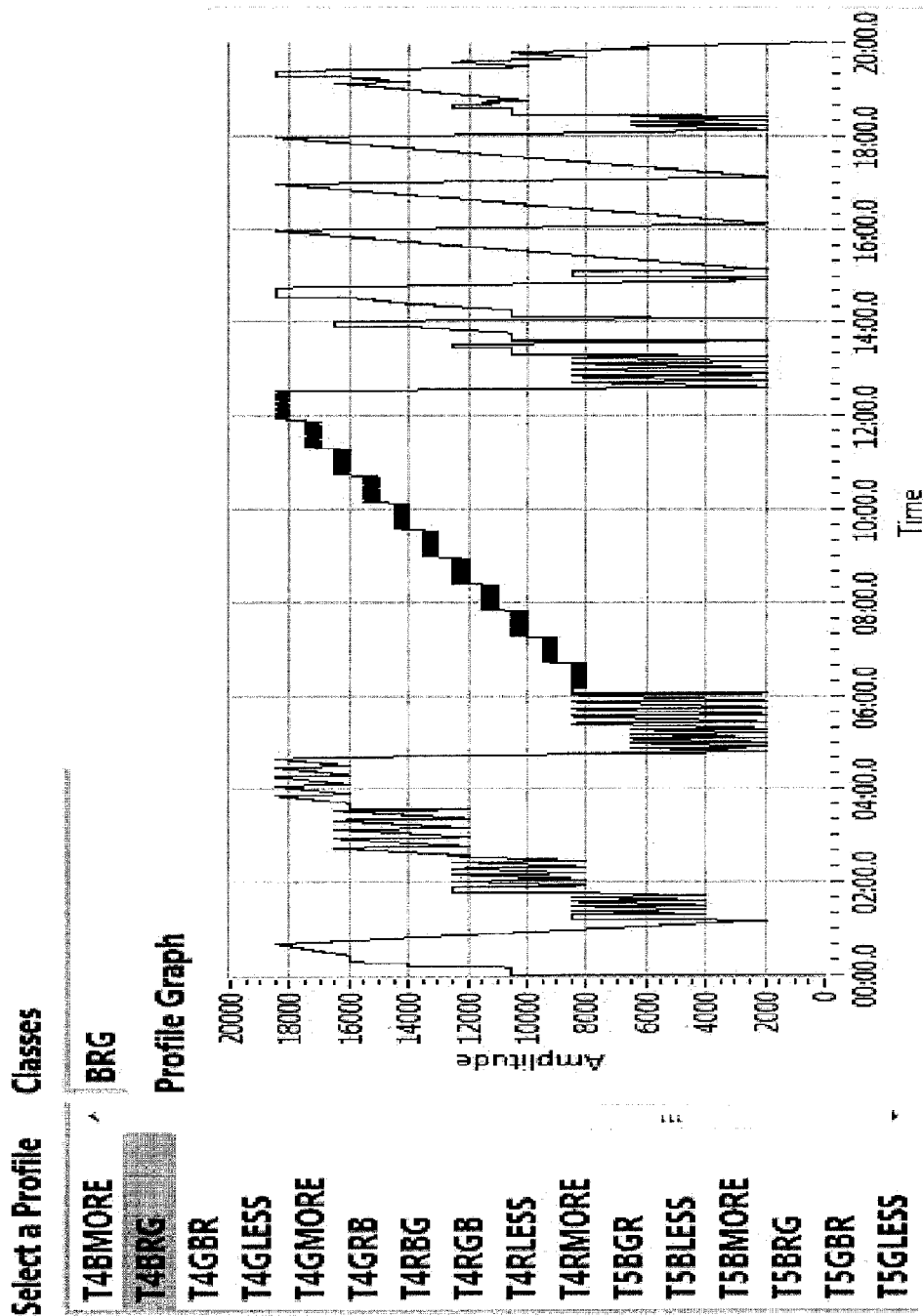
FIG. 12 depicts a graph of the various pressures applied over time during a CVAC session using profile BRG at tier 4.
Figure 13:
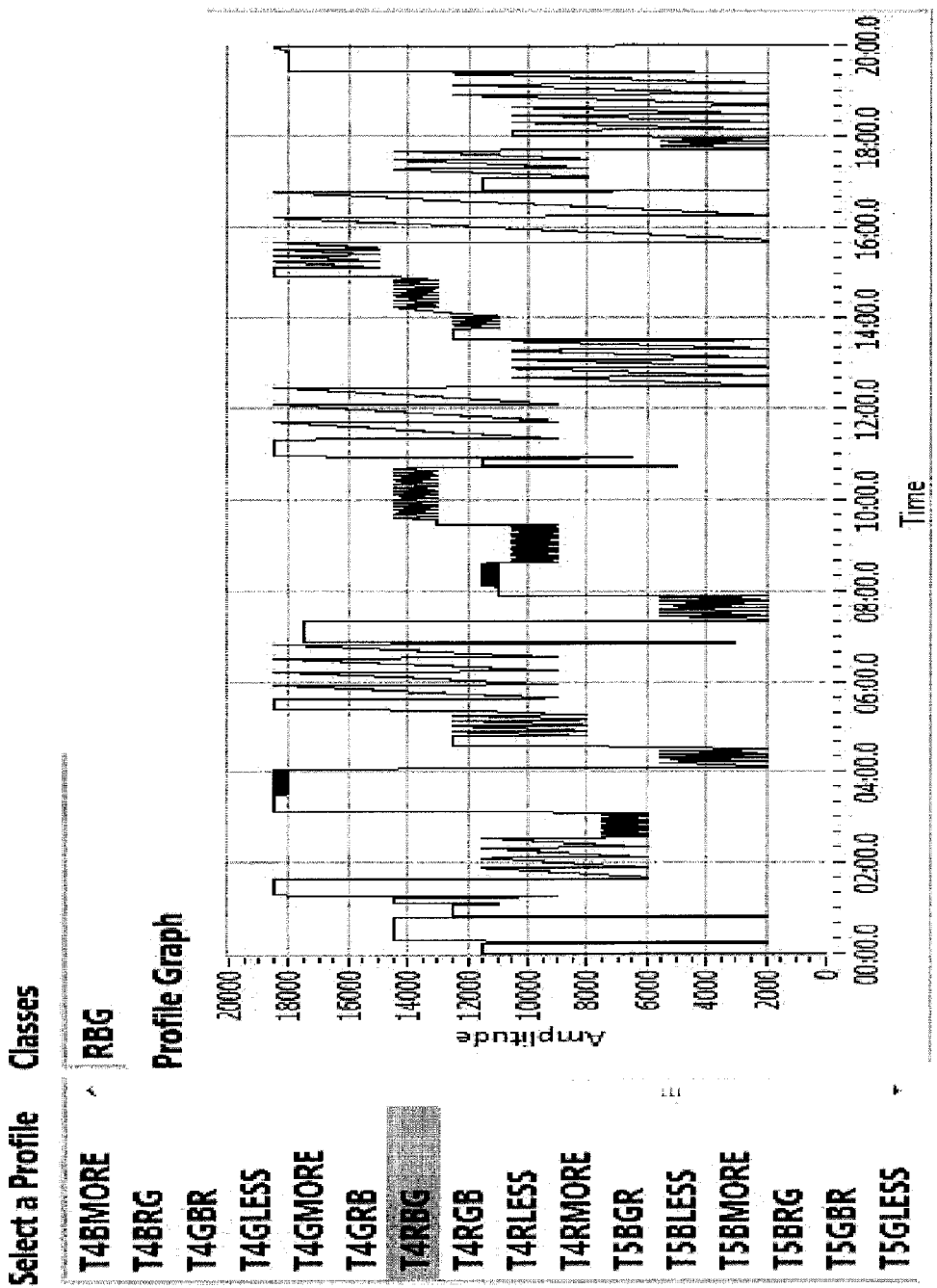
FIG. 13 depicts a graph of the various pressures applied over time during a CVAC session using profile RBG at tier 4.
Figure 14:
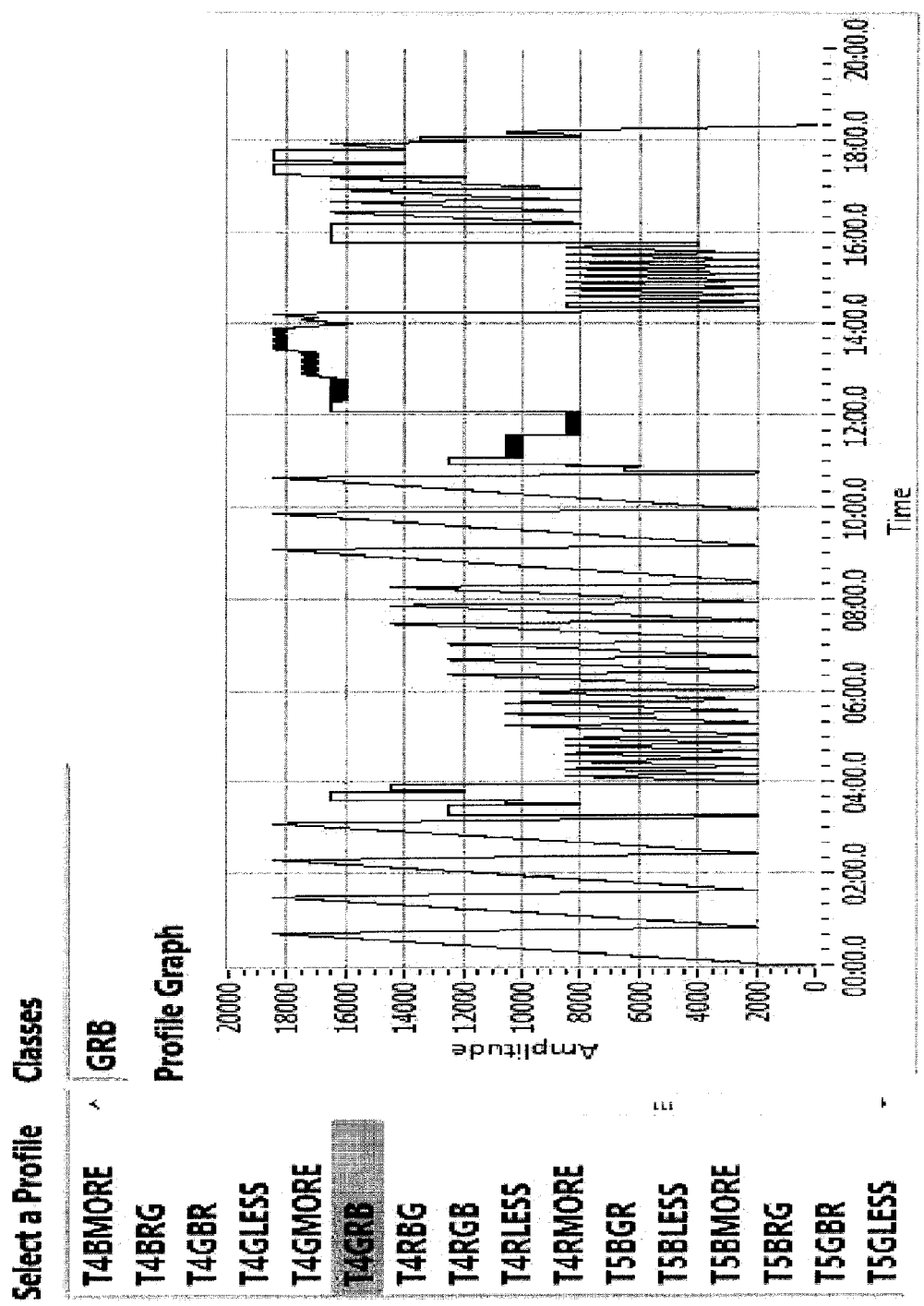
FIG. 14 depicts a graph of the various pressures applied over time during a CVAC session using profile GRB at tier 4.
Figure 15:
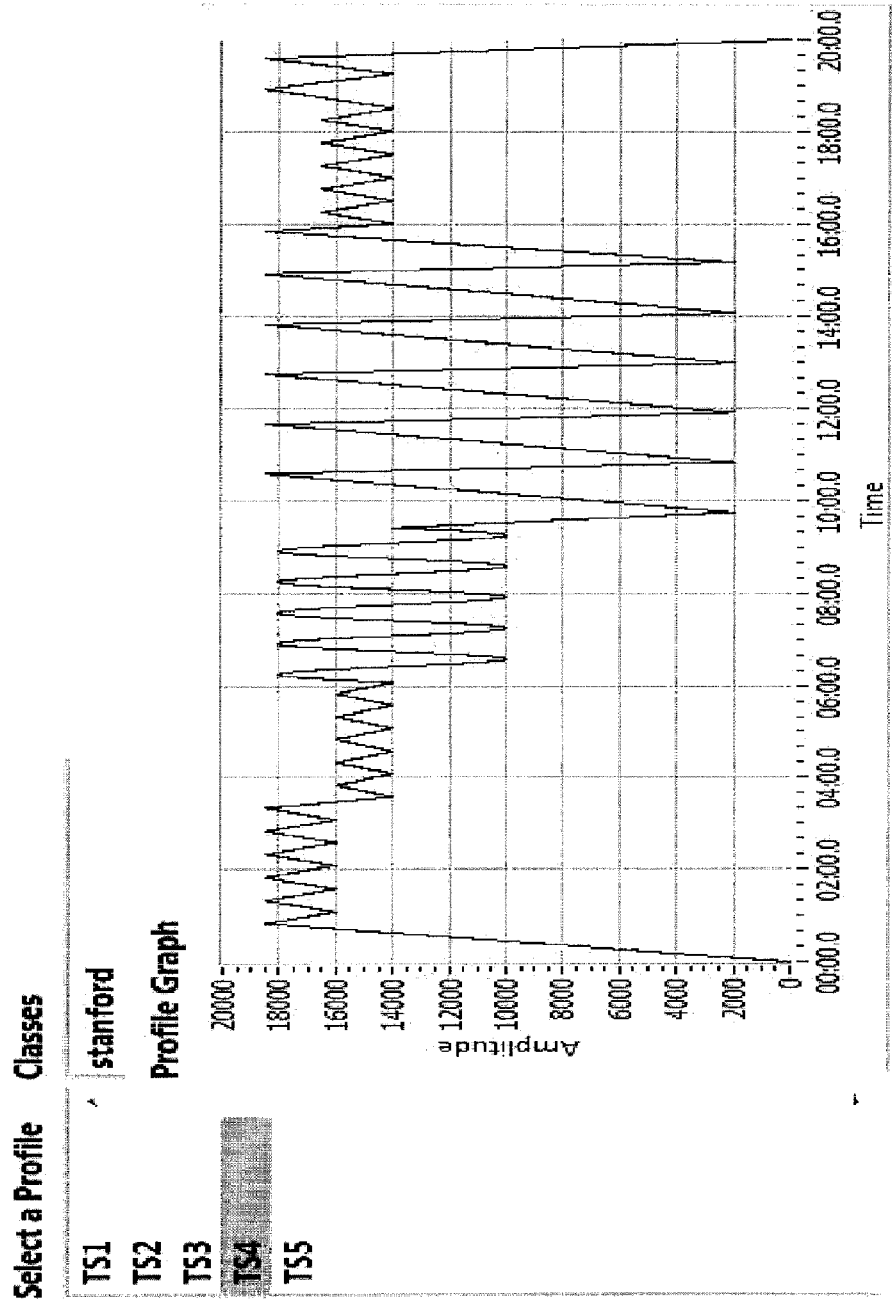
FIG. 15 depicts a graph of the various pressures applied over time during a CVAC session using profile sham at tier 4.
Figure 16:
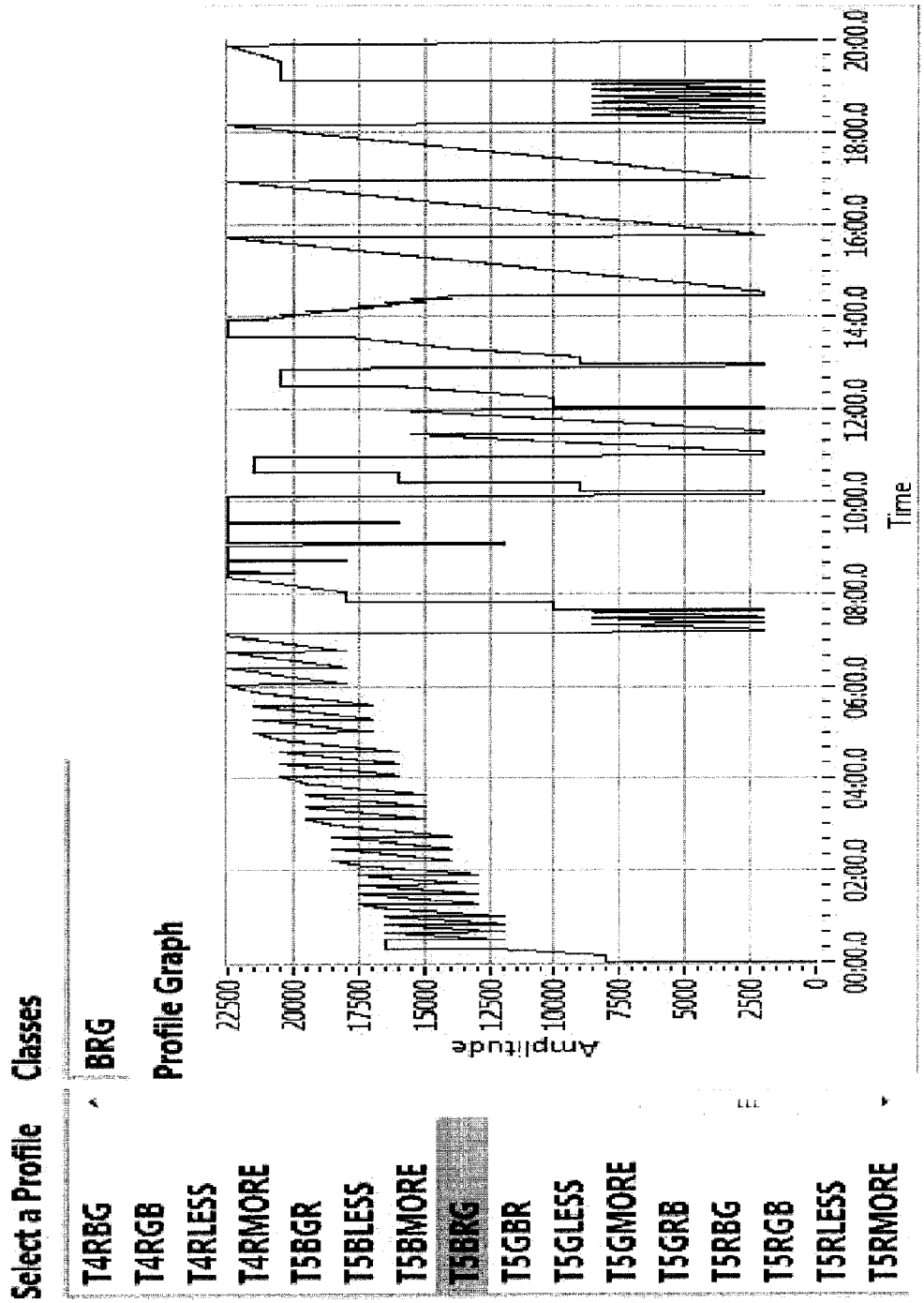
FIG. 16 depicts a graph of the various pressures applied over time during a CVAC session using profile BRG at tier 5.
Figure 17:
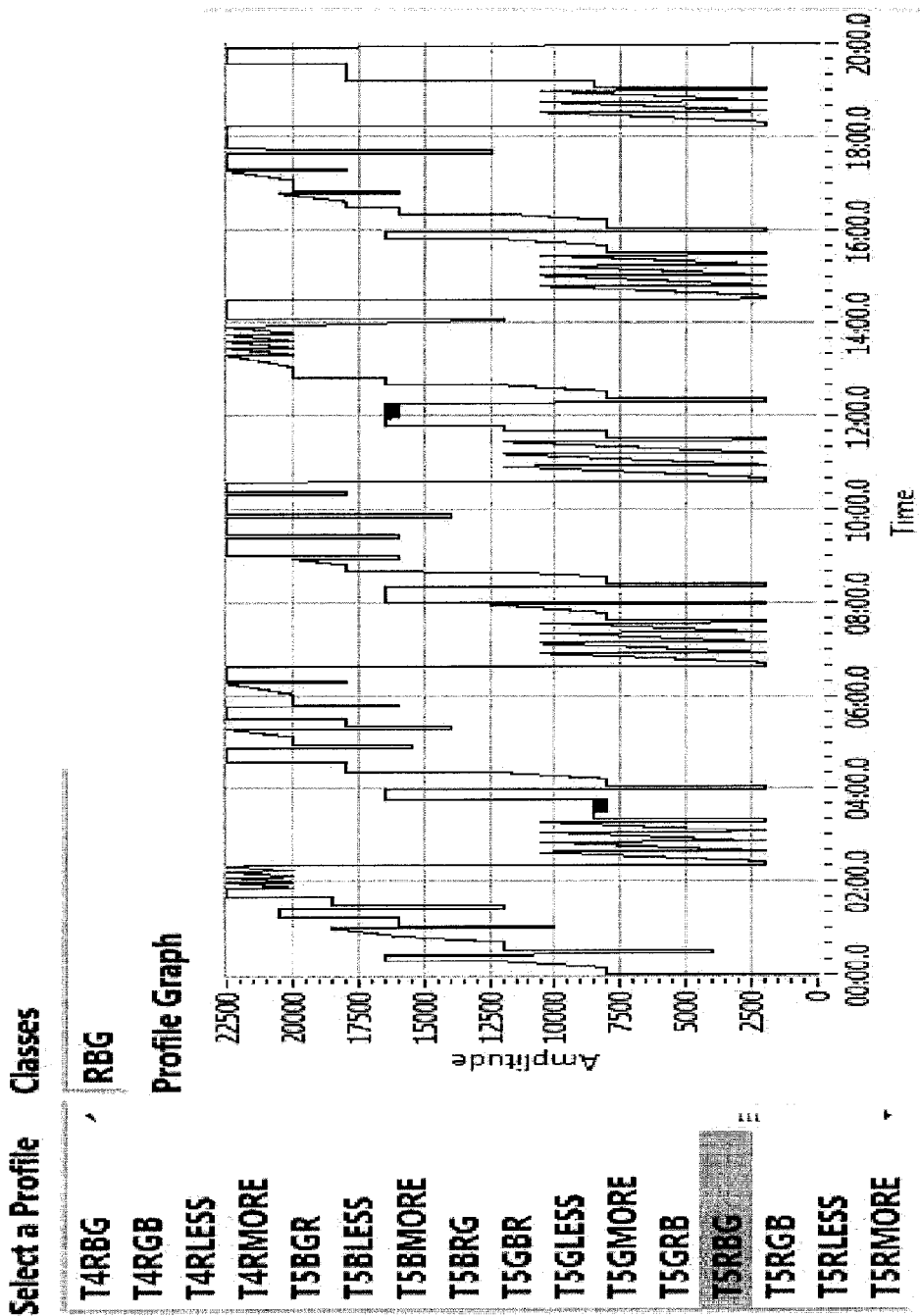
FIG. 17 depicts a graph of the various pressures applied over time during a CVAC session using profile RBG at tier 5.
Figure 18:
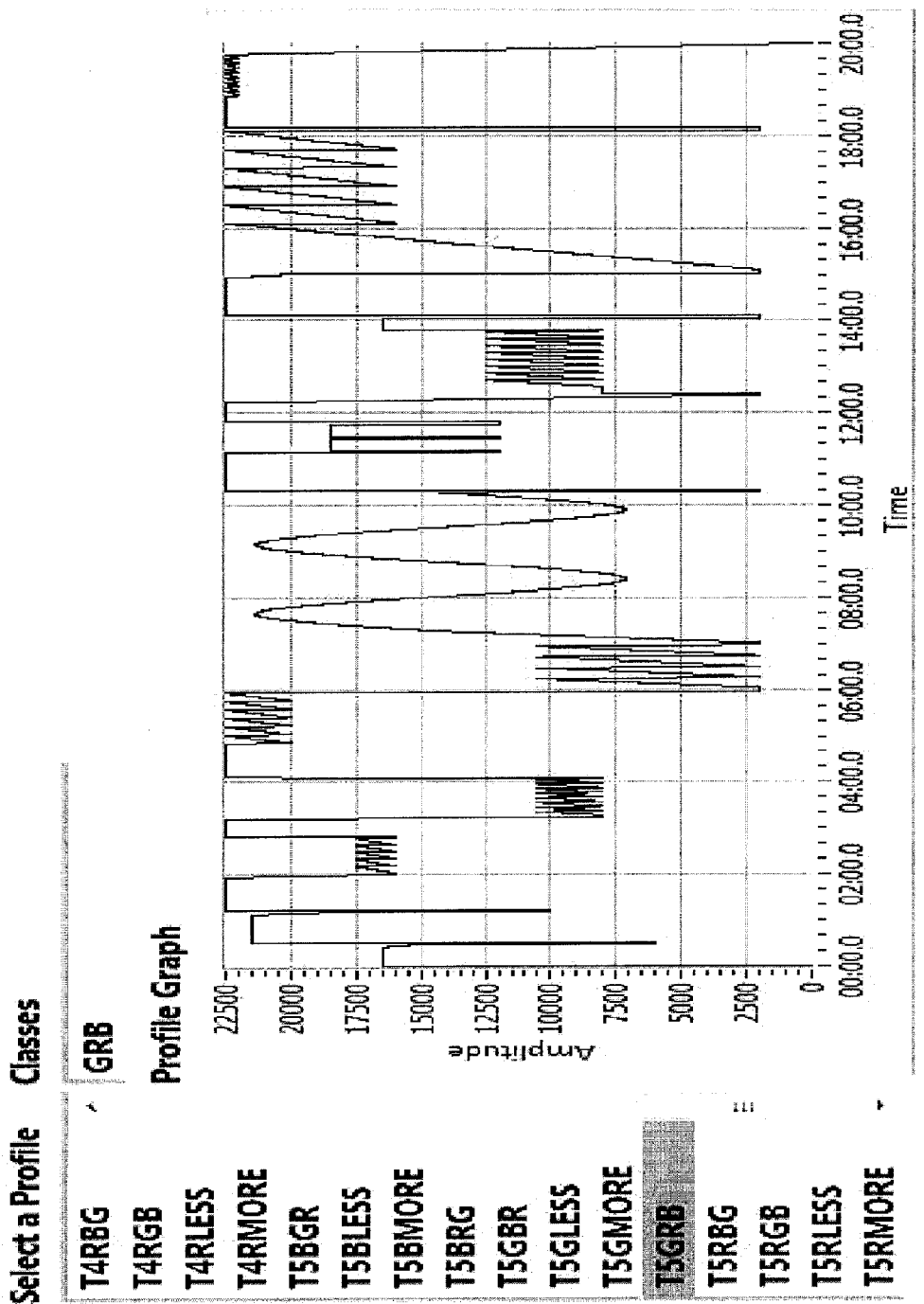
FIG. 18 depicts a graph of the various pressures applied over time during a CVAC session using profile GRB at tier 5.
Figure 19:
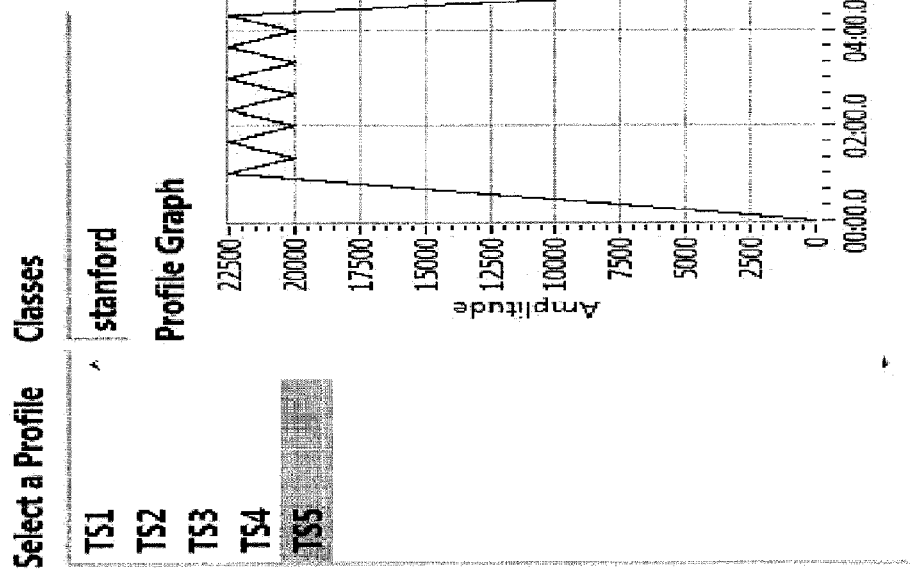
FIG. 19 depicts a graph of the various pressures applied over time during a CVAC session using profile sham at tier 5.
Figure 20:
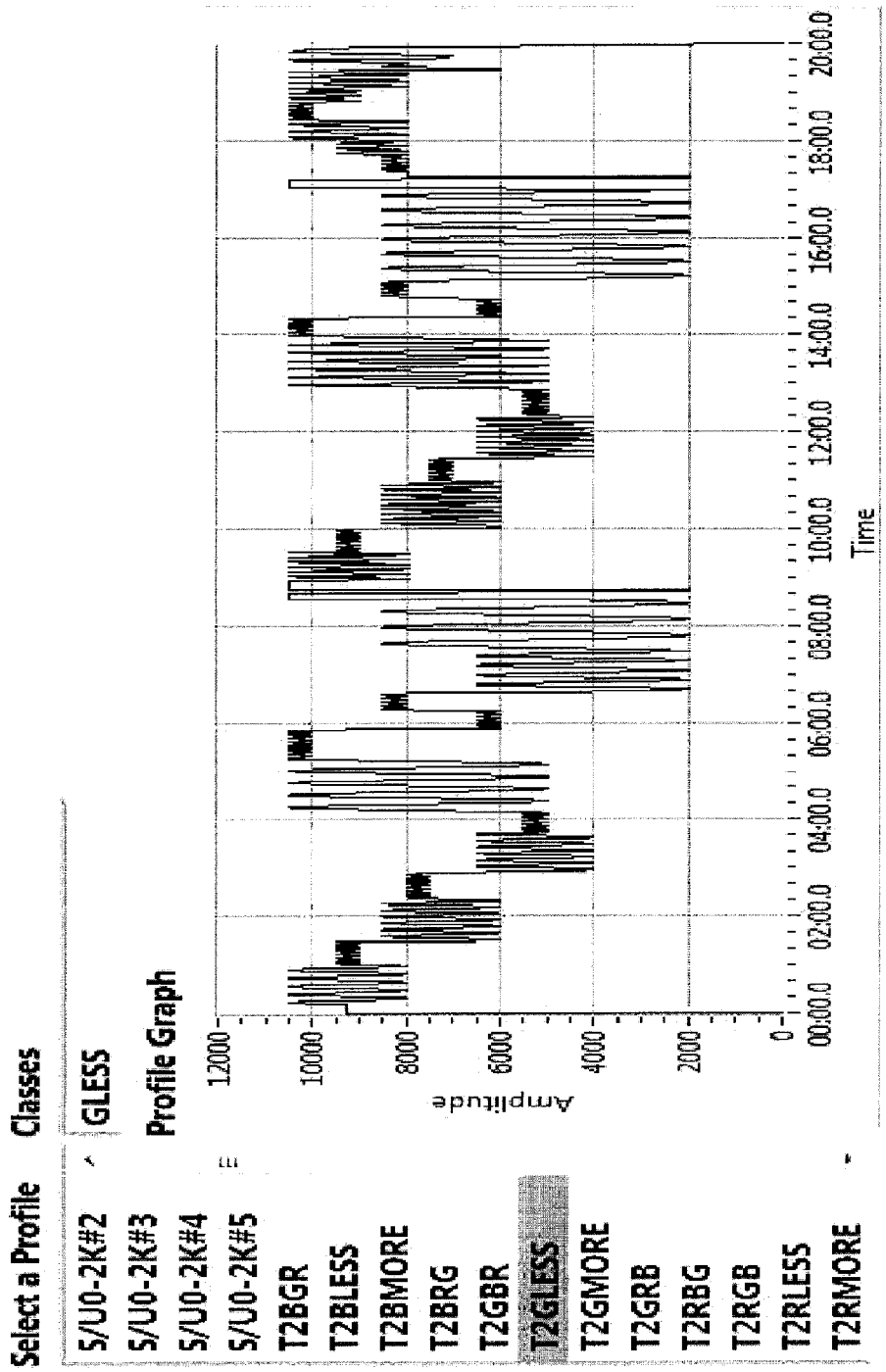
FIG. 20 depicts a graph of the various pressures applied over time during a CVAC session using profile GLESS at tier 2.
Figure 21:
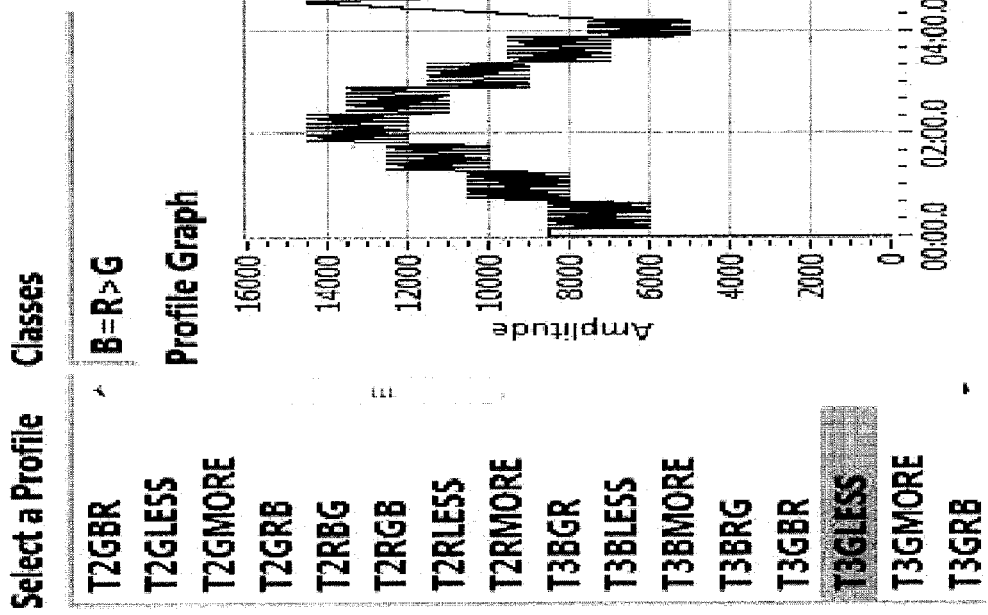
FIG. 21 depicts a graph of the various pressures applied over time during a CVAC session using profile GLESS at tier 3.
Figure 22:
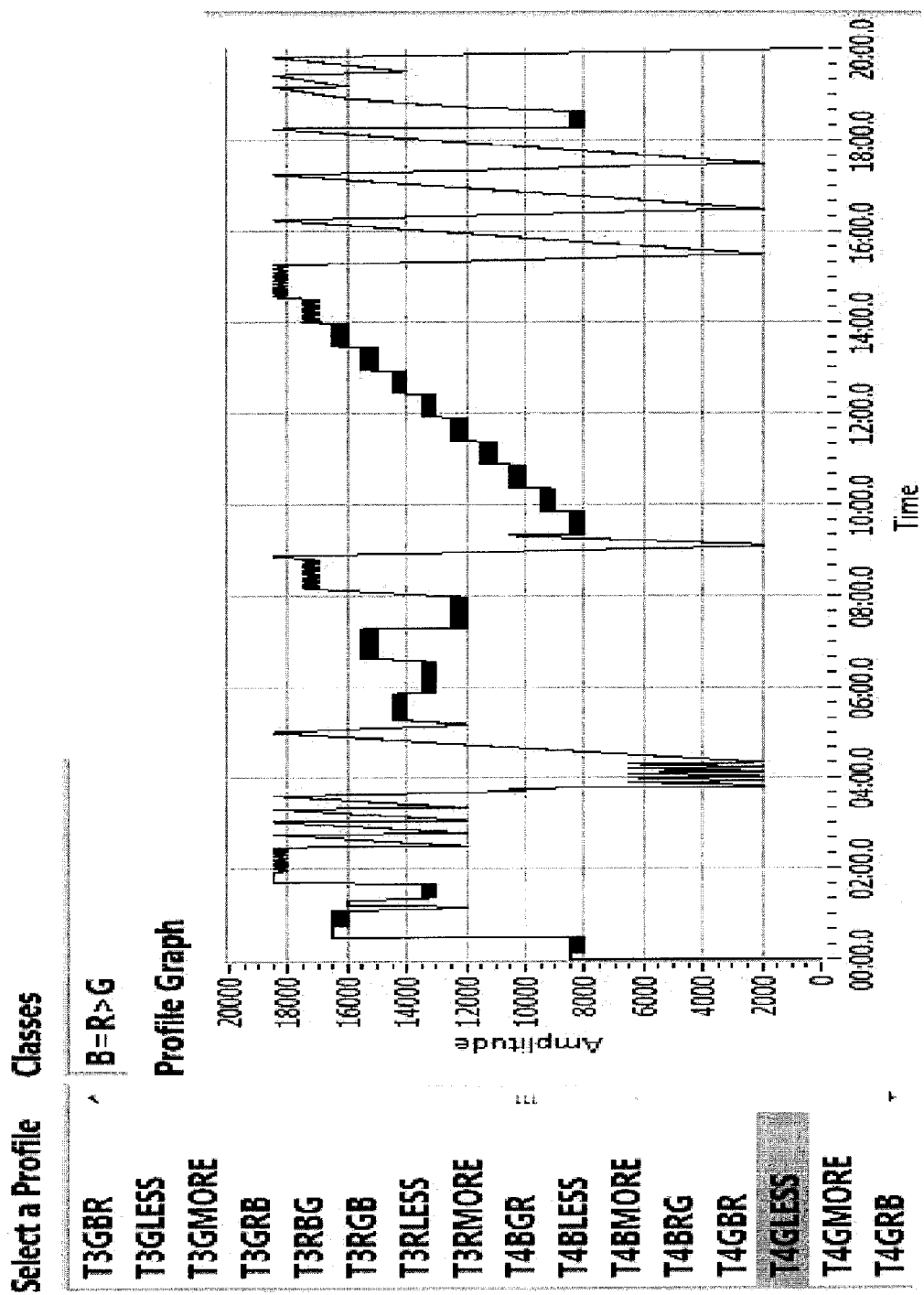
FIG. 22 depicts a graph of the various pressures applied over time during a CVAC session using profile GLESS at tier 4.
Figure 23:
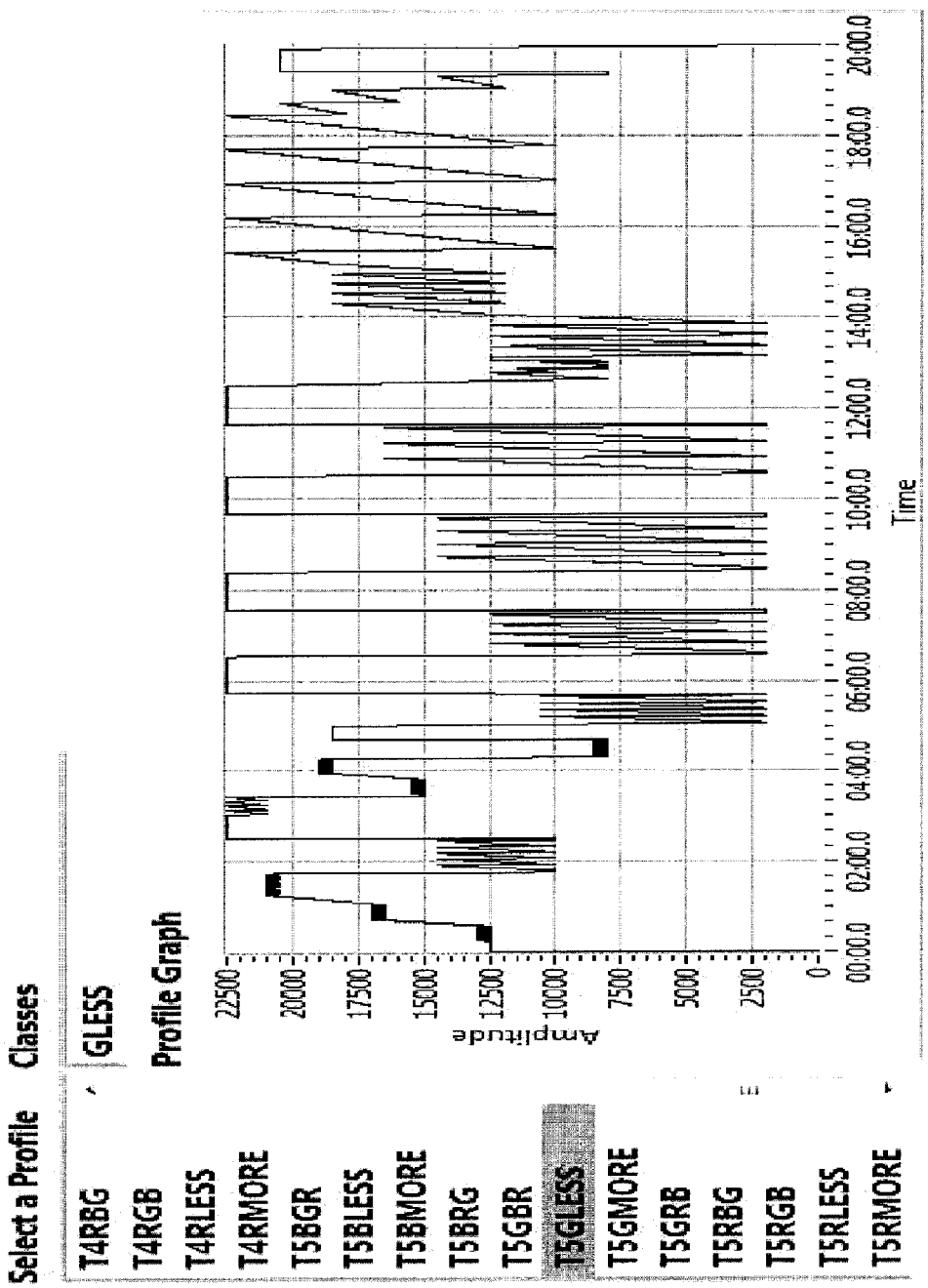
FIG. 23 depicts a graph of the various pressures applied over time during a CVAC session using profile GLESS at tier 5.
Figure 24:
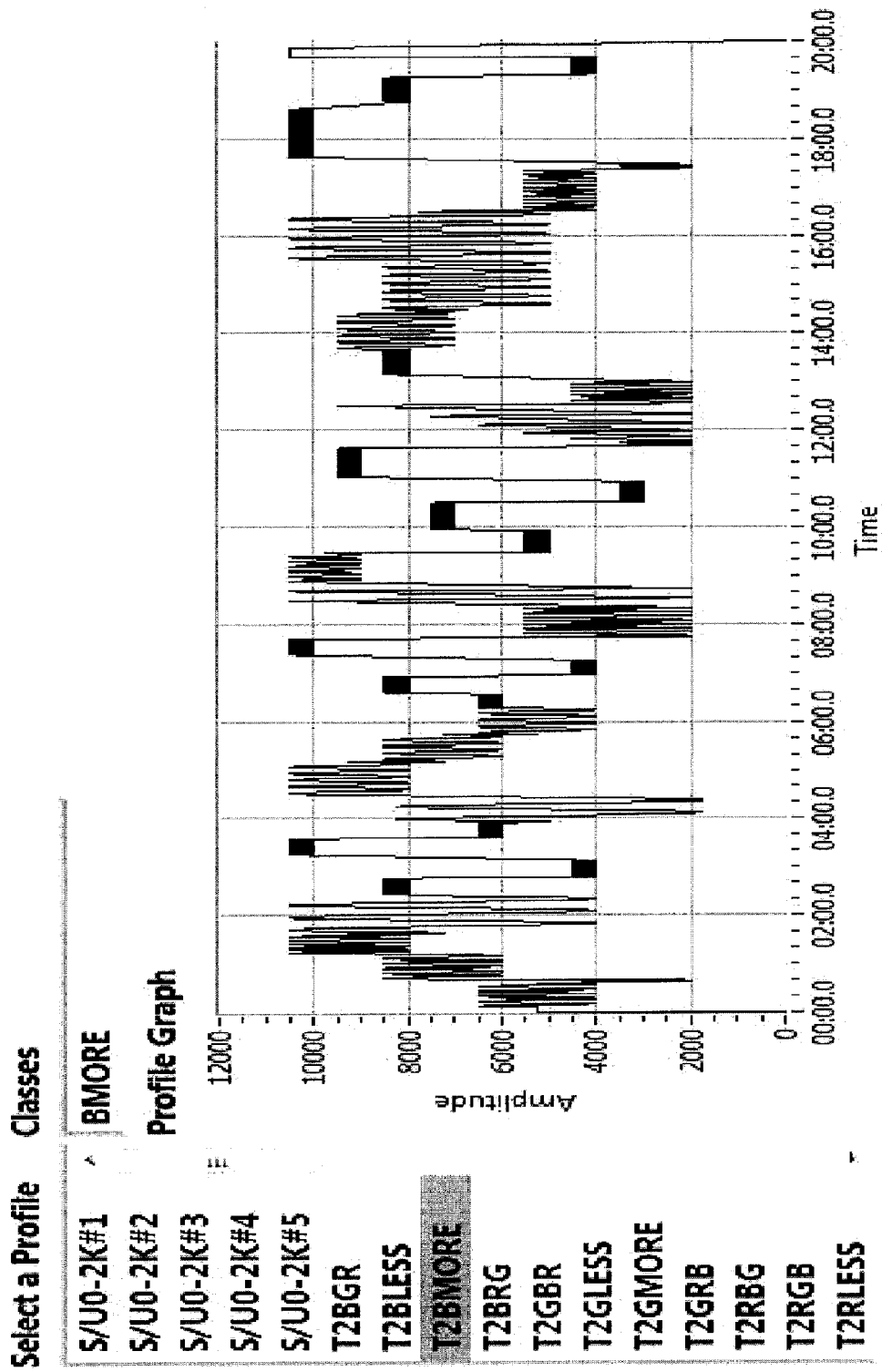
FIG. 24 depicts a graph of the various pressures applied over time during a CVAC session using profile BMORE at tier 2.
Figure 25:
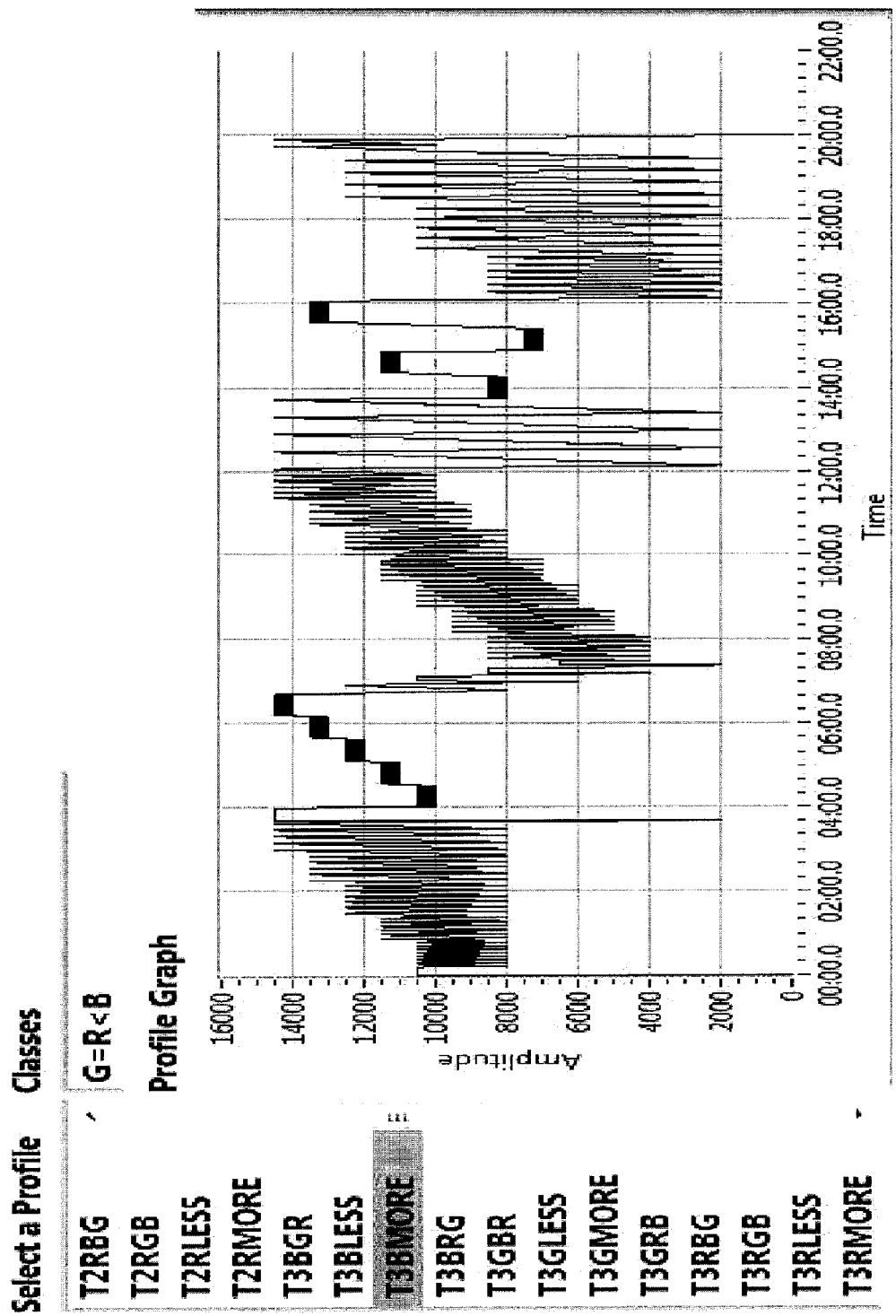
FIG. 25 depicts a graph of the various pressures applied over time during a CVAC session using profile BMORE at tier 3.
Figure 26:
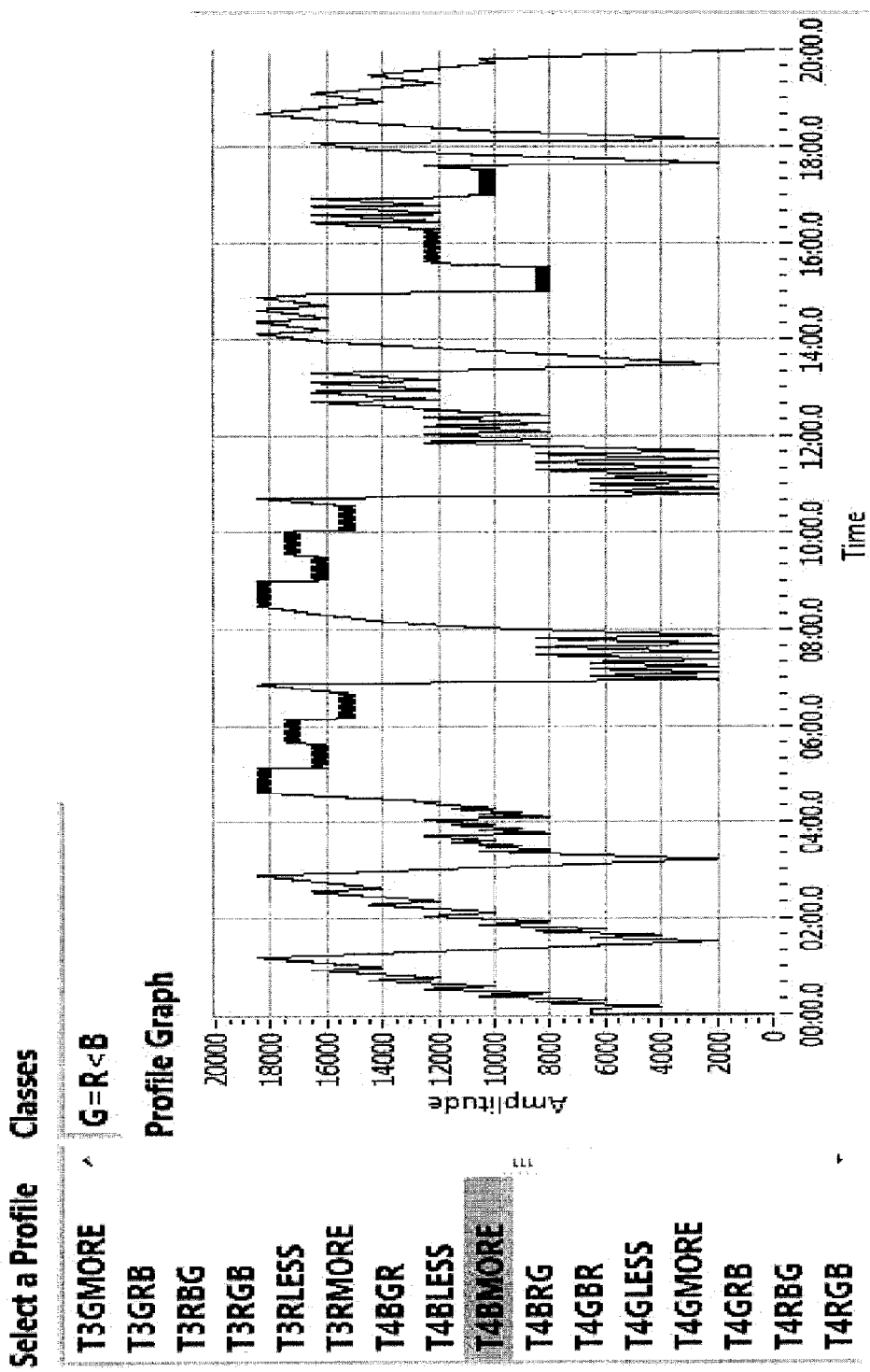
FIG. 26 depicts a graph of the various pressures applied over time during a CVAC session using profile BMORE at tier 4.
Figure 27:
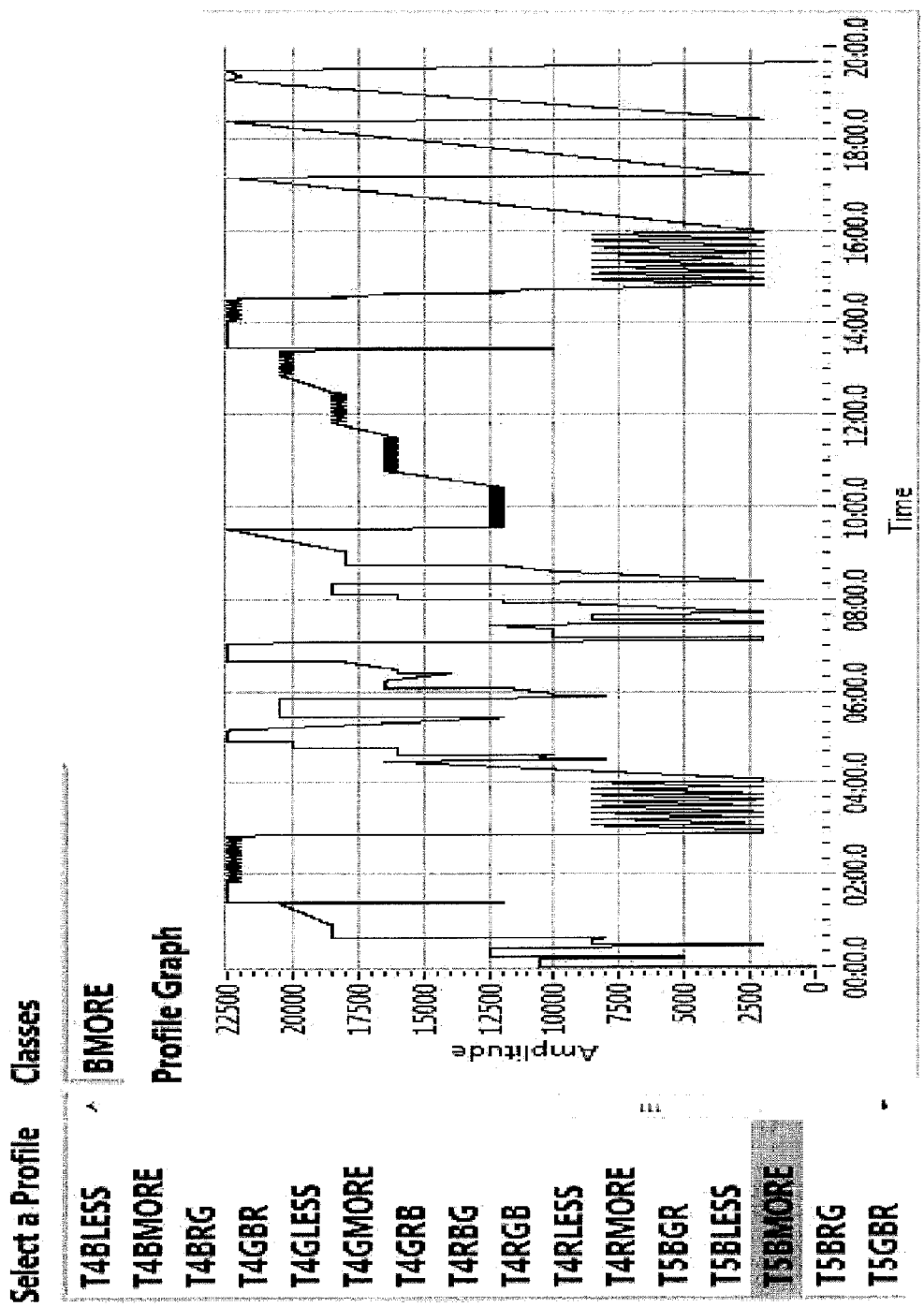
FIG. 27 depicts a graph of the various pressures applied over time during a CVAC session using profile BMORE at tier 5.
Figure 28:
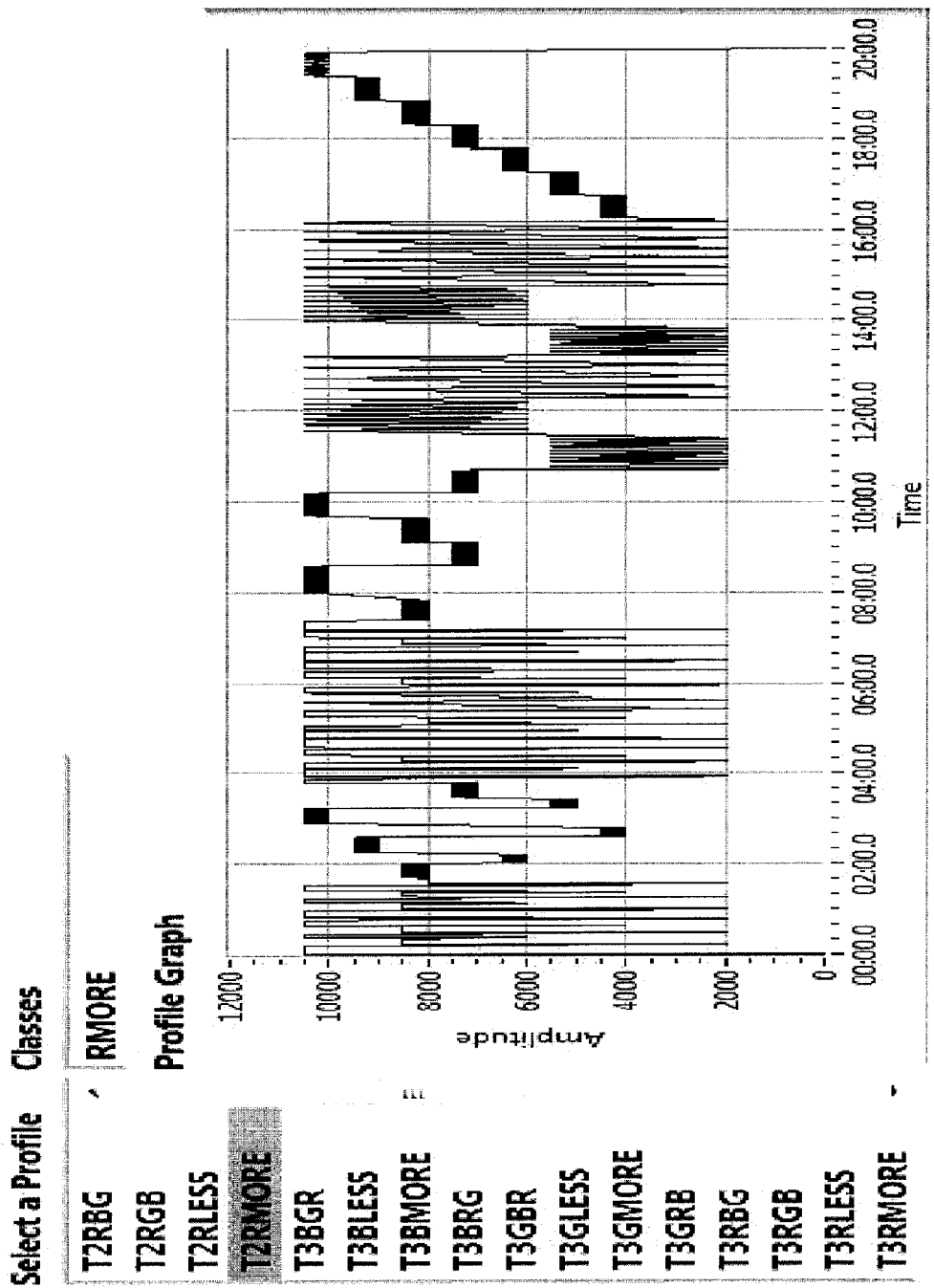
FIG. 28 depicts a graph of the various pressures applied over time during a CVAC session using profile RMORE at tier 2.
Figure 29:
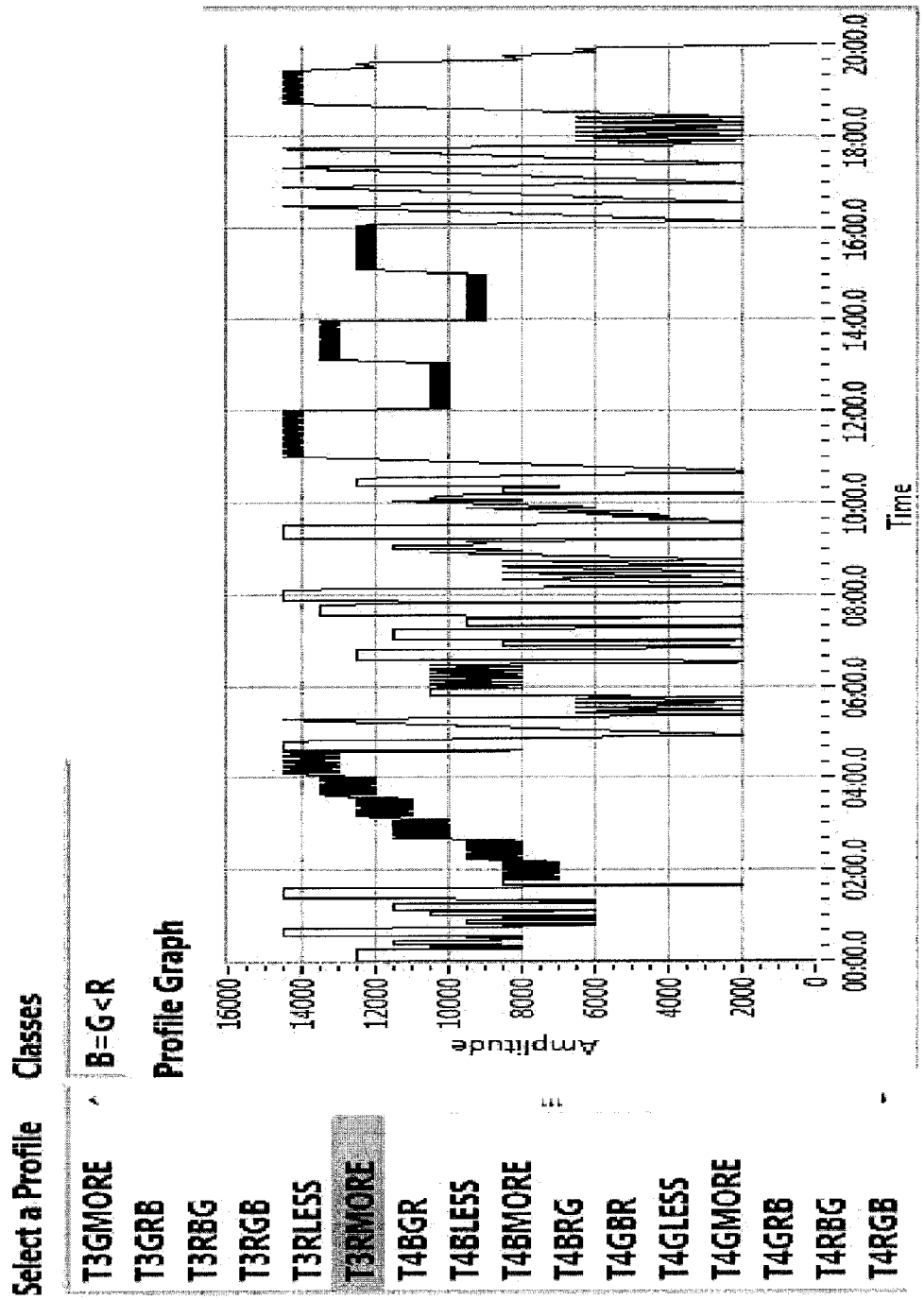
FIG. 29 depicts a graph of the various pressures applied over time during a CVAC session using profile RMORE at tier 3.
Figure 30:
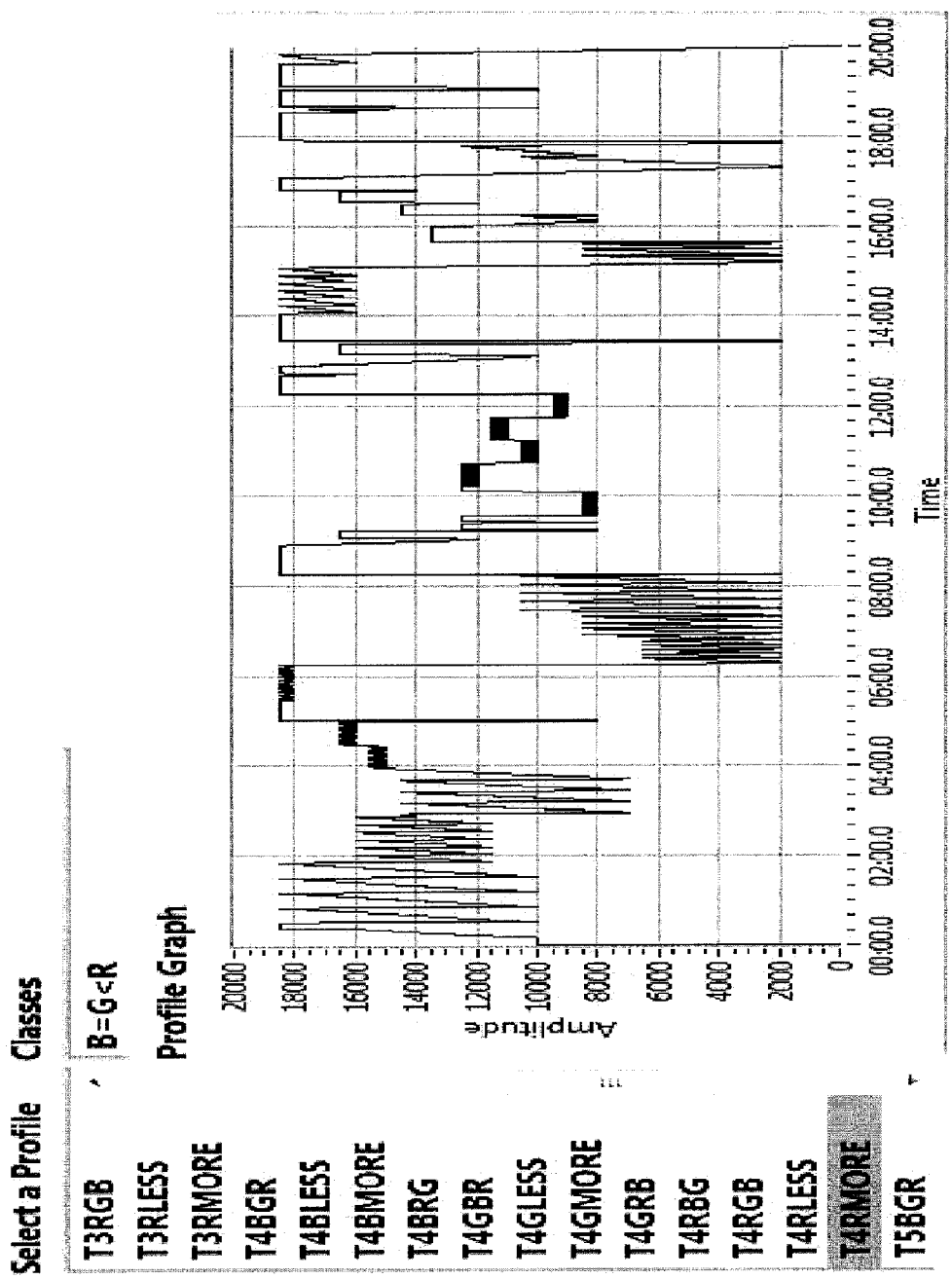
FIG. 30 depicts a graph of the various pressures applied over time during a CVAC session using profile RMORE at tier 4.
Figure 31:
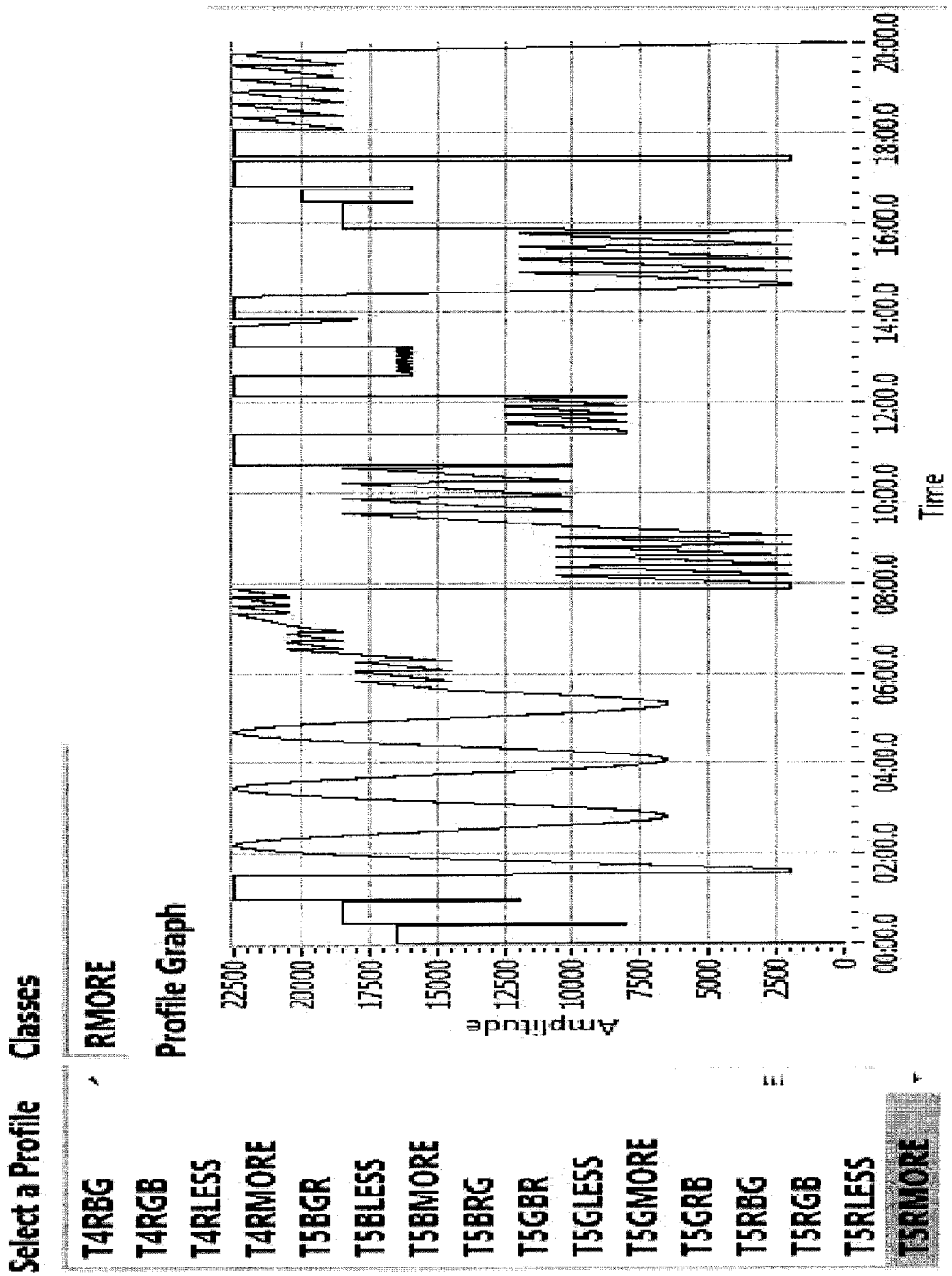
FIG. 31 depicts a graph of the various pressures applied over time during a CVAC session using profile RMORE at tier 5.

Two diabetic subjects (Type-1 and Type-2) were administered 20 minute CVAC sessions, three times a week over a 9 week period. Subject #1 was administered a rotation classified as GLESS, which comprised profiles, for tiers 2 and 3 respectively, GLESS (FIGS. 20, 21), BMORE (FIGS. 24, 25), RMORE (FIGS. 28, 29), RBG (FIGS. 5, 9), and BRG (FIGS. 4, 8). Subject #2 was administered a rotation classified as BRG, which comprised profiles BRG (FIGS. 4, 8), RBG (FIGS. 5, 9), GLESS (FIGS. 20, 21), RMORE (FIGS. 28, 29), and BMORE (FIGS. 24, 25). Triglicerides (TGC), Cholesterol levels (HDL and LDL), and Hemoglobin A1e levels were assessed during the study period. Subject #1 underwent additional CVAC sessions and was additionally assessed at a 14-week time-point. Study time periods and results are shown in Table 1.

TABLE 1

| Physiological Marker | Baseline | | 9 Weeks | | 14 Weeks | |
| --- | --- | --- | --- | --- | --- | --- |
| | Subject #1 | Subject #2 | Subject #1 | Subject #2 | Subject #1 | Subject #2 |
| Triglycerides (TGC) | 102 | 81 | 118 | 85 | 101 | n/d* |
| HDL | 49 | 72 | 49 | 76 | 49 | n/d* |
| LDL | 106 | 111 | 67 | 99 | 84 | n/d* |
| HbA1c | 6.7 | 8.4 | 6.8 | 7.6 | 7.1 | n/d* |
| (LDL + TGC)/HDL | 4.2 | 2.7 | 3.8 | 2.4 | 2.1 | n/d* |

Subject #1: Type-2 diabetic, female
Subject #2: Type-1 diabetic, male
*n/d = not determined The results from the two different subjects show a decrease in their (LDL+TGC)/HDL ratios, indicating improvement in HDL as well as reductions in LDL and/or TGC. Thus in this study, the administration of CVAC sessions resulted in a greater than 10% reduction in the (LDL+TGC)/HDL ratio in subject #2, and a 50% reduction in subject #1. Further, CVAC successfully reduced the LDL and TGC levels of both diabetic individuals, and raised the HDL levels in the diabetic individuals. Thus, in some embodiments, the application of at least one CVAC session may result in at least a 5% reduction in the (LDL+TGC)/HDL ratio, at least a 5-10% reduction in the (LDL+TGC)/HDL ratio, or greater than a 10% reduction in the (LDL+TGC)/HDL ration.

Example 3

A 36 year old male was administered CVAC sessions for 40 minutes (two twenty-minute CVAC sessions administered in immediate succession), 4 times a week for 12 weeks. In this study, the CVAC session rotation was classified as RBG which included five profiles, for tiers 2-5, RBG (FIGS. 5, 9, 13, and 17), BRG (FIGS. 4, 8, 12, and 16), RMORE (FIGS. 28, 29, 30, and 31), GLESS (FIGS. 20, 21, 22, and 23), and RBG again. Testosterone (T) levels, total testosterone levels (TT), LDL levels (LDL), Total Cholesterol (C), and Insulin levels (I) were assessed. Results of physical markers prior to CVAC treatment and after CVAC treatment are shown in Table 2.

TABLE 2

| | 3 months prior to CVAC treatment | 3 months after beginning CVAC treatment |
| --- | --- | --- |
| Physiological Marker | Subject #1 | Subject #1 |
| Free Testosterone (T) | 80 | 177 |
| Total Testosterone (TT) | 298 | 706 |
| Total Cholesterol (C) | 275 | 258 |
| Serum LDL | 208 | 191 |
| Serum Insulin (I) | 5.0 | 2.0 |

The results of the study demonstrate that CVAC administration increased T levels while also decreasing LDL, C, and I. Specifically, LDL was reduced by 9%, T was increased by 121%, TT was increased by 58%, and I was reduced by 60%. Thus, in some embodiments, the application of at least one CVAC session may result in at least a 10% increase in T, at least a 20% increase in T, at least a 30% increase in T, at least a 40% increase in T, at least a 50% increase in T, at least a 75% increase in T, at least a 100% increase in T, or greater than a 100% increase in T. Similarly, the application of at least one CVAC session may result in at least a 1% reduction in LDL, at least a 2% reduction in LDL, at least a 3% reduction in LDL, at least a 4% reduction in LDL, at least a 5% reduction in LDL, at least a 10% reduction in LDL, or greater than a 10% reduction in LDL. The application of at least one CVAC session may further result in at least a 1% reduction in serum insulin, at least a 5% reduction in serum insulin, at least a 10% reduction in serum insulin, at least a 20% reduction in serum insulin, at least a 30% reduction in serum insulin, at least a 60% reduction in serum insulin, or greater than a 60% reduction in serum insulin.

Example 4

Effect of CVAC exposure of 40 minutes twice a week on endogenous testosterone. Six subjects (S-1, S-3, S-6, M-9, M-18, and M-23) and a control subject (M-14) are administered two twenty-minute CVAC sessions, administered in immediate succession, twice a week throughout the study period. The CVAC sessions experienced by each subject consisted of a profile of pressure levels and durations for each pressure level. There were three different profiles used in the study, entitled BRG, RBG, and GRB. Each CVAC session profile cycled through a rotation of the pressures and parameters associated with that given profile. After completing three 20-minute CVAC sessions consisting of a given profile, each subject then switched to a second CVAC session profile. The subjects then experienced three CVAC sessions of this second profile before switching to the third CVAC session profile. After completion of three CVAC sessions based on the third profile, the subject then returned to the first profile, with each profile be repeated in triad form. All CVAC sessions, regardless of the profile used, had a pressure ceiling corresponding to a specific tier. Subjects then progressed through tiers 2-5, and each tiered level included a maximum pressure ceiling that corresponded to an altitude of 4000 feet higher than the previous tier. A subject was not allowed to switch to the next higher tier until the subject had experienced fifteen CVAC sessions at the lower tier. Sham sessions (or control sessions) correspond to the cycling of the five tier levels but do not contain any meaningful pressure changes (e.g. pressure changes equivalent to altitude of 2000 feet with very few changes in duration), thus the subjects experience the CVAC session for the equivalent 20 minute session, but without the pressure changes and durations. In this study, profiles BRG (FIGS. 4, 8, 12, and 16), RBG (FIGS. 5, 9, 13, and 17), GRB (FIGS. 6, 10, 14, and 18) (tiers 2-5 respectively) were administered in sequential order for tiers 2-5 as described above. Sham sessions corresponding to tiers 2, 3, 4, and five (FIGS. 7, 11, 15, and 19) were administered where indicated and the graphical representations corresponding to pressures are not indicative of the pressure changes in the CVAC unit. The simulated graphical output was for control purposes to keep the subjects blinded to the sham sessions.

Blood samples were drawn prior to beginning the study period and after the final CVAC session at the end of the study period. Blood samples were analyzed for total testosterone, free testosterone, and the ratio of total testosterone to free testosterone. Results are shown in FIG. 3 (FIG. 3).

Example 5

Effect of CVAC exposure of 40 minutes twice a week on serum lipid levels. Six subjects (S-1, S-3, S-6, M-9, M-18, and M-23) and a control subject (M-14) are administered two twenty-minute CVAC sessions, twice a week for throughout the study period. The CVAC sessions experienced by each subject consisted of a profile of pressure levels and durations for each pressure level. There were three different profiles used in the study, entitled BRG, RBG, and GRB. Each CVAC session profile cycled through a rotation of the pressures and parameters associated with that given profile. After completing three 20-minute CVAC sessions consisting of a given profile, each subject then switched to a second CVAC session profile. The subjects then experienced three CVAC sessions of this second profile before switching to the third CVAC session profile. After completion of three CVAC sessions based on the third profile, the subject then returned to the first profile, with each profile be repeated in triad form. All CVAC sessions, regardless of the profile used, had a pressure ceiling corresponding to a specific tier. Subjects then progressed through tiers 2-5, and each tiered level included a maximum pressure ceiling that corresponded to an altitude of 4000 feet higher than the previous tier. A subject was not allowed to switch to the next higher tier until the subject had experienced fifteen CVAC sessions at the lower tier. Sham sessions (or control sessions) correspond to the cycling of the five tier levels but do not contain any meaningful pressure changes (e.g. pressure changes equivalent to altitude of 2000 feet with very few changes in duration), thus the subjects experience the CVAC session for the equivalent 20 minute session, but without the pressure changes and durations. In this study, profiles BRG (FIGS. 4, 8, 12, and 16), RBG (FIGS. 5, 9, 13, and 17), GRB (FIGS. 6, 10, 14, and 18) (tiers 2-5 respectively) were administered in sequential order for tiers 2-5 as described above. Sham sessions corresponding to tiers 2, 3, 4, and five (FIGS. 7, 11, 15, and 19) were administered where indicated and the graphical representations corresponding to pressures are not indicative of the pressure changes in the CVAC unit. The simulated graphical output was for control purposes to keep the subjects blinded to the sham sessions.

Blood samples were drawn prior to beginning the study period and after the fatal CVAC session at the end of the study period. Blood samples are analyzed for a variety of serum lipid levels including HDL, VLDL, and LDL. The results are summarized in FIG. 2.

The aspects and embodiments of the present invention described above are only examples and are not limiting in any way. Various changes, modifications or alternations to these embodiments may be made without departing from the spirit of the invention and the scope of the claims.

What is claimed is:

1. A method, comprising:
   administering, via a pressure vessel unit, at least one Cyclic Variations in Altitude Conditioning (CVAC) session to a mammal having abnormal serum lipid levels, the CVAC session having a start point of ambient pressure at the delivery site, an end point of ambient pressure at the delivery site, a plurality of pressure targets executed between the start point and the end point, and a plurality of pressure transitions executed between the start point and the end point, each pressure transition from the plurality of pressure transitions connecting a successively executed pair of pressure targets from the plurality of pressure targets, the plurality of pressure transitions including a plurality of pressure increases and a plurality of decreases, each pressure target from the plurality of pressure targets being equivalent to an atmospheric pressure level within the range of between 2,000 feet to 22,500 feet.

2. The method of claim 1, wherein no pressure target from the plurality of pressure targets of the CVAC session is equivalent to an atmospheric pressure level of less than 2,000 feet.

3. The method of claim 1, wherein at least one pressure target from the plurality of pressure targets of the CVAC session is a maximum pressure target equivalent to an atmospheric pressure level of 10,500 feet, 14,500 feet, 18,500 feet, or 22,500 feet.

4. The method of claim 1, wherein the administering is configured to at least one of increase or reduce the serum lipid levels of the mammal.

5. The method of claim 1, further comprising:
   measuring at least one physiological marker associated with the mammal prior to the administering.

6. The method of claim 5, further comprising:
   measuring the at least one physiological marker associated with the mammal after the administering.

7. The method of claim 6, further comprising:
   measuring an efficacy of the at least one CVAC session based on a difference between the at least one physiological marker measured prior to the administering and the at least one physiological marker measured after the administering.

8. The method of claim 5, wherein the physiological marker includes at least one of an androgen, a progestogen, an estrogen, a mineralocorticoid, a glucocorticoid, testosterone, an estradiol, an estriol, or an estrone.

9. The method of claim 5, wherein the physiological marker includes at least one of VLDL, LDL, HDL, cholesterol or erythropoietin production.

10. The method of claim 5, wherein the physiological marker includes a steroid level, the administering configured to increase the steroid level.

11. The method of claim 5, wherein the physiological marker includes glucose tolerance.

12. The method of claim 1, wherein a duration of the CVAC session does not exceed 20 minutes.

13. The method of claim 1, wherein the CVAC session is a first CVAC session and the plurality of pressure targets is a first plurality of pressure targets, further comprising:
   administering a second CVAC session to the mammal in the pressure vessel unit, the second CVAC session having a start point of ambient pressure at the delivery site, an end point of ambient pressure at the delivery site, and a second plurality of pressure targets executed between the start point and the end point.

14. The method of claim 1, wherein each pressure target of the plurality of pressure targets is equivalent to a predetermined pressure, each pressure target of the plurality of pressure targets is configured to be administered for a predetermined duration.

15. A method, comprising:
   administering a Cyclic Variations in Altitude Conditioning (CVAC) program to a mammal in a pressure vessel unit, the CVAC program including at least a set-up session, a first CVAC session, and a second CVAC session, the set-up session configured to adapt the mammal to multiple pressure changes subsequently administered in the first CVAC session and the second CVAC session, the first CVAC session and the second CVAC session each being different from the set-up session,
   the first CVAC session having a start point of ambient pressure at the delivery site and an end point of ambient pressure at the delivery site, the first CVAC session including a first profile of (1) a plurality of pressure targets executed between the start point and the end point, (2) a plurality of pressure increases executed between the start point and the end point, and (3) a plurality of pressure decreases executed between the start point and the end point,
   the second CVAC session having a start point of ambient pressure at the delivery site and an end point of ambient pressure at the delivery site, the second CVAC session including a second profile of (1) a plurality of pressure targets executed between the start point and the end point, (2) a plurality of pressure increases executed between the start point and the end point, and (3) a plurality of pressure decreases executed between the start point and the end point, the second profile being different from the first profile,
   the first CVAC session including a maximum pressure target of its plurality of pressure targets, the second CVAC session including a maximum pressure target of its plurality of pressure targets, the maximum pressure target of the second CVAC session is equivalent to a pressure associated with an altitude up to 4,000 feet greater than an altitude associated with the maximum pressure target of the first CVAC session.

16. The method of claim 15, wherein:
   the maximum pressure target of the first CVAC session is an atmospheric pressure level of 10,500 feet, 14,500 feet, or 18,500 feet; and
   the maximum pressure target of the second CVAC session is an atmospheric pressure level of 14,500 feet, 18,500 feet, or 22,500 feet, respectively when the maximum pressure targets of the first CVAC sessions are 10,500 feet, 24,500 feet or 18, 500 feet, respectively.

17. The method of claim 15, wherein each pressure target of the plurality of pressure targets of each of the first profile and the second profile is (1) equivalent to a predetermined pressure, and (2) configured to be administered for a predetermined duration.

18. A method, comprising:
administering, via a pressure vessel unit, a first Cyclic Variations in Altitude Conditioning (CVAC) session to a mammal having abnormal serum lipid levels, the first CVAC session having a start point of ambient pressure at the delivery site, an end point of ambient pressure at the delivery site, and a plurality of pressure targets executed between the start point and the end point, each pressure target from the plurality of pressure targets of the first CVAC session being equivalent to an atmospheric pressure level within the range of 2,000 feet to 14,500 feet, a minimum pressure target from the plurality of pressure targets of the first CVAC session being equivalent to an atmospheric pressure level of 2,000 feet, a maximum pressure target from the plurality of pressure targets of the first CVAC session being equivalent to an atmospheric pressure level of 14,500 feet, the maximum pressure target from the plurality of pressure targets of the first CVAC session being executed during the first CVAC session; and
administering, via the pressure vessel unit, a second CVAC session to the mammal, the second CVAC session having a start point of ambient pressure at the delivery site, and end point of ambient pressure at the delivery site, and a plurality of pressure targets executed between the start point and the end point, each pressure target from the plurality of pressure targets of the second CVAC session being equivalent to an atmospheric pressure level within the range of 2,000 feet to 22,500 feet, a minimum pressure target from the plurality of pressure targets of the second CVAC session being equivalent to an atmospheric pressure level of 2,000 feet, a maximum pressure target from the plurality of pressure targets of the second CVAC session being equivalent to an atmospheric pressure level of 22,500 feet, the maximum pressure target from the plurality of pressure targets of the second CVAC session being executed during the second CVAC session.

19. A method, comprising:
administering, via a pressure vessel unit, a first Cyclic Variations in Altitude Conditioning (CVAC) session to a mammal having abnormal serum lipid levels, the first CVAC session having a start point of ambient pressure at the delivery site, an end point of ambient pressure at the delivery site, and a first plurality of pressure targets executed between the start point and the end point of the first CVAC session, each pressure target from the first plurality of pressure targets being equivalent to an atmospheric pressure level within the range of between 2,000 feet to 22,500 feet, no pressure target executed during the first CVAC session between the start point and the end point being equivalent to an atmospheric pressure level lower than 2,000 feet; and
administering a second CVAC session to the mammal in the pressure vessel unit, the second CVAC session having a start point of ambient pressure at the delivery site, an end point of ambient pressure at the delivery site, and a second plurality of pressure targets executed between the start point and the end point of the second CVAC session,
a maximum pressure target of the second plurality of pressure targets being equivalent to an atmospheric pressure level up to 4,000 feet higher than an atmospheric pressure level associated with a maximum pressure target of the first plurality of pressure targets.

* * * * *